United States Patent [19]
Kai et al.

[11] Patent Number: 6,136,837
[45] Date of Patent: Oct. 24, 2000

[54] α-SUBSTITUTED BENZYL HETEROCYCLIC DERIVATIVES, INTERMEDIATES FOR PRODUCING THE SAME AND AGROCHEMICAL COMPOSITION CONTAINING THE SAME AS ACTIVE INGREDIENT

[75] Inventors: Hiroyuki Kai, Yamatokoriyama; Akira Takase, Otsu; Toshikazu Ohtsuka, Shiga, all of Japan

[73] Assignee: Shionogi & Co., Ltd., Osaka, Japan

[21] Appl. No.: 09/161,543

[22] Filed: Sep. 28, 1998

Related U.S. Application Data

[62] Division of application No. 09/011,980, filed as application No. PCT/JP96/02765, Sep. 25, 1996, Pat. No. 5,967,440.

[30]    Foreign Application Priority Data

Sep. 29, 1995 [JP] Japan ..................... 7-277208

[51] Int. Cl.[7] ................... A01N 43/50; C07D 233/70
[52] U.S. Cl. ................... 514/400; 548/341.1
[58] Field of Search ............. 548/341.1; 514/400

[56]    References Cited

U.S. PATENT DOCUMENTS 5,719,163  2/1998  Norman et al. .............. 514/311

*Primary Examiner*—Fiona T. Powers
*Attorney, Agent, or Firm*—Wenderoth, Lind & Ponack, L.L.P.

[57]    ABSTRACT

A compound represented by the formula (I):

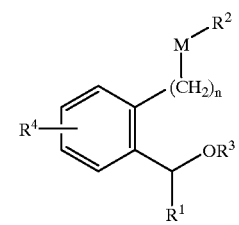

wherein $R^1$ is an optionally substituted heterocyclic group; $R^2$ is optionally substituted aryl or heterocyclic group; $R^3$ is hydrogen, alkyl, alkenyl, or alkynyl; $R^4$ is hydrogen, alkyl, alkoxy, halogen, nitro, cyano, or halogenated alkyl; M is oxygen, $S(O)_i$ wherein i is 0, 1, or 2, $NR^5$ wherein $R^5$ is hydrogen, alkyl, or acyl, —Q—N=C($R^6$)—, —B—C($R^8$)=N—, —CH=N—N=C($R^9$)—, or —CH=N—A—(CR$^{10}$R$^{11}$)m—; and n is 0, 1, or 2, an intermediate for producing the same and an agrochemical composition containing the same as an active ingredient.

19 Claims, No Drawings

α-SUBSTITUTED BENZYL HETEROCYCLIC DERIVATIVES, INTERMEDIATES FOR PRODUCING THE SAME AND AGROCHEMICAL COMPOSITION CONTAINING THE SAME AS ACTIVE INGREDIENT

This is a divisional of Ser. No. 09/011,980, filed Feb. 20, 1998, now U.S. Pat. No. 5,965,740 which is a 371 of PCT/JP96/02765, filed Sep. 25, 1996.

TECHNICAL FIELD

This invention relates to a novel α-substituted benzyl heterocyclic derivative, an intermediate for producing the same, and an agrochemical composition containing the same as an active ingredient.

BACKGROUND ART

Some α-substituted benzyl heterocyclic derivatives are known to have biological activity such as herbicidal activity, fungicidal activity etc. and pharmacological activity such as anti-arrhythmic activity, sedative activity etc.

For example, JP-A 6-49039, JP-A 7-48359, and WO 94/08975 disclose α-substituted benzyl heterocyclic derivatives showing herbicidal and fungicidal activity. However, heterocyclic rings of those are limited to pyrimidine and its fused rings. Further, any specific compounds having substituents similar to those of this invention at the ortho position of benzyl are not disclosed therein.

The object of this invention is to provide compounds having more potent fungicidal and insecticidal activity.

DISCLOSURE OF INVENTION

The present inventors have intensively researched to achieve the above object. As a result, it has been found that α-substituted benzyl heterocyclic derivatives described below show potent fungicidal and insecticidal activity. Thus, the present invention has been accomplished.

This invention relates to a compound represented by the formula (I):

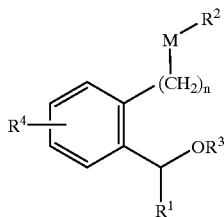

wherein $R^1$ is an optionally substituted heterocyclic group except pyrimidinyl; $R^2$ is optionally substituted aryl, or an optionally substituted heterocyclic group; $R^3$ is hydrogen alkyl, alkenyl, or alkynyl; $R^4$ is hydrogen, alkyl, alkoxy, halogen, nitro, cyano, or halogenated alkyl; M is (1) oxygen, (2) $S(O)_i$ wherein i is 0, 1, or 2, (3) $NR^5$ wherein $R^5$ is hydrogen, alkyl, or acyl, (4) —Q—N=C($R^6$)— wherein Q is oxygen or $NR^7$ wherein $R^7$ is hydrogen, alkyl, or acyl; $R^6$ is hydrogen, alkyl, acyl, alkylthio, alkylsulfinyl, alkylsulfonyl, halogenated alkyl, cyano, alkoxycarbonyl, alkoxyalkyl, optionally substituted amino, or cycloalkyl, or $R^2$ and $R^6$ taken together form a monocyclic group or a fused polycyclic group optionally having a hetero atom, (5) —B—C($R^8$)=N— wherein B is oxygen or sulfur and $R^8$ is hydrogen, alkyl, acyl, alkylthio, alkylsulfinyl, alkylsulfonyl, halogenated alkyl, cyano, alkoxycarbonyl, alkoxyalkyl, optionally substituted amino, or cycloalkyl, (6) —CH=N—N=C($R^9$)— wherein $R^9$ is hydrogen, alkyl, cyano, cycloalkyl, or halogenated alkyl, or (7) —CH=N—A—($CR^{10}R^{11}$)m— wherein $R^{10}$ and $R^{11}$ are independently hydrogen, alkyl, cyano, or halogenated alkyl, A is oxygen or $NR^{12}$ wherein $R^{12}$ is hydrogen, alkyl, or acyl, and m is 0 or 1; and n is 0, 1, or 2.

In this specification the term "lower" means to have 1 to 8 carbon atoms, preferably 1 to 6 carbon atoms, and more preferably 1 to 4 carbon atoms, unless otherwise defined.

The optionally substituted heterocyclic group represented by $R^1$ includes an unsubstituted heterocyclic group and a substituted heterocyclic group. Examples of these heterocyclic groups are 5 to 7 membered heterocyclic groups having 1 to 4 hetero atoms selected from nitrogen, sulfur, and oxygen in the ring, specifically, pyridyl such as pyridin-2-yl and pyridin-3-yl, isoxazolyl such as isoxazol-3-yl, isoxazol-4-yl, and isoxazol-5-yl, isoxazolinyl such as 2-isoxazolin-3-yl and 2-isoxazolin-5-yl, isothiazolyl such as isothiazol-5-yl, thiadiazolyl such as 1,3,4-thiadiazolyl (ex. 1,3,4-thiadiazol-2-yl) and 1,2,3-thiadiazolyl, pyridazinyl such as pyridazin-2-yl, pyrazolyl such as pyrazol-1-yl and pyrazol-5-yl, furyl such as furan-2-yl, thienyl such as thiophen-2-yl, imidazolyl such as imidazol-2-yl, oxazolyl such as oxazol-2-yl and oxazol-5-yl, thiazolyl such as thiazol-2-yl, thiazolidinyl such as thiazolidin-2-yl, oxadiazolyl such as 1,3,4-oxadiazolyl (ex. 1,3,4-oxadiazol-2-yl) and 1,2,4-oxadiazolyl, triazolyl such as 1,2,4-triazolyl (ex. 1H-1,2,4-triazol-1-yl, 4H-1,2,4-triazol-4-yl, and 1H-1,2,4-triazol-5-yl), pyrazinyl and the like.

Any of these heterocyclic groups may form a fused ring with a carbocyclic ring or another heterocyclic ring. Examples of the fused ring are benzoxazolyl such as benzoxazol-2-yl, benzothiazolyl such as benzothiazol-2-yl, benzoisoxazolyl such as benzoisoxazol-3-yl, tetramethyleneisoxazolyl such as 3,4-tetramethyleneisoxazol-5-yl and 4,5-tetramethyleneisoxazol-3-yl and the like.

These heterocyclic groups and fused rings thereof may have a bond at any possible position on the ring.

The substituents of the substituted heterocyclic group represented by $R^1$ include, for example, lower alkyl such as methyl, ethyl, propyl, and butyl, lower alkenyl such as vinyl, allyl, and 2-butenyl, lower alkynyl such as ethynyl, 2-propynyl, and 3-butynyl, cycloalkyl such as cyclopropyl, cyclopentyl, and cyclohexyl, cycloalkenyl such as cyclopentenyl and cyclohexenyl, lower alkanoyl such as acetyl, propionyl, and isobutyryl, lower alkylsilyl such as methylsilyl, ethylsilyl, propylsilyl, and butylsilyl, halogenated lower alkyl such as trifluoromethyl, trichloromethyl, chloromethyl, 2-bromoethyl, and 1,2-dichloropropyl, di(lower)alkylamino such as dimethylamino and diethylamino, phenyl, phenyl(lower)alkyl such as benzyl and phenethyl, phenyl(lower)alkenyl such as styryl and cinnamyl, furyl(lower)alkyl such as 3-furylmethyl and 2-furylethyl, furyl(lower)alkenyl such as 3-furylvinyl and 2-furylallyl, halogen such as fluorine, chlorine, bromine, and iodine, nitro, cyano, lower alkylthio such as methylthio, ethylthio, and propylthio, —$OR^{13}$ wherein $R^{13}$ is hydrogen, lower alkyl such as methyl, ethyl, and propyl, lower alkenyl such as vinyl, allyl, and 2-butenyl, lower alkynyl such as ethynyl, 2-propynyl, and 3-butynyl, lower alkanoyl such as acetyl, propionyl, and butyryl, phenyl, lower alkoxyphenyl such as 3-methoxyphenyl and 4-ethoxyphenyl, nitrophenyl such as 3-nitrophenyl and 4-nitrophenyl, cyanophenyl such as 2-cyanophenyl and 3-cyanophenyl, phenyl(lower)alkyl such as benzyl, phenethyl, and phenylpropyl, cyanophenyl (lower)alkyl such as 3-cyanophenylmethyl and 4-cyanophenylethyl, benzoyl, tetrahydropyranyl, pyridyl, trifluoromethylpyridyl, pyrimidinyl, benzothiazolyl, quinolyl, benzoyl(lower)alkyl such as benzoylmethyl and benzoylethyl, benzenesulfonyl, or lower alkyl benzenesulfonyl such as toluenesulfonyl, —CH$_2$—T—R$^{14}$ wherein T is oxygen, sulfur or NR$^{15}$ wherein R$^{15}$ is hydrogen or lower alkyl and R$^{14}$ is phenyl, halophenyl such as 2-chlorophenyl and 4-fluorophenyl, lower alkylphenyl such as 2-methylphenyl and 2,5-dimethylphenyl, lower alkoxyphenyl such as 2-methoxyphenyl and 4-ethoxyphenyl, pyridyl, or pyrimidinyl, and the like. Among those lower alkyl and halogenated alkyl are preferable, and methyl is especially preferable.

Preferred embodiments of R$^1$ include pyridin-2-yl, pyridin-3-yl, isoxazol-3-yl, isoxazol-4-yl, isoxazol-5-yl, 2-isoxazolin-3-yl, 2-isoxazolin-5-yl, imidazol-2-yl, 1,3,4-oxadiazol-2-yl, 1,2,4-oxadiazol-3-yl, and 1,2,3-thiadiazol-5-yl which are substituted optionally.

Especially preferred embodiments of R$^1$ include isoxazol-3-yl, 5-methylisoxazol-3-yl, 3-methylisoxazol-5-yl, 2-isoxazolin-3-yl, 1-methylimidazol-2-yl, and 1,3,4-oxadiazol-2-yl.

The aryl of the optionally substituted aryl represented by R$^2$ includes C6–C14 aryl such as phenyl, naphthyl (ex. 1-naphthyl and 2-naphthyl), and the like.

The optionally substituted heterocyclic group represented by R$^2$ includes an unsubstituted heterocyclic group and a substituted heterocyclic group. Examples of these heterocyclic groups are 5 to 7 membered heterocyclic groups having 1 to 4 hetero atoms selected from nitrogen, sulfur, and oxygen in the ring, specifically, pyridyl such as pyridin-2-yl, pyridin-3-yl, and pyridin-4-yl, pyrimidinyl such as pyrimidin-2-yl, pyrimidin-4-yl, and pyrimidin-5-yl, benzoxazolyl such as benzoxazol-2-yl, benzothiazolyl such as benzothiazol-2-yl, benzoimidazolyl, isoxazolyl such as isoxazol-3-yl and isoxazol-5-yl, isothiazolyl, thiadiazolyl such as 1,3,4-thiadiazolyl and 1,2,4-thiadiazolyl, pyridazinyl, pyrrolyl, pyrazolyl, furyl such as 2-furyl and 3-furyl, thienyl such as 2-thienyl and 3-thienyl, imidazolyl, oxazolyl, thiazolyl such as thiazol-2-yl, oxadiazolyl such as 1,3,4-oxadiazolyl and 1,2,4-oxadiazolyl, triazolyl such as 1,2,3-triazolyl and 1,2,4-triazolyl, quinolyl such as quinolin-2-yl, indolyl, benzisothiazolyl, benzisoxazolyl, pyrazinyl such as pyrazin-2-yl, morpholino, piperidino, piperazinyl, pyrrolidino, homopiperidino, quinazolinyl such as quinazolin-2-yl, and the like. Any of these heterocyclic groups may form a fused ring with a carbocyclic ring or another heterocyclic ring and may have a bond binding to M at any possible position on the ring.

The substituents of the substituted aryl and substituted heterocyclic group represented by R$^2$ include the same as being exemplified as those of the substituted heterocyclic group represented by R$^1$. Among those, halogen, lower alkyl, halogenated lower alkyl, lower alkoxy, halogenated lower alkoxy, lower alkylthio, phenyl, and phenoxy are preferable. Halogen, lower alkyl, halogenated lower alkyl, lower alkoxy, and halogenated lower alkoxy are more preferable. These substituents may be at any position possible to substitute on the ring. The number of the substituents, which may be the same or different from each other, is 1 to 5, preferably 1 to 4, and more preferably 1 to 3.

R$^2$ preferably includes phenyl and a heterocyclic group unsubstituted or substituted with 1 to 3 substituents selected from the group consisting of halogen, lower alkyl, halogenated lower alkyl, lower alkoxy, halogenated lower alkoxy, lower alkylthio, phenyl, and phenoxy.

Preferred embodiments of R$^2$ include phenyl; phenyl having 1 to 3 substituents selected from the group consisting of lower alkoxy (preferably methoxy), halogenated lower alkoxy (preferably trifluoromethyloxy), halogenated lower alkyl (preferably trifluoromethyl), halogen (preferably chlorine), and lower alkyl (preferably methyl), for example, 2-chlorophenyl, 3-chlorophenyl, 4-chlorophenyl, 2-methylphenyl, 3-methylphenyl, 4-methylphenyl, 2,5-dimethylphenyl, 3,4-dimethylphenyl, 4-chloro-2-methylphenyl, 3,4-dichlorophenyl, 3-trifluoromethylphenyl, 4-trifluoromethylphenyl, 4-methoxyphenyl, 3-trifluoromethyloxyphenyl, 4-trifluoromethyloxyphenyl, and the like; pyridyl substituted with halogen (preferably chlorine) and/or halogenated lower alkyl (preferably trifluoromethyl), for example, 3,5-dichloropyridin-2-yl, 5-trifluoromethylpyridin-2-yl, 5-trifluoromethyl-3-chloropyridin-2-yl, 3-trifluoromethyl-5-chloropyridin-2-yl, and the like; morpholino substituted with lower alkyl (preferably methyl), for example, 2,6-dimethylmorpholino and the like; and piperidino substituted with lower alkyl (preferably methyl), for example, 3,5-dimethylpiperidino and the like.

The alkyl represented by R$^3$ includes, for example, C1–C4 alkyl, preferably C1–C3 alkyl such as methyl, ethyl, propyl, isopropyl, and the like.

The alkenyl represented by R$^3$ includes, for example, C2–C6 alkenyl, preferably C3–C4 alkenyl such as allyl, 1-propenyl, isopropenyl, 2-butenyl, isobutenyl, and the like.

The alkynyl represented by R$^3$ includes, for example, C2–C6 alkynyl, preferably C2–C4 alkynyl such as 2-propynyl, 3-butynyl, and the like.

The preferred embodiment of R$^3$ is alkyl, especially methyl.

The alkyl represented by R$^4$ includes the same as those exemplified as alkyl represented by R$^3$.

The alkoxy represented by R$^4$ includes, for example, C1–C6 alkoxy, preferably C1–C4 alkoxy such as methoxy, ethoxy, propoxy, isopropoxy, butoxy, isobutoxy, sec-butoxy, tert-butoxy, and the like.

The halogen represented by R$^4$ includes fluorine, chlorine, bromine, and iodine.

The halogenated alkyl represented by R$^4$ includes C1–C6 alkyl, preferably C1–C4 alkyl such as methyl, ethyl, propyl, isopropyl, butyl, and the like which are substituted with at least one halogen atom such as fluorine, chlorine, bromine, or iodine, for example, difluoromethyl, trifluoromethyl, chloromethyl, 2,3-dichloropropyl, and the like. Among those trifluoromethyl is preferable.

The preferred embodiment of R$^4$ is hydrogen.

The alkyl represented by R$^5$ to R$^{12}$ includes the same as those exemplified as alkyl represented by R$^3$, preferably methyl or ethyl.

The acyl represented by R$^5$ to R$^8$, and R$^{12}$ includes alkanoyl, aroyl, and the like. The alkanoyl includes alkanoyl having C1–C6 alkyl group, preferably C1–C4 alkyl group, for example, acetyl, trifluoroacetyl, propionyl, butyryl, and the like. Among those acetyl is preferable. The aroyl includes C6–C14 aroyl, for example, benzoyl, naphthoyl, and the like. Among those benzoyl is preferable.

The halogenated alkyl represented by R$^6$, R$^8$ to R$^{11}$ includes the same as those exemplified as halogenated alkyl represented by R$^4$. Among those trifluoromethyl is preferable.

The alkoxyalkyl represented by R$^6$ and R$^8$ includes alkoxyalkyl having C1–C6 alkoxy, preferably C1–C4 alkoxy such as methoxymethyl, ethoxymethyl, methoxyethyl, and the like. Among those methoxymethyl is preferable.

The alkyl of the alkylthio, alkylsulfinyl, and alkylsulfonyl represented by $R^6$ and $R^8$ includes the same as those exemplified as alkyl represented by $R^3$. Among those methyl is preferable.

The optionally substituted amino represented by $R^6$ and $R^8$ includes amino, amino mono- or di-substituted with C1–C8 alkyl, preferably C1–C4 alkyl (e.g., monomethylamino, dimethylamino, monoethylamino, etc.), amino mono-substituted with formyl, amino mono-substituted with C2–C8 alkanoyl, preferably C2–C4 alkanoyl (e.g., methylcarbonylamino etc.), and the like.

The cycloalkyl represented by $R^6$, $R^8$, and $R^9$ includes, for example, cycloalkyl having 3 to 8 carbon atoms, preferably 3 to 6 carbon atoms, specifically cyclopropyl, cyclopentyl, cyclohexyl and the like.

The alkoxycarbonyl represented by $R^6$ and $R^8$ includes, for example, alkoxycarbonyl having C1–C6 alkyl, preferably C1–C4 alkyl, specifically methoxycarbonyl, ethoxycarbonyl, propoxycarbonyl, and the like.

When M is —Q—N=C($R^6$)—, $R^2$ and $R^6$ taken together may form a monocyclic ring or a fused polycyclic ring optionally having hetero atom(s). The monocyclic ring is formed with the carbon atom to which $R^2$ and $R^6$ are bound, includes a 4 to 8 membered ring optionally having hetero atom(s) such as oxygen, nitrogen, sulfur and the like, and may form a polycyclic ring fused with another ring. Examples of the monocyclic ring and the fused polycyclic ring include cyclopentane, cyclohexane, indan, 1,2,3,4-tetrahydronaphthalene, 5,6,7,8-tetrahydroquinoline, 4,5,6,7-tetrahydrobenzo[b]furan, and the like. These rings may have a divalent bond at any possible position.

M preferably includes oxygen, —O—N=C($R^6$)—, —CH=N—N=C($R^9$)— and —CH=N—O—(C$R^{10}R^{11}$)$_m$—.

Preferred embodiments of M include oxygen, —O—N=C(CH$_3$)—, —O—N=C(SCH$_3$)—, —O—N=C(CN)—, —O—N=C(CF$_3$)—, —CH=N—N=C(CH$_3$)—, —CH=N—O—CH(CH$_3$)— and —CH=N—O—C(CH$_3$)$_2$—.

The compounds of this invention have asymmetric carbon at the a position of the benzyl group and include each optical isomer and a mixture of these isomers in any ratio.

Examples of the compounds represented by the formula (I) include compounds shown in the examples described below. For example, the following compounds (the compound numbers are coincident with those numbered in the examples described below.) are preferable.

A compound (compound number A-12) wherein $R^1$ is 3-methylisoxazol-5-yl, $R^2$ is 2-methylphenyl, $R^3$ is methyl, $R^4$ is hydrogen, M is oxygen and n is 1;

a compound (compound number A-36) wherein $R^1$ is 3-methylisoxazol-5-yl, $R^2$ is 2,5-dimethylphenyl, $R^3$ is methyl, $R^4$ is hydrogen, M is oxygen and n is 1;

a compound (compound number A-55) wherein $R^1$ is 3-methylisoxazol-5-yl, $R^2$ is 2,3,5-trimethylphenyl, $R^3$ is methyl, $R^4$ is hydrogen, M is oxygen and n is 1;

a compound (compound number A-69) wherein $R^1$ is 3-methylisoxazol-5-yl, $R^2$ is 5-trifluoromethyl-3-chloropyridin-2-yl, $R^3$ is methyl, $R^4$ is hydrogen, M is oxygen and n is 1;

a compound (compound number A-102) wherein $R^1$ is 3-methylisoxazol-5-yl, $R^2$ is 3-trifluoromethylphenyl, $R^3$ is methyl, $R^4$ is hydrogen, M is —O—N=C(CH$_3$)— and n is 1;

a compound (compound number A-103) wherein $R^1$ is 3-methylisoxazol-5-yl, $R^2$ is 4-trifluoromethylphenyl, $R^8$ is methyl, $R^4$ is hydrogen, M is —O—N=C(CH$_3$)— and n is 1;

a compound (compound number A-323) wherein $R^1$ is 3-methylisoxazol-5-yl, $R^2$ is 2,6-dimethylmorpholino, $R^3$ is methyl, $R^4$ is hydrogen, M is —O—N=C(CH$_3$)— and n is 1;

a compound (compound number A-327) wherein $R^1$ is 3-methylisoxazol-5-yl, $R^2$ is 3,5-dimethylpiperidino, $R^3$ is methyl, $R^4$ is hydrogen, M is —O—N=C(CH$_3$)— and n is 1;

a compound (compound number A-373) wherein $R^1$ is 3-methylisoxazol-5-yl, $R^2$ is 4-trifluoromethylphenyl, $R^3$ is methyl, $R^4$ is hydrogen, M is —CH=N—O—CH(CH$_3$)— and n is 0;

a compound (compound number A-385) wherein $R^1$ is 3-methylisoxazol-5-yl, $R^2$ is 4-chlorophenyl, $R^3$ is methyl, $R^4$ is hydrogen, M is —CH=N—N=C(CH$_3$)— and n is 0;

a compound (compound number A-386) wherein $R^1$ is 3-methylisoxazol-5-yl, $R^2$ is 4-bromophenyl, $R^3$ is methyl, $R^4$ is hydrogen, M is —CH=N—N=C(CH$_3$)— and n is 0;

a compound (compound number A-388) wherein $R^1$ is 3-methylisoxazol-5-yl, $R^2$ is 4-methylphenyl, $R^3$ is methyl, $R^4$ is hydrogen, M is —CH=N—N=C(CH$_3$)— and n is 0;

a compound (compound number A-393) wherein $R^1$ is 3-methylisoxazol-5-yl, $R^2$ is 4-trifluoromethylphenyl, $R^3$ is methyl, $R^4$ is hydrogen, M is —CH=N—N=C(CH$_3$)— and n is 0;

a compound (compound number A-504) wherein $R^1$ is 3-methylisoxazol-5-yl, $R^2$ is 3-trifluoromethyloxyphenyl, $R^3$ is methyl, $R^4$ is hydrogen, M is —CH=N—N=C(CH$_3$)— and n is 0;

a compound (compound number A-505) wherein $R^1$ is 3-methylisoxazol-5-yl, $R^2$ is 4-trifluoromethyloxyphenyl, $R^3$ is methyl, $R^4$ is hydrogen, M is —CH=N—N=C(CH$_3$)— and n is 0;

a compound (compound number D-36) wherein $R^1$ is isoxazol-3-yl, $R^2$ is 2,5-dimethylphenyl, $R^3$ is methyl, $R^4$ is hydrogen, M is oxygen and n is 1;

a compound (compound number D-41) wherein $R^1$ is isoxazol-3-yl, $R^2$ is 4-chloro-2-methylphenyl, $R^3$ is methyl, $R^4$ is hydrogen, M is oxygen and n is 1;

a compound (compound number D-65) wherein $R^1$ is isoxazol-3-yl, $R^2$ is 3,5-dichloropyridin-2-yl, $R^3$ is methyl, $R^4$ is hydrogen, M is oxygen and n is 1;

a compound (compound number D-103) wherein $R^1$ is isoxazol-3-yl, $R^2$ is 4-trifluoromethylphenyl, $R^3$ is methyl, $R^4$ is hydrogen, M is —O—N=C(CH$_3$)— and n is 1;

a compound (compound number E-36) wherein $R^1$ is 5-methylisoxazol-3-yl, $R^2$ is 2,5-dimethylphenyl, $R^3$ is methyl, $R^4$ is hydrogen, M is oxygen and n is 1;

a compound (compound number E-396) wherein $R^1$ is 5-methylisoxazol-3-yl, $R^2$ is 3,4-dichlorophenyl, $R^3$ is methyl, $R^4$ is hydrogen, M is —CH=N—N=C(CH$_3$)— and n is 0;

a compound (compound number E-505) wherein $R^1$ is 5-methylisoxazol-3-yl, $R^2$ is 4-trifluoromethyloxyphenyl, $R^3$ is methyl, $R^4$ is hydrogen, M is —CH=N—N=C(CH$_3$)— and n is 0;

a compound (compound number I-12) wherein $R^1$ is 1-methylimidazol-2-yl, $R^2$ is 2-methylphenyl, $R^3$ is methyl, $R^4$ is hydrogen, M is oxygen and n is 1; and a compound (compound number I-41) wherein $R^1$ is 1-methylimidazol-2-yl, $R^2$ is 4-chloro-2-methylphenyl, $R^3$ is methyl, $R^4$ is hydrogen, M is oxygen and n is 1.

The compound (I) of this invention (Namely, the compound represented by the formula (I). The compounds represented by the other formulas may be abbreviated in the same manner.) can, for example, be manufactured according to the following synthesis routes.

Route 1

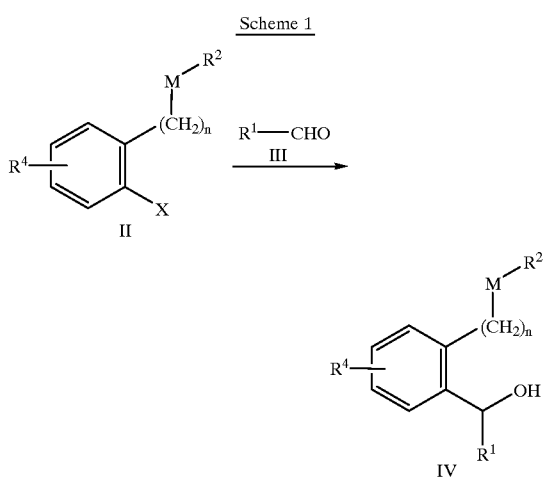

wherein X is lithium or magnesium halide (ex. —MgBr, MgI and so on) and the other symbols are the same as above.

The compound represented by the formula (IV) can be manufactured by reacting the compound (II) with the compound (III) in an appropriate pure or mixed solvent.

The amount of the compound (III) to be used in this reaction is at least one equivalent to the compound (II), preferably 1 to 3 equivalents to it.

The solvent to be used includes aromatic hydrocarbons such as toluene, benzene, xylene etc., saturated hydrocarbons such as cyclohexane, hexane etc., ethers such as tetrahydrofuran, diethyl ether, dioxane etc., triethylamine, and the mixed solvents of these.

The reaction temperature is −90 to 100° C., preferably −70 to 40° C. The reaction time varies with the compound to be used and may be 0.5 to 80 hours.

The compound (IV) obtained in this reaction is novel and one of the objects of this invention.

The compound (IV) can be used in the following step as a crude product or after being purified by the conventional methods such as column chromatography, recrystallization, etc.

The compound (II) used as starting material in this reaction can be prepared by reacting a compound which part corresponding to X is halogen with butyllithium or magnesium according to the methods of JP-A 3-246268 or JP-A 5-97768.

Route 1 (continued)

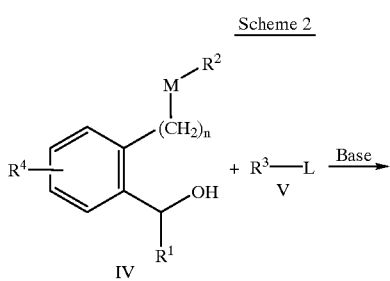

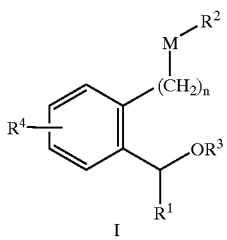

wherein L is halogen such as chlorine, bromine, iodine and the like, alkylsulfonyloxy such as lower alkylsulfonyloxy (ex. methanesulfonyloxy, ethanesulfonyloxy and the like), arylsulfonyloxy optionally substituted with halogen or lower alkyl such as benzenesulfonyloxy, p-toluenesulfonyloxy, m-toluenesulfonyloxy, o-toluenesulfonyloxy and the like or alkoxysulfonyloxy such as lower alkoxysulfonyloxy (ex. methoxysulfonyloxy, ethoxysulfonyloxy and the like) and other symbols are the same as defined above.

The compound of this invention represented by the formula (I) can be prepared by reacting the compound (IV) with the compound (V) in the presence of a base in an appropriate, pure or mixed solvent.

The amount of the compound (V) may be at least one equivalent, preferably 1 to 2 equivalents to the compound (IV) in this reaction.

Examples of the bases to be used are metal hydroxides such as sodium hydroxide, potassium hydroxide and the like, metal hydrides such as sodium hydride, potassium hydride and the like and metal alkoxides such as sodium methoxide, sodium ethoxide, potassium tert-butoxide and the like. The amount of the base may be at least one equivalent, preferably 1 to 2 equivalents to the compound (IV).

Examples of the solvents to be used are N,N-dimethylformamide, dimethylsulfoxide, aromatic hydrocarbons such as toluene, benzene, xylene and the like, saturated hydrocarbons such as cyclohexane, hexane and the like, ethers such as tetrahydrofuran, dioxane and the like, ketones such as acetone, methyl ethyl ketone and the like, water and the mixed solvents of these.

The reaction temperature is −30 to 150° C., preferably −10 to 100° C. The reaction time varies with compounds to be used and may be 0.5 to 90 hours.

The desired compound (I) thus obtained may be purified by the conventional methods such as column chromatography, recrystallization and the like, if necessary.

[Route 2]

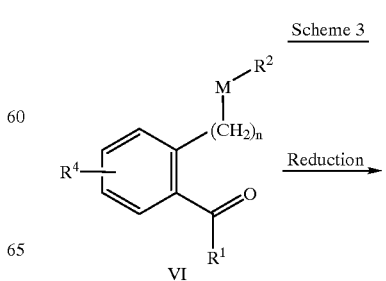

-continued

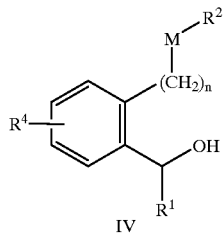

wherein each symbol is as defined above.

The compound represented by the formula (IV) can be prepared by reducing the compound (VI).

Examples of the reducing agents to be used are metal hydrides such as lithium aluminum hydride, sodium borohydride and the like. The molar ratio of the reducing agent to be used may be at least 0.25, preferably 0.25 to 1.5 to the compound (VI).

The reaction temperature is −80 to 150° C., preferably −20 to 100° C. The reaction time varies with the compounds to be used and may be 0.5 to 90 hours.

Examples of the solvents to be used are ethers such as ethyl ether, tetrahydrofuran, dioxane, ethylene glycol dimethyl ether, diethylene glycol dimethyl ether and the like, aromatic hydrocarbons such as toluene, benzene, xylene and the like and the mixed solvents of these where the reducing agent is lithium aluminum hydride, and alcohol such as methanol, ethanol, isopropanol and the like, aromatic hydrocarbons such as toluene, benzene, xylene and the like, ethers such as tetrahydrofuran, ethylene glycol dimethyl ether, diethylene glycol dimethyl ether and the like, N,N-dimethylformamide, dimethylsulfoxide, water and the mixed solvents of these where the reducing agent is sodium borohydride.

The compound (IV) may be used in the next step as a crude product or after purified by the conventional methods such as chromatography, recrystallization and the like.

The compound (VI) to be used as a starting material in this reaction may be prepared by reacting the compound (II) with reactive derivatives of carboxylic acid having an optionally substituted heterocyclic ring ($R^1$) according to the method of Japanese patent application No. 6-87819.

[Route 3]

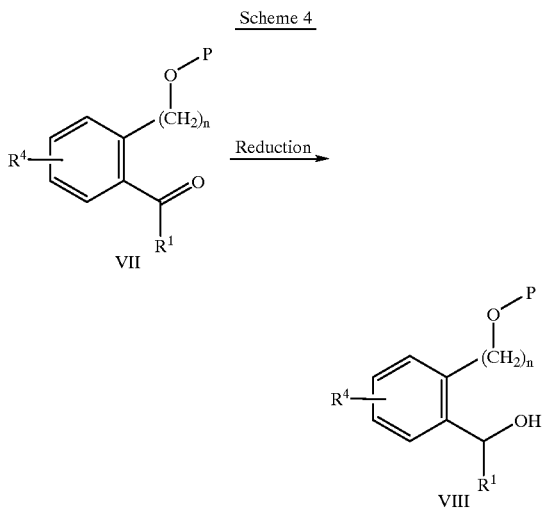

wherein P is a protecting group of a hydroxyl group and the other symbols are as defined above.

The compound represented by the formula (VIII) can be prepared by reducing the compound (VII).

The protecting group represented by P includes, for example, alkyl such as tert-butyl and the like, aralkyl such as triphenylmethyl and the like, trialkylsilyl such as tert-butyldimethylsilyl, triisopropylsilyl and the like, alkyldiarylsilyl such as tert-butyldiphenylsilyl and the like, triaralkylsilyl such as tribenzylsilyl and the like, alkoxyalkyl such as methoxymethyl, 1-ethoxyethyl, 1-methyl-1-methoxyethyl and the like, alkoxyalkoxyalkyl such as -methoxyethoxymethyl and the like, alkylthioalkyl such as methylthiomethyl and the like, tetrahydropyranyl such as tetrahydropyran-2-yl, 4-methoxytetrahydropyran-4-yl and the like, tetrahydrothiopyranyl such as tetrahydrothiopyran-2-yl and the like, tetrahydrothiofuranyl such as tetrahydrothiofuran-2-yl and the like and aralkyloxyalkyl such as benzyloxymethyl and the like.

The amount and type of the reducing agents and the solvents to be used and the reaction temperature and time are the same as described in the above Scheme 3.

The compound (VIII) may be used in the next step as a crude product or after purified by the conventional methods such as chromatography, recrystallization and the like.

The compound (VII) used in this reaction as a starting material may be prepared according to the method disclosed in Japanese patent application No. 6-87819, for example, the same method as that for preparing the compound (VI).

[Route 3 (continued)]

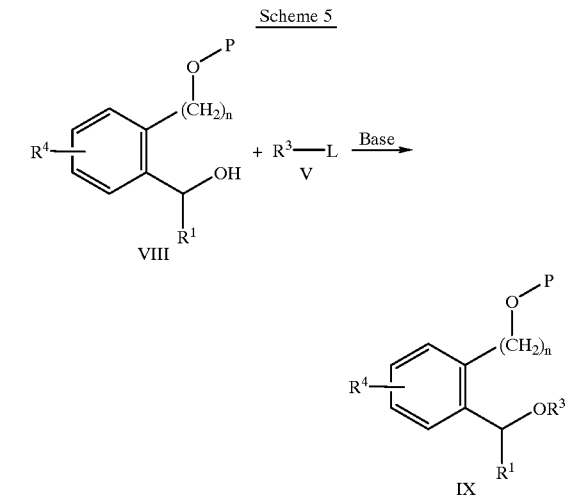

wherein each symbol is as defined above.

The compound represented by the formula (IX) can be prepared by reacting the compound (VIII) with the compound (V) in an appropriate pure or mixed solvent in the presence of a base.

The base and solvent to be used and the reaction temperature and time may be the same as those described in the above Scheme 2.

The compound (IX) may be used in the next step as a crude product or after purified by the conventional methods such as chromatography, recrystallization and the like.

[Route 3 (continued)]

Scheme 6

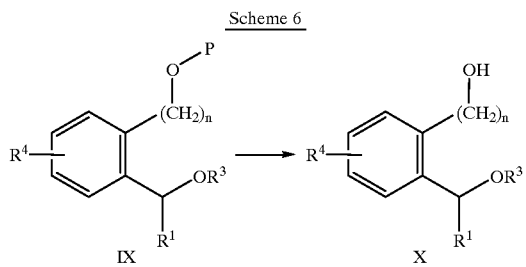

wherein each symbol is as defined above.

The compound (X) can be prepared by deprotecting the protecting group of the hydroxyl group of the compound (IX).

The deprotection of the hydroxyl group can be done by the conventional methods such as those described in T. W. Green, Protective Groups in Organic Synthesis, p.1~113, John Willy & Sons (1981); C. B. Reese, Protective Groups in Organic Chemistry, J. F. McOmie, p.95~143, Plenum Press (1973).

For example, the deprotection can be achieved by treating the compound (IX) with an acid in an appropriate solvent.

Examples of the acid to be used include inorganic acids such as hydrohalogenic acids (ex. hydrochloric acid, hydrobromic acid, hydroiodic acid and the like), hydrogen halogenides (ex. hydrogen chloride, hydrogen bromide, hydrogen iodide and the like), boric acid, phosphoric acid, sulfuric acid and the like, sulfonic acids (ex. aliphatic sulfonic acids such as trifluoromethanesulfonic acid, aromatic sulfonic acids such as toluenesulfonic acid, their pyridinium salts and the like), carboxylic acids (ex. acetic acid, trifluoroacetic acid and the like), silica gel, and Lewis acid (ex. aluminum halogenides such as aluminum chloride, zinc chloride, titanium tetrachloride and the like). One or more of acids may appropriately be selected from these to be used.

The amount of the acid to be used is a trace to 1 equivalent to the compound (IX), or carboxylic acids may be used as a solvent.

The solvent to be used varies with the reaction conditions and may include hydrocarbons such as benzene, toluene, xylene and the like, halogenated hydrocarbons such as dichloromethane, 1,2-dichloroethane and the like, ethers such as tetrahydrofuran, dioxane and the like, alcohols such as methanol, ethanol and the like, nitrites such as acetonitrile and the like, water and their mixed solvents.

The reaction temperature is −80 to 150° C., preferably −10 to 80° C. The reaction time is 1 minute to 4 hours, preferably 5 minutes to 2 hours.

Where the protecting group is substituted silyl, the deprotection can be done under the basic condition (ex. in sodium hydroxide/hydrous ethanol and the like) or in the presence of fluoride anion (ex. n-$Bu_4N^+F^-$, $C_5H_5N^+HF^-$ and the like).

The compound (X) thus obtained is novel and one of the objects of this invention. The compound (X) may be used in the next step as the reaction mixture itself or a crude product or after purified by the conventional methods such as chromatography, recrystallization and the like.

[Route 3 (continued)]

Scheme 7

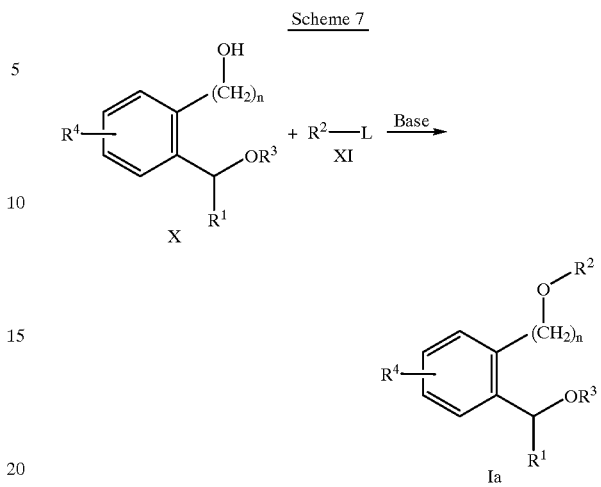

wherein each symbol is as defined above.

The compound of this invention represented by the formula (Ia) can be prepared by allowing the compound (X) to react with the compound (XI) in an appropriate pure or mixed solvent in the presence of a base.

The amount of the compound (XI) to be used in this reaction is 1 or more equivalents to the compound (X), preferably 1 to 2 equivalents.

The bases to be used include, for example, metal hydrides such as sodium hydride, potassium hydride etc., metal hydroxides such as sodium hydroxide, potassium hydroxide etc., metal carbonates such as sodium carbonate, potassium carbonate etc., and metal alkoxides such as sodium methoxide, sodium ethoxide, potassium tert-butoxide etc. The amount of the base to be used is 1 or more equivalents to the compound (X), preferably 1 to 3 equivalents.

The solvents to be used include, for example, N,N-dimethylformamide, dimethylsulfoxide, aromatic hydrocarbons such as toluene, benzene, xylene etc., saturated hydrocarbons such as cyclohexane, hexane etc., halogenated hydrocarbons such as dichloromethane, 1,2-dichloroethane etc., ethers such as tetrahydrofuran, dioxane etc., ketones such as acetone, methyl ethyl ketone etc., nitrites such as acetonitrile etc., water, and their mixed solvents.

The reaction temperature is 0 to 190° C., preferably 10 to 160° C. The reaction time varies with the compound to be used and may be 0.5 to 90 hours.

The compound (Ia) thus obtained can be purified by the conventional methods such as column chromatography, recrystallization etc. if necessary.

[Route 4]

Scheme 8

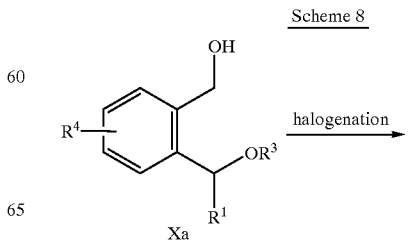

-continued

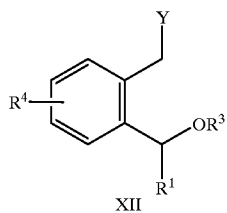

wherein Y is halogen such as chlorine, bromine or the like, and the other symbols are as defined above.

The compound represented by the formula (XII) can be prepared by reacting the compound (Xa) with a halogenating agent in an appropriate pure or mixed solvent or without any solvent.

The halogenating agents to be used include, for example, thionyl halides such as thionyl chloride, thionyl bromide etc., phosphoryl halides such as phosphoryl chloride, phosphoryl bromide etc., phosphorus halides such as phosphorus pentachloride, phosphorous trichloride, phosphorus pentabromide, phosphorus tribromide etc., carbon oxychloride, oxalyl halides such as oxalyl chloride etc., triphenylphosphinelcarbon tetrachloride, and triphenylphosphine/carbon tetrabromide. The amount to be used is 1 or more equivalents to the compound (Xa).

The solvents to be used include, for example, aromatic hydrocarbons such as toluene, benzene, xylene etc., saturated hydrocarbons such as cyclohexane, hexane etc., halogenated hydrocarbons such as dichloromethane, 1,2-dichloroethane etc., nitrites such as acetonitrile etc., and their mixed solvents.

The reaction temperature is −30 to 150° C., preferably −10 to 120° C. The reaction time varies with the compound to be used and may be 0.1 to 48 hours.

The compound (XII) thus obtained is novel and is one of the objects of this invention. The compound (XII) can be used in the following step as a crude product or after purified by the conventional methods such as column chromatography, recrystallization etc.

[Route 4 (continued)]

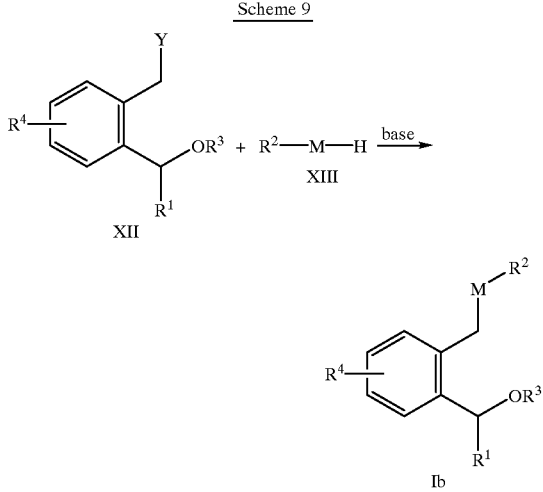

Scheme 9 wherein each symbol is as defined above.

The compound of this invention represented by the formula (Ib) can be prepared by reacting the compound (XII) with the compound (XIII) in the presence of a base in an appropriate pure or mixed solvent or without any solvent.

The amount of the compound (XIII) to be used in this reaction is 1 or more equivalents to the compound (XII).

The bases to be used include, for example, metal hydrides such as sodium hydride, potassium hydride etc., metal hydroxides such as sodium hydroxide, potassium hydroxide etc., metal carbonates such as sodium carbonate, potassium carbonate etc., and metal alkoxides such as sodium methoxide, sodium ethoxide, potassium tert-butoxide etc. The amount of the base to be used is 1 or more equivalents to the compound (XII), preferably 1 to 3 equivalents.

The solvents to be used include, for example, N,N-dimethylformamide, dimethylsulfoxide, aromatic hydrocarbons such as toluene, benzene, xylene etc., saturated hydrocarbons such as cyclohexane, hexane etc., halogenated hydrocarbons such as dichloromethane, 1,2-dichloroethane etc., ethers such as tetrahydrofuran, dioxane etc., ketones such as acetone, methyl ethyl ketone etc., nitriles such as acetonitrile etc., water, and their mixed solvents.

The reaction temperature is 0 to 190° C., preferably 10 to 160° C. The reaction time varies with the compound to be used and may be 0.5 to 90 hours.

The compound (Ib) thus obtained can be purified by the conventional methods such as column chromatography, recrystallization etc. if necessary.

[Route 5]

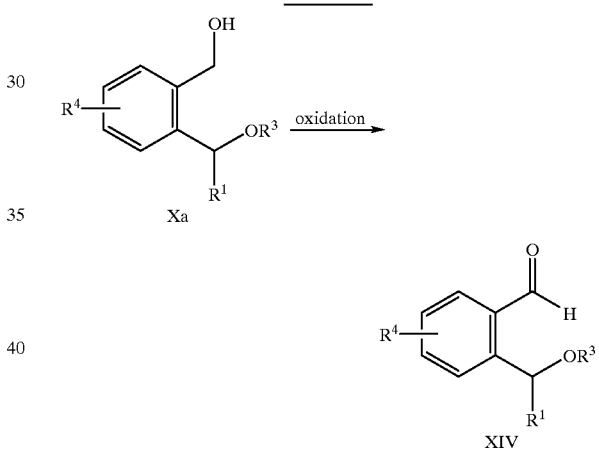

Scheme 10 wherein each symbol is as defined above.

The benzoic aldehydes represented by the formula (XIV) can be prepared by oxidizing the compound (Xa) with an oxidizing agent.

The oxidizing agents to be used include, for example, pyridinium chlorochromate, tert-butyl chromate, nickel peroxide, activated dimethylsulfoxide and the like.

In the case of the Swern oxidization, one of the known activated dimethylsulfoxide oxidization methods using activated dimethylsulfoxide, the amounts of dimethylsulfoxide and oxalyl chloride as an electrophilic reagent to be used each is 1 or more equivalents to the compound (Xa), preferably 1 to 4 equivalents.

The solvents to be used include, for example, halogenated hydrocarbons such as dichloromethane etc.

The reaction temperature is −78 to −20° C., preferably −78 to −40° C. The reaction time varies with the compound to be used and may be 15 minutes to 3 hours.

Then, a base such as triethylamine is added to form sulfonium ylide.

The amount of the base to be used is 1 or more equivalents to the compound (Xa), preferably 1 to 6 equivalents.

The reaction temperature is −78 to −50° C., preferably −78 to −30° C. The reaction time varies with the compound to be used and may be 15 minutes to 3 hours.

After the reaction, water is added thereto and the resulting product is extracted with a solvent. The compound (XIV) thus obtained can be used in the following step as a crude product or after purified by the conventional methods such as column chromatography, recrystallization etc. if necessary.

[Route 5 (continued)]

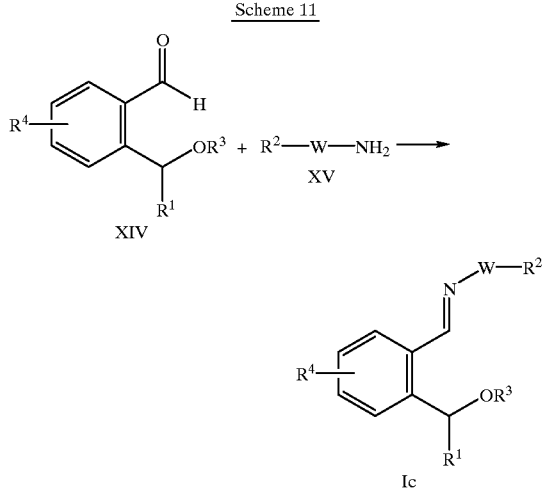

wherein W is —N=C($R^9$)— ($R^9$ is as defined above.) or —A—($CR^{10}R^{11}$)m— (A, $R^{10}$, $R^{11}$ and m are as defined above.) and the other symbols are as defined above.

The compound of this invention represented by the formula (Ic) can be prepared by reacting the compound (XIV) with the compound (XV), derivatives of hydrazone, O-substituted hydroxylamine or hydrazine, or its salt such as hydrochloride or sulfate in an appropriate pure or mixed solvent.

The amount of the compound (XV) to be used in this reaction is 1 or more equivalents to the compound (XIV), preferably 1 to 3 equivalents.

The solvents to be used include, for example, aromatic hydrocarbons such as toluene, benzene, xylene etc., saturated hydrocarbons such as cyclohexane, hexane etc., alcohols such as methanol, ethanol, propanol etc., ethers such as tetrahydrofuran, dioxane etc., water, and their mixed solvents.

The reaction temperature is 0 to 160° C., preferably 20 to 130 °. The reaction time varies with the compound to be used and may be 0.5 to 90 hours.

The compound (Ic) thus obtained can be purified by the conventional methods such as column chromatography, recrystallization etc. if necessary.

The hydrazone derivatives of the compound (XV) to be used in this reaction as a starting material can be prepared by reacting the corresponding ketone derivatives with hydrazine.

Some of the O-substituted hydroxylamine derivatives of the compound (XV) are known and the other can be prepared by the known method similar to that described in Methoden der Organischen Chemie, X/1, Houben-Weyl.

Some of the hydrazine derivatives of the compound (XV) are known and the other can be prepared by the known method similar to that described in Methoden der Organischen Chemie, X/2, Houben-Weyl.

[Route 6]

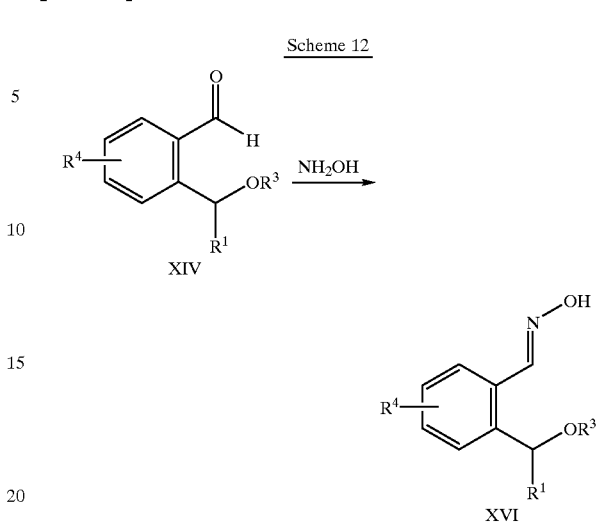

wherein each symbol is as defined above.

The compound (XVI) can be prepared by reacting the compound (XIV) with hydroxylamine or its salt in an appropriate solvent.

The amount of the hydroxylamine to be used is 1 to 4 equivalents to the compound (XIV), preferably 1 to 2.5 equivalents.

The salts of hydroxylamine include, for example, mineral acid salts such as hydrochloride, sulfate and so on. The salt is neutralized with a base to be used in this reaction. The bases to be used include, for example, metal hydroxides such as sodium hydroxide, potassium hydroxide etc., metal carbonates such as sodium carbonate, potassium carbonate etc., metal alkoxides such as sodium methoxide, sodium ethoxide etc., and pyridine, etc. The amount of the base to be used is 1 to 3 equivalents to the hydroxylamine salt, preferably 1 to 2 equivalents.

The solvents to be used include, for example, aromatic hydrocarbons such as toluene, benzene, xylene etc., halogenated hydrocarbons such as chloroform, 1,2-dichloroethane etc., ethers such as tetrahydrofuran, dioxane etc., alcohols such as methanol, ethanol, n-propanol, isopropanol etc., water, and their mixed solvents. The reaction temperature is 0 to 150° C., preferably 20 to 100° C. The reaction time varies with the compound to be used and may be 15 minutes to 24 hours.

The compound (XVI) thus obtained can be used in the following step as the reaction solution itself or a crude product or after being purified by the conventional methods such as column chromatography, recrystallization etc.

[Route 6 (continued)]

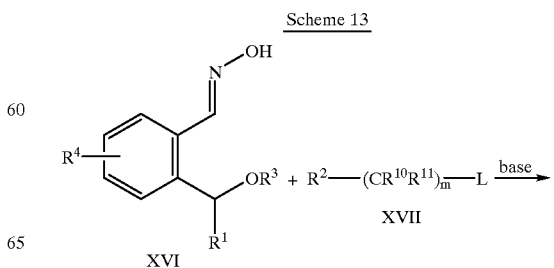

-continued

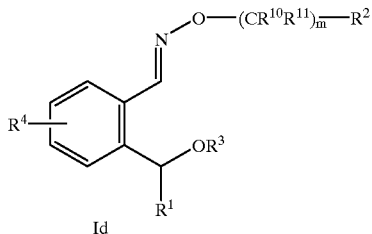

wherein each symbol is as defined above.

The compound of this invention represented by the formula (Id) can be prepared by reacting the compound (XVI) with the compound (XVII) in the presence of a base in an appropriate pure or mixed solvent or without any solvent.

The amount of the compound (XVII) to be used in this reaction is 1 or more equivalents to the compound (XVI).

The bases to be used include, for example, metal hydrides such as sodium hydride, potassium hydride etc., metal hydroxides such as sodium hydroxide, potassium hydroxide etc., metal carbonates such as sodium carbonate, potassium carbonate etc., and metal alkoxides such as sodium methoxide, sodium ethoxide, potassium tert-butoxide etc. The amount of the base to be used is 1 or more equivalents, preferably 1 to 2 equivalents.

The solvents to be used include, for example, N,N-dimethylformamide, dimethylsulfoxide, aromatic hydrocarbons such as toluene, benzene, xylene etc., saturated hydrocarbons such as cyclohexane, hexane etc., halogenated hydrocarbons such as dichloromethane, 1,2-dichloroethane etc., ethers such as tetrahydrofuran, dioxane etc., ketones such as acetone, methyl ethyl ketone etc., nitriles such as acetonitrile etc., water, and their mixed solvents.

The reaction temperature is −30 to 120° C., preferably 0 to 90° C. The reaction time varies with the compound to be used and may be 0.5 to 90 hours.

The compound (Id) thus obtained can be purified by the conventional methods such as column chromatography, recrystallization etc. if necessary.

[Route 7]

Scheme 14

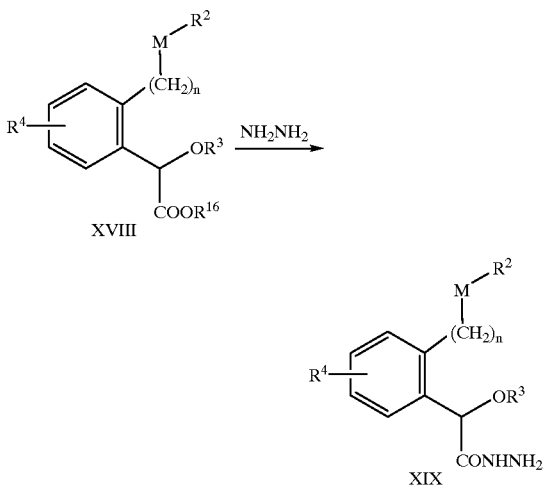

wherein $R^{16}$ is alkyl (ex. lower alkyl such as methyl, ethyl and propyl) and the other symbols are as defined above.

The compound represented by the formula (XIX) can be prepared by reacting the compound (XVIII) with hydrazine monohydrate or hydrazine salt such as hydrochloride and sulfate in an appropriate pure or mixed solvent.

The amount of hydrazine to be used in this reaction is 1 or more equivalents to the compound (VIII), preferably 1 to 7 equivalents.

The solvents to be used include, for example, aromatic hydrocarbons such as toluene, benzene, xylene etc., saturated hydrocarbons such as cyclohexane, hexane etc., alcohols such as methanol, ethanol, propanol etc., ethers such as tetrahydrofuran, dioxane etc., water, and their mixed solvents.

The reaction temperature is 0 to 160° C., preferably 10 to 130° C. The reaction time varies with the compound to be used and may be 0.5 to 90 hours.

The compound (XIX) thus obtained can be used in the following step as the reaction solution itself or a crude product or after being purified by the conventional methods such as column chromatography, recrystallization etc.

The compound (XVIII) to be used in this reaction as a starting material can be prepared by, for example, reducing the corresponding α-ketocarboxylate ester followed by alkylation, alkenylation or alkynylation according to the method described in PCT/JP95100663.

[Route 7 (continued)]

Scheme 15

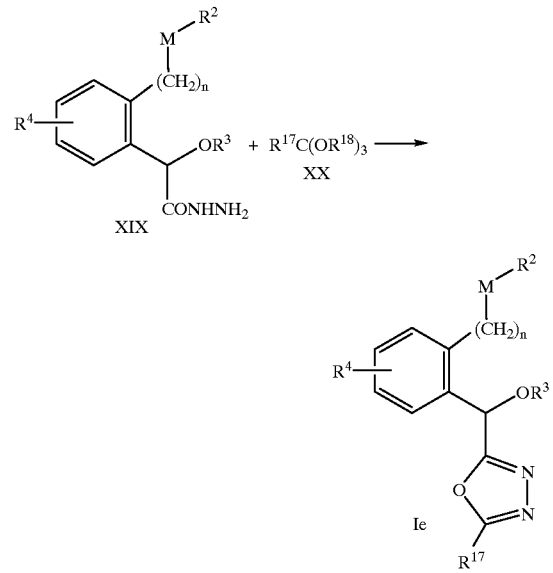

wherein $R^{17}$ and $R^{18}$ each is alkyl (ex. lower alkyl such as methyl, ethyl and propyl) and the other symbols are as defined above.

The compound of this invention represented by the formula (Ie) can be prepared by reacting the compound (XIX) with the compound (XX) in the presence or absence of an acid in an appropriate pure or mixed solvent or without any solvent according to the method of C. Ainaworth, J. Am. Chem. Soc., 77, 1148 (1955).

The amount of the compound (XX) to be used in this reaction is 1 or more equivalents to the compound (XIX), preferably 1 to 20 equivalents.

The acid to be used includes, for example, hydrogen halides such as hydrogen chloride, hydrogen bromide, hydrogen iodide etc., and sulfonic acids (ex. aliphatic sulfonic acid such as trifluoromethanesulfonic acid and aromatic sulfonic acid such as toluenesulfonic acid).

The amount of the acid to be used is a trace to 1 equivalent to the compound (XIX).

The solvents to be used include, for example, aromatic hydrocarbons such as toluene, benzene, xylene etc., saturated hydrocarbons such as cyclohexane, hexane etc., ethers such as tetrahydrofuran, dioxane etc., and their mixed solvents.

The reaction temperature is 20 to 200° C., preferably 50 to 170° C. The reaction time varies with the compound to be used and may be 0.5 to 90 hours.

The compound (Ie) thus obtained can be purified by the conventional methods such as column chromatography, recrystallization etc. if necessary.

The compound (I) of this invention is effective against pathogenic microbes (fungi) and soil fungi on crop plants or their seeds such as rice, wheat, barley, rye, corn, millet, foxtail millet, buckwheat, soybean, redbean, peanut, etc., fruit trees such as citrus fruits, grape, apple, pear, peach, etc., or vegetables such as cucumber, eggplant, tomato, pumpkin, kidney bean, etc. The compound of this invention shows potent fungicidal activity particularly against *Pyricularia oryzae, Rhizoctonia solani, Erysiphe graminis, Sphaerotheca fuliginea, Erysiphe cichoracearum, Phylophthora infestans, Pseudoperonospora cubensis, Peronospora manshurica, Plasaopara viticola, Botrytis cinerea* of vegetables, grape and so on, *Pythium aphanidermatum, Sclerotinia sclerotiorum* of buckwheat, soybean, colza and so on, *Corticium rolfsii* of soybean, redbean, potato, peanut and so on, *Pseudocercosporella herpotrichoides* and so on. Therefore, the compound (I) of this invention is useful as fungicides, particularly as agricultural fungicides.

The compound (I) of this invention also shows potent insecticidal activity on injurious insects to plants. Particularly, it shows potent preventing activity against insects such as *Myzus persicae* etc. injuring plants. Therefore, the compound (I) of this invention is also useful as insecticides.

Application of the compound (I) of this invention as fungicides may be made to plants by any conventional procedure such as atomizing, scattering or spreading of the active compound. Application may also be made through treatment of seeds of plants, soil where plants grow, soil for seeding, paddy field or water for perfusion with the active compound. Application may be performed before or after the infection with phytopathogenic fungi on plants.

Application of the compound (I) of this invention as insecticides may be made to insects by any conventional procedure such as atomizing, scattering or spreading of the active compound. In order to prevent injuries by insects, application of the compound (I) of this invention may also be made to plants by any conventional procedure such as atomizing, scattering or spreading of the active compound. Further, application may be made through treatment of seeds of plants, soil where plants grow, soil for seeding, paddy field or water for perfusion with the active compound.

The compound can be used in a conventional formulation form suitable for agricultural fungicides and insecticides such as solutions, wettable powders, emulsions, suspensions, concentrated liquid preparations, tablets, granules. aerosols, powders, pastes, fumigants, flowable, etc.

Such formulation form can be prepared in a conventional manner by mixing at least one compound of this invention with an appropriate solid or liquid carrier(s) and, if necessary, an appropriate adjuvant(s) (e.g., surfactants, spreaders, dispersants, stabilizers, etc.) for improving the dispersibility and other properties of the active ingredient.

Examples of the solid carriers or diluents include botanical materials (e.g., flour, tobacco stalk powder, soybean powder, walnut-shell powder, vegetable powder, saw dust, bran, bark powder, cellulose powder, vegetable extract residue, etc.), fibrous materials (e.g., paper, corrugated cardboard, old rags, etc.), artificial plastic powders, clays (e.g., kaolin, bentonite, fuller's earth, etc.), talc, other inorganic materials (e.g., pyrophyllite, sericite, pumice, sulfur powder, active carbon, etc.), chemical fertilizers (e.g., ammonium sulfate, ammonium phosphate, ammonium nitrate, urea, ammonium chloride, etc.), etc.

Examples of the liquid carriers or diluents include water, alcohols (e.g., methanol, ethanol, etc.), ketones (e.g., acetone, ethyl methyl ketone, etc.), ethers (e.g., diethyl ether, dioxane, cellosolve, tetrahydrofuran, etc.), aromatic hydrocarbons (e.g., benzene, toluene, xylene, methylnaphthalene, etc.), aliphatic hydrocarbons (e.g., gasoline, kerosene, lamp oil, etc.), esters, nitriles, acid amides (e.g., N,N-dimethylformamide, N,N-dimethylacetamide, etc.), halogenated hydrocarbons (e.g., dichloroethane, carbon tetrachloride, etc.), etc.

Examples of the surfactants include alkyl sulfates, alkyl sulfonates, alkylaryl sulfonates, polyethylene glycol ethers, polyhydric alcohol esters, etc.

Examples of the spreaders or dispersants include casein, gelatin, starch powder, carboxymethyl cellulose, gum arabic, alginic acid, lignin, bentonite, molasses, polyvinyl alcohol, pine oil, agar, etc. Examples of the stabilizers include PAP (a mixture of isopropylphosphate), tricresyl phosphate (TCP), tall oil, epoxidized oil, surfactants, fatty acids and their esters, etc.

The composition of the present invention may contain other fungicides, insecticides, herbicides or fertilizers in addition to the above ingredients.

In general the above composition contains at least one compound of the formula (1) of the present invention in a concentration of 0.1 to 95% by weight, preferably 1.0 to 80% by weight. The composition can be used as such or in a diluted form. About 1 g to 5 kg/hectare, preferably about 10 g to 1.0 Kg/hectare, of the compound of the present invention is used in a concentration of normally about 1 to 5,000 ppm, preferably about 10 to 1,000 ppm.

EXAMPLES

The following Examples and Test Examples further illustrate the present invention in detail, but are not to be construed to limit the scope thereof. The $^1$H-NMR (CDCl$_3$) data in Examples were determined at 270 or 400 MHz in CDCl$_3$ using tetramethylsilane as an internal standard and indicated in δ values (ppm). The coupling constants (J) are indicated in Hz. In the data, s is a singlet, d is a doublet, t is a triplet, q is a quartet, quint is a quintet sept is a septet, m is a multiplet, and brs is a broad singlet .

Example 1

Synthesis of 2-[2-(2,5-dimethylphenoxymethyl)-α-hydroxybenzyl]pyridine (Compound No. IV-21)

A mixture of 2.91 g (0.01 mol) of 1-bromo-2-(2,5-dimethylphenoxymethyl) benzene and 8 ml of THF was added to a suspension of 0.36 g (0.015 mol) of magnesium, 0.1 ml of bromoethane, and 2 ml of tetrahydrofuran at 45 to 55° C. over 5 minutes under a nitrogen gas atmosphere and stirred at 50 to 55° C. for an hour to prepare a Grignard's reagent. The Grignard's reagent was added to a mixture of 1.18 g (0.011 mol) of 2-pyridinecarboxyaldehyde and 10 ml of THF below 5° C. over 15 minutes and stirred at room temperature for 2 hours. After completion of the reaction, 150 ml of an aqueous solution of ammonium chloride was added and extracted with 150 ml of ether. After the extract was dried over anhydrous magnesium sulfate and concentrated under reduced pressure, the residue thus obtained was purified by column chromatography on silica gel (ethyl acetate/n-hexane) to give 2.42 g of 2-[2-(2,5-dimethylphenoxymethyl)-α-hydroxybenzyl]pyridine (75.8% yield) as colorless oil.

$^1$H-NMR (CDCl$_3$) δ ppm: 2.16 (3H, s), 2.29 (3H, s), 4.96 (1H, d, J=11.6), 5.32 (1H, d, J=11.6), 5.33 (1H, s), 6.05 (1H, d, J=1.8), 6.64 (1H, s), 6.67 (1H, d, J=7.3), 7.00 (1H, d, J=7.3), 7.16–7.64 (7H, m), 8.57 (1H, dd, J=4.9, 1.8).

Example 2

Synthesis of 2-[2-(2,5-dimethylphenoxymethyl)-α-methoxybenzyl]pyridine (Compound No. J-36)

To a mixture of 0.42 g (1.3 mmol) of 2-[2-(2,5-dimethylphenoxymethyl)-α-hydroxybenzyl]pyridine, 4 ml of N,N-dimethylformamide and 0.12 ml (2 mmol) of methyl iodide was added 0.07 g (1.7 mmol) of 60% sodium hydride under ice-cooling and stirred at the same temperature for 3 hours. After completion of the reaction, 100 ml of ether was added and washed twice with 80 ml of brine. The ether layer was dried over anhydrous magnesium and concentrated under reduced pressure. The residue was purified by column chromatography on silica gel (ethyl acetate/n-hexane) to give 2-[2-(2,5-dimethylphenoxymethyl)-α-methoxybenzyl]pyridine (0.40 g, 92.3%) as colorless oil.

$^1$H-NMR (CDCl$_3$) δ ppm: 2.19 (3H, s), 2.29 (3H, s), 3.45 (3H, s), 5.13 (1H, d, J=12.3), 5.27 (1H, d, J=12.3), 5.67 (1H, s), 6.65 (1H, s), 6.67 (1H, d, J=7.3), 7.01 (1H, d, J=7.3), 7.12–7.69 (7H, m), 8.53 (1H, dd, J=4.9, 1.8).

Example 3

Synthesis of 2-[2-(4-chloro-2-methylphenoxymethyl)-α-hydroxybenzyl]-1-methylimidazole (Compound No. IV-17)

To a mixture of 1.02 g (3 mmol) of 2-(4-chloro-2-methylphenoxymethyl)phenyl 1-methylimidazol-2-yl ketone, 6 ml of tetrahydrofuran and 3 ml of methanol was added 0.11 g (3 mmol) of sodium borohydride under ice-cooling and stirred at room temperature for an hour. After completion of the reaction, 100 ml of brine was added and extracted twice with 50 ml of dichloromethane. The extract was dried over anhydrous magnesium and concentrated under reduced pressure. The crystal thus obtained was recrystallized from ethyl acetate to give 2-[2-(4-chloro-2-methylphenoxymethyl)-α-hydroxybenzyl]-1-methylimidazole (0.57 g, 55.4%) as colorless crystals. mp. 159–160° C.

$^1$H-NMR (CDCl$_3$) δ ppm: 2.19 (3H, s), 3.36 (3H, s), 4.98 (1H, d, J=12.2), 5.26 (1H, d, J=12.2), 6.10 (1H, s), 6.77 (1H, d, J=7.9), 6.84 (1H, s), 7.00 (1H, s), 7.07–7.54 (6H, m).

According to the same manner as that of the synthesis of the intermediate in Example 1 or 3, various compounds of the formula (IV) of this invention, which are intermediates for production of the compound (I), were synthesized. The compounds thus obtained and their physical data are shown in the following Tables 1–3. In the following tables the physical data of the compounds obtained in Examples 1 and 3 are also listed.

TABLE 1

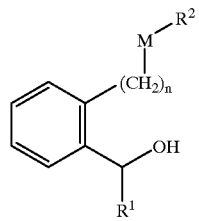

| No | R$^1$ | R$^2$ | M | n | Physical data |
|---|---|---|---|---|---|
| IV-1 | 3-Me-5-isoxazolyl | C$_6$H$_5$ | O | 0 | $^1$H-NMR(CDCl$_3$) δ ppm: 2.23(3H, s), 2.99(1H, d, J=6.1), 5.99(1H, s), 6.17(1H, d, J=6.7), 6.83–7.53(9H, m). |
| IV-2 | 3-Me-5-isoxazolyl | 4-Ph—C$_6$H$_4$ | O | 1 | $^1$H-NMR(CDCl$_3$) δ ppm: 2.25(3H, s), 3.08(1H, d, J=4.3), 5.08(1H, d, J=11.6), 5.19(1H, d, J=11.0), 6.00(1H, s), 6.17(1H, d, J=4.3), 6.99(2H, d, J=8.5), 7.28–7.56(11H, m). |
| IV-3 | 3-Me-5-isoxazolyl | 3-CF$_3$—C$_6$H$_4$ | O | 1 | $^1$H-NMR(CDCl$_3$) δ ppm: 2.25(3H, s), 2.88(1H, d, J=4.3), 5.10(1H, d, J=11.0), 5.18(1H, d, J=11.6), 5.96(1H, s), 6.15(1H, d, J=4.3), 7.06–7.56(8H, m). |
| IV-4 | 3-Me-5-isoxazolyl | 2,5-Me$_2$—C$_6$H$_3$ | O | 1 | $^1$H-NMR(CDCl$_3$) δ ppm: 2.14(3H, s), 2.26(3H, s), 2.32(3H, s), 3.10(1H, d, J=4.9), 5.01(1H, d, J=11.6), 5.13(1H, d, J=11.6), 6.01(1H, s), 6.16(1H, d, J=4.9), 6.71(1H, s), 6.72(1H, d, J=7.9), 7.03(1H, d, J=7.9), 7.36–7.52(4H, m). |
| IV-5 | 3-Me-5-isoxazolyl | 4-Cl-2-Me—C$_6$H$_3$ | O | 1 | $^1$H-NMR(CDCl$_3$) δ ppm: 2.15(3H, s), 2.25(3H, s), 2.94(1H, d, J=4.9), 5.04(1H, d, J=11.6), 5.11(1H, d, J=11.6), 5.96(1H, s), 6.15(1H, d, J=4.9), 6.78(1H, d, J=8.6), 7.08–7.12(2H, m), 7.39–7.54(4H, m). |
| IV-6 | 3-Et-5-isoxazolyl | 2,5-Me$_2$—C$_6$H$_3$ | O | 1 | $^1$H-NMR(CDCl$_3$) δ ppm: 1.23(3H, t, J=7.3), 2.13(3H, s), 2.32(3H, s), 2.65(2H, q, J=7.3), 3.16(1H, d, J=4.9), 5.01(1H, d, J=11.6), 5.12(1H, d, J=11.6), 6.04(1H, s), 6.16(1H, d, |

TABLE 1-continued

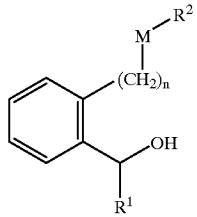

| No | R¹ | R² | M | n | Physical data |
|---|---|---|---|---|---|
| IV-7 | 3-Me-2-isoxazolin-5-yl | 2,5-Me₂—C₆H₃ | O | 1 | J=4.9), 6.71(1H, s), 6.72(1H, d, J=7.9), 7.03(1H, d, J=7.9), 7.39–7.50(4H, m). ¹H-NMR(CDCl₃) δ ppm: 1.87(3H, s), 2.16(3H, s), 2.34(3H, s), 2.79–2.88(3H, m), 4.88–5.29(4H, m), 6.73(1H, d, J=7.9), 6.79(1H, s), 7.03(1H, d, J=7.3), 7.34–7.56(4H, m). |

TABLE 2

| No | R¹ | R² | M | n | Physical data |
|---|---|---|---|---|---|
| IV-8 | 3-isoxazolyl | 2,5-Me₂-C₆H₃ | O | 1 | mp 86~87° C. |
| IV-9 | 3-isoxazolyl | 4-Cl-2-Me-C₆H₃ | O | 1 | mp 89~91° C. |
| IV-10 | 5-Me-3-isoxazolyl | 2-Me-C₆H₄ | O | 1 | ¹H-NMR(CDCl₃) δ ppm:2.23(3H, s), 2.37(3H, s), 2.97(1H, d, J=3.7), 5.11(1H, d, J=11.6), 5.18(1H, d, J=11.8), 5.90(1H, s), 6.20(1H, d, J=4.3), 6.87–6.91(2H, m), 7.13–7.18(2H, m), 7.34–7.55(4H, m). |
| IV-11 | 5-Me-3-isoxazolyl | 2,5-Me₂-C₆H₃ | O | 1 | ¹H-NMR(CDCl₃) δ ppm:2.18(3H, s), 2.32(3H, s), 2.37(3H, s), 2.99(1H, d, J=4.3), 5.09(1H, d, J=11.6), 5.17(1H, d, J=11.6), 5.91(1H, s), 6.20(1H, d, J=4.3), 6.71(1H, d, J=7.3), 6.73(1H, s), 7.03(1H, d, J=7.3), 7.36–7.54(4H, m). |
| IV-12 | 3,5-Me₂-4-isoxazolyl | 2,5-Me₂-C₆H₃ | O | 1 | mp 188~119° C. |
| IV-13 | 4-Me-1,2,3-thiadiazol-5-yl | C₆H₅ | O | 1 | ¹H-NMR(CDCl₃) δ ppm:2.36(3H, s), 3.44(1H, d, J=3.7), 5.09(1H, d, J=10.4), 5.20(1H, d, J=10.4), 6.39(1H, d, J=3.7), 6.92–6.95(2H, m), 7.03(1H, t, J=7.9), 7.20–7.53(6H, m). |
| IV-14 | 4-Me-1,2,3-thiadiaxol-5-yl | 2,5-Me₂-C₆H₃ | O | 1 | mp 122~123° C. |

TABLE 3

| No | R¹ | R² | M | n | Physical data |
|---|---|---|---|---|---|
| IV-15 | 1-Me-2-imidazolyl | C₆H₅ | O | 1 | ¹H-NMR(CDCl₃) δ ppm: 3.38(3H, s), 4.22(1H, brs), 4.99(1H, d, J=11.6), 5.34(1H, dd, J=11.6, 3.1), 6.14(1H, s), 6.84(1H, s), 6.92–7.03(3H, m), 7.15(1H, d, J=4.9), 7.29–7.64(6H, m). |
| IV-16 | 1-Me-2-imidazolyl | 2-Me-C₆H₄ | O | 1 | mp 130~131° C. |
| IV-17 | 1-Me-2-imidazolyl | 4-Cl-2-Me-C₆H₃ | O | 1 | mp 159~160° C. |
| IV-18 | 1-Me-2-imidazolyl | C₆H₅ | —ON=C(Me)— | 1 | mp 104~105° C. |
| IV-19 | 1-Me-2-imidazolyl | 4-Cl-C₆H₅ | —ON=C(Me)— | 1 | |

TABLE 3-continued

| No | R¹ | R² | M | n | Physical data |
|---|---|---|---|---|---|
| IV-20 | 1-Me-2-imidazolyl imidazolyl | 2,5-Me₂-C₆H₃ | O | 1 | |
| IV-21 | 2-pyridyl | 2,5-Me₂-C₆H₃ | O | 1 | ¹H-NMR(CDCl₃) δ ppm:2.16(3H, s), 2.29(3H, s), 4.96(1H, d, J=11.6), 5.32(1H, d, J=11.6), 5.33(1H, s), 6.05(1H, d, J=1.8), 6.64(1H, s), 6.67(1H, d, J=7.3), 7.00(1H, d, J=7.3), 7.16–7.64(7H, m), 8.57(1H, dd, J=4.9, 1.8). |
| IV-22 | 3-pyridyl | 2,5-Me₂-C₆H₃ | O | 1 | ¹H-NMR(CDCl₃) δ ppm:2.13(3H, s), 2.31(3H, s), 3.09(1H, brs), 5.00(1H, d, J=11.6), 5.07(1H, d, J=11.6), 6.19(1H, s), 6.66(1H, s), 6.72(1H, d, J=7.3), 7.02(1H, d, J=7.3), 7.23–7.73(6H, m), 8.51(1H, dd, J=4.9, 1.8), 8.58(1H, d, J=1.8). |

Example 4

Synthesis of 2-[2-(4-chloro-2-methylphenoxymethyl)-α-ethoxybenzyl]-1-methylimidazole (Compound No. I-449)

To a mixture of 0.34 g (0.9 mmol) of 2-[2-(4-chloro-2-methylphenoxymethyl)-α-hydroxybenzyl]-1-methylimidazole, 3 ml of N,N-dimethylformamide and 0.13 ml (1.8 mmol) of ethyl bromide was added 0.05 g (1.3 mmol) of 60% sodium hydride under ice-cooling and stirred at the same temperature for 3 hours. After completion of the reaction, 100 ml of ether was added and washed twice with 80 ml of brine. The ether layer was dried over anhydrous magnesium and concentrated under reduced pressure. The residue was purified by column chromatography on silica gel (ethyl acetate/n-hexane) to give 2-[2-(4-chloro-2-methylphenoxymethyl)-α-ethoxybenzyl]-1-methylimidazole (0.30 g, 89.9%) as colorless oil.

¹H-NMR (CDCl₃) δ ppm: 1.26 (3H, t, J=7.3), 2.20 (3H, s), 3.46–3.64 (2H, m), 3.55 (3H, s), 4.95 (1H, d, J=12.8), 5.10 (1H, d, J=12.8), 5.84 (1H, s), 6–72(1H, d, J=8.6), 6.82 (1H, d, J=1.2), 6.94 (1H, d, J=1.2), 7.04–7.54 (6H, m).

Example 5

Synthesis of 5-[2-(1-ethoxyethyl)oxymethyl-α-methoxybenzyl]-3-methylisoxazole

To a mixture of 3.18 g (11 mmol) of 2-(1-ethoxyethyl)oxymethylphenyl 3-methylisoxazol-5-yl ketone, 11 ml of tetrahydrofuran and 11 ml of methanol was added 0.42 g (11 mmol) of sodium borohydride under ice-cooling and stirred at room temperature for an hour. After completion of the reaction, 300 ml of brine was added and extracted twice with 100 ml of dichloromethane. The extract was dried over anhydrous magnesium and concentrated under reduced pressure to give 3.30 g of a crude product of 5-[2-(1-ethoxyethyl)oxymethyl-α-hydroxybenzyl]-3-methylisoxazole. To the crude product, 22 ml of N,N-dimethylformamide and 1.03 ml (16.5 mmol) of methyl iodide was added and then 0.57 g (14.3 mmol) of 60% sodium hydride was added under ice-cooling and stirred at the same temperature for an hour. After completion of the reaction, 200 ml of ether was added and washed twice with 200 ml of brine. The ether layer was dried over anhydrous magnesium and concentrated under reduced pressure. The residue was purified by column chromatography on silica gel (ethyl acetate/n-hexane) to give 5-[2-(1-ethoxyethyl)oxymethyl-α-methoxybenzyl]-3-methylisoxazole (3.18 g, 94.7%) as colorless oil.

¹H-NMR (CDCl₃) δ ppm: 1.21 (1.21) (3H, t, J=7.0), 1.31 (1.32) (3H, d), 2.24 (3H, s), 3.47–3.67 (2H, m), 4.47–4.80 (3H, m), 5.72 (5.75) (1H, s), 5.89 (1H, s), 7.30–7.55 (4H, m).

Example 6

Synthesis of 5-(2-hydroxymethyl-α-methoxybenzyl)-3-methylisoxazole (Compound No. X-1)

To 3.05 g (10 mmol) of 5-[2-(1-ethoxyethyl)oxymethyl-α-methoxybenzyl]-3-methylisoxazole was added 0.25 g (1 mmol) of pyridinium p-toluenesulfonate and stirred under reflux for an hour. After completion of the reaction, 150 ml of brine was added and extracted twice with 80 ml of dichloromethane. The extract was dried over anhydrous magnesium and concentrated under reduced pressure to give 5-(2-hydroxymethyl-α-methoxybenzyl)-3-methylisoxazole (2.33 g, 99.9%) as colorless oil.

¹H-NMR (CDCl₃) δ ppm: 2.12 (1H, brs), 2.27 (3H, s), 3.47 (3H, s), 4.70 (2H, s), 5.70 (1H, s), 6.00 (1H, s), 7.34–7.44 (4H, m).

According to the same manner as that of the synthesis of the intermediate in Example 6, various compounds of the formula (X) of this invention, which are intermediates for production of the compound (I), were synthesized. The compounds thus obtained and their physical data are shown in the following Table 4. In the following table the physical data of the compound (X-1) obtained in Example 6 are also listed.

TABLE 4

| No | R¹ | R³ | n | Physical data |
|---|---|---|---|---|
| X-1 | 3-Me-5-isoxazolyl | Me | 1 | ¹H-NMR(CDCl₃) δ ppm: 2.12(1H, brs), 2.27(3H, s), 3.47(3H, s), 4.70(2H, s), 5.70(1H, s), 6.00(1H, s), 7.34–7.44(4H, m). |
| X-2 | 3-isoxazolyl | Me | 1 | ¹H-NMR(CDCl₃) δ ppm: 2.62(1H, dd, J=7.3, 5.5), 3.44(3H, s), 4.66–4.82(2H, m), 5.84(1H, s), 6.40(1H, d, J=1.8), 7.32–7.52(4H, m), 8.34(1H, d, J=1.8). |
| X-3 | 5-Me-3-isoxazolyl | Me | 1 | ¹H-NMR(CDCl₃) δ ppm: 2.38(3H, d, J=1.2), 2.78(1H, t, J=7.3), 3.43(3H, s), 4.61–4.82(2H, m), 5.73(1H, s), 6.02(1H, s), 7.31–7.53(4H, m). |
| X-4 | 3-Me-5-isoxazolyl | Me | 0 | ¹H-NMR(CDCl₃) δ ppm: 2.25(3H, s), 3.56(3H, s), 5.51(1H, s), 5.97(1H, s), 6.85–7.29(4H, m), 7.43(1H, s) |
| X-5 | 5-Me-3-isoxazolyl | Me | 0 | |
| X-6 | 3-isoxazolyl | Me | 0 | |
| X-7 | 3-Me-5-isoxazolyl | Et | 0 | |
| X-8 | 3-Me-5-isoxazolyl | Et | 1 | |
| X-9 | 3,4-tetramethylene-5-isoxazolyl | Me | 1 | ¹H-NMR(CDCl₃) δ ppm: 1.64–1.80(4H, m), 2.22(1H, t, J=6.1), 2.31–2.47(2H, m), 2.72(2H, t, J=6.7), 3.45(3H, s), 4.62–4.74(2H, m), 5.73(1H, s), 7.32–7.45(4H, m). |
| X-10 | 4,5-tetramethylene-3-isoxazolyl | Me | 1 | ¹H-NMR(CDCl₃) δ ppm: 1.64–1.86(4H, m), 2.25–2.35(1H, m), 2.41–2.51(1H, m), 2.63–2.67(2H, m), 2.94(1H, t, J=7.3), 3.43(3H, s), 4.64–4.81(2H, m), 5.77(1H, s), 7.29–7.51(4H, m). |
| X-11 | 2-isoxazolin-3-yl | Me | 1 | ¹H-NMR(CDCl₃) δ ppm: 2.37(1H, brs), 2.74–3.10(2H, m), 3.42(3H, s), 4.21–4.37(2H, m), 4.68–4.81(2H, m), 5.53(1H, s), 7.31–7.53(4H, m). |

Example 7

Synthesis of 5-[2-(3-chloro-5-trifluoromethyl-2-pyridyloxymethyl)-α-methoxybenzyl]-3-methylisoxazole (Compound No. A-69)

To a mixture of 0.21 g (0.9 mmol) of 5-(2-hydroxymethyl-α-methoxybenzyl)-3-methylisoxazole, 3 ml of tetrahydrofuran and 0.29 g (1.35 mmol) of 2,3-dichloro-5-trifluoromethylpyridine was added 0.05 g (1.3 mmol) of 60% sodium hydride under ice-cooling and stirred at room temperature for 2 hours. After completion of the reaction, 100 ml of ether was added and washed with 80 ml of brine. The ether layer was dried over anhydrous magnesium and concentrated under reduced pressure. The residue was purified by column chromatography on silica gel (ethyl acetate/n-hexane) to give 5-[2-(3-chloro-5-trifluoromethyl-2-pyridyloxymethyl)-α-methoxybenzyl]-3-methylisoxazole (0.32 g, 86.1%) as colorless oil.

¹H-NMR (CDCl₃) δ ppm: 2.24 (3H, s), 3.46 (3H, s), 5.57 (2H, s), 5.79 (1H, s), 5.91 (1H, s), 7.35–7.56 (4H, m), 7.85 (1H, d, J=2.2), 8.33 (1H, t, J=1.2).

Example 8

Synthesis of 5-(2-chloromethyl-α-methoxybenzyl)-3-methylisoxazole (Compound No. XII-1)

To a mixture of 1.24 g (5.3 mmol) of 5-(2-hydroxymethyl-α-methoxybenzyl)-3-methylisoxazole and 10 ml of acetonitrile was added 1.67 g (6.36 mmol) of triphenylphosphine and 1.23 ml (12.7 mmol) of carbon tetrachloride under ice-cooling and stirred at room temperature overnight. After completion of the reaction, the residue obtained by concentration under reduced pressure was purified by column chromatography on silica gel (ethyl acetate/n-hexane) to give 5-(2-chloromethyl-α-methoxybenzyl)-3-methylisoxazole (1.03 g, 77.2%) as colorless oil.

¹H-NMR (CDCl₃) δ ppm: 2.26 (3H, s), 3.46 (3H, s), 4.63 (1H, d, J=11.9), 4.71 (1H, d, J=11.7), 5.75 (1H, s), 5.96 (1H, s), 7.32–7.53 (4H, m).

According to the same manner as that of the synthesis of the intermediate in Example 8, various compounds of the formula (XII) of this invention, which are intermediates for production of the compound (I), were synthesized. The compounds thus obtained and their physical data are shown in the following Table 5. In the following table the physical data of the compound (XII-1) obtained in Example 8 are also listed.

TABLE 5

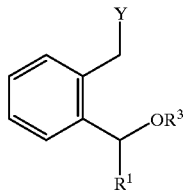

| No | R$^1$ | R$^3$ | Y | Physical data |
|---|---|---|---|---|
| XII-1 | 3-Me-5-isoxazolyl | Me | Cl | $^1$H-NMR(CDCl$_3$) δ ppm: 2.26(3H, s), 3.46(3H, s), 4.63(1H, d, J=11.9), 4.71(1H, d, J=11.7), 5.75(1H, s), 5.96(1H, s), 7.32–7.53(4H, m). |
| XII-2 | 3-isoxazolyl | Me | Cl | $^1$H-NMR(CDCl$_3$) δ ppm: 3.45(3H, s), 4.57(1H, d, J=11.6), 4.85(1H, d, J=11.6), 5.90(1H, s), 6.33(1H, d, J=1.2), 7.29–7.62(4H, m), 8.33(1H, d, J=1.8). |
| XII-3 | 5-Me-3-isoxazolyl | Me | Cl | $^1$H-NMR(CDCl$_3$) δ ppm: 2.37(3H, s), 3.43(3H, s), 4.56(1H, d, J=11.6), 4.85(1H, d, J=12.2), 5.93(1H, s), 5.79(1H, s), 7.31–7.62(4H, m). |
| XII-4 | 3-Me-5-isoxazolyl | Et | Cl | |
| XII-5 | 3,4-tetramethylene-5-isoxazolyl | Me | Cl | $^1$H-NMR(CDCl$_3$) δ ppm: 1.60–1.79(4H, m), 2.05–2.48(2H, m), 2.71(2H, t, J=6.7), 3.45(3H, s), 4.60(1H, d, J=11.6), 4.67(1H, d, J=11.6), 5.80(1H, s), 7.30–7.58(4H, m). |
| XII-6 | 4,5-tetramethylene-3-isoxazolyl | Me | Cl | $^1$H-NMR(CDCl$_3$) δ ppm: 1.61–1.86(4H, m), 2.11–2.22(1H, m), 2.38–2.48(1H, m), 2.61–2.66(2H, m), 3.45(3H, s), 4.56(1H, d, J=11.6), 4.89(1H, d, J=11.6), 5.83(1H, s), 7.28–7.41(3H, m), 7.60–7.63(1H, m). |
| XII-7 | 2-isoxazolin-3-yl | Me | Cl | $^1$H-NMR(CDCl$_3$) δ ppm: 2.64–2.79(1H, m), 2.95–3.09(1H, m), 3.43(3H, s), 4.20–4.37(2H, m), 4.53(1H, d, J=11.6), 4.87(1H, d, J=11.6), 5.60(1H, s), 7.30–7.59(4H, m). |

Example 9

Synthesis of 5-[2-(2,5-dichlorophenoxymethyl)-α-methoxybenzyl]-3-methylisoxazole (Compound No. A-31)

To 0.25 g (1 mmol) of 5-(2-chloromethyl-α-methoxybenzyl)-3-methylisoxazole, 2 ml of N,N-dimethylformamide, 0.28 g (2 mmol) of potassium carbonate and 0.33 g (2 mmol) of 2,5-dichlorophenol were added and stirred at 80° C. for 3 hours. After completion of the reaction, 100 ml of ether was added and washed twice with 80 ml of brine. The ether layer was dried over anhydrous magnesium and concentrated under reduced pressure. The residue was purified by column chromatography on silica gel (ethyl acetate/n-hexane) and recrystallized from ether/n-hexane to give 5-[2-(2,5-dichlorophenoxymethyl)-α-methoxybenzyl]-3-methylisoxazole (0.28 g, 74.0%) as colorless crystals. mp. 78.5–79.5° C.

$^1$H-NMR (CDCl$_3$) δ ppm: 2.25 (3H, s), 3.46 (3H, s), 5.12 (1H, d, J=12.2), 5.18 (1H, d, J=12.2), 5.70 (1H, s), 5.93 (1H, s), 6.89–6.95 (2H, m), 7.28–7.55 (5H, m).

Example 10

Synthesis of 5-(2-formyl-α-methoxybenzyl)-3-methylisoxazole

To 50 ml of dichloromethane containing 2.44 ml (28 mmol) of oxalyl chloride was added 2.13 ml (30 mmol) of dimethylsulfoxide dropwise below −55° C. over 3 minutes and thereafter stirred at −55 to −78° C. for 10 minutes. Then, 20 ml of dichloromethane in which 2.33 g (10 ml) of 5-(2-hydroxymethyl-α-methoxybenzyl)-3-methylisoxazole was dissolved was added dropwise below −60° C. over 8 minutes and thereafter stirred at −70 to −60° C. for 20 minutes. To the reaction solution, 7.0 ml (50 mmol) of triethylamine was added dropwise below −60° C. over 10 minutes and stirred at −70 to −10° C. for an hour.

After completion of the reaction, 300 ml of an aqueous solution of ammonium chloride was added and extracted twice with 100 ml of dichloromethane. The dichloromethane layer was dried over anhydrous magnesium and concentrated under reduced pressure. The residue was purified by column chromatography on silica gel (ethyl acetate/n-hexane) to give 5-(2-formyl-α-methoxybenzyl)-3-methylisoxazole (2.03 g, 87.8%) as oil.

$^1$H-NMR (CDCl$_3$) δ ppm: 2.25 (3H, s), 3.47 (3H, s), 5.99 (1H, s), 6.37 (1H, s), 7.55–7.87 (4H, m), 10.16 (1H, s).

Example 11

Synthesis of 5-[α-methoxy-2-{4-(4-trifluoromethylphenyl)-2,3-diaza-1,3-pentadienyl}benzyl]-3-methylisoxazole (Compound No. A-393)

To 0.23 g (1 mmol) of 5-(2-formyl-α-methoxybenzyl)-3-methylisoxazole in 2 ml of methanol was added 0.22 g (1.1 mmol) of 4'-(trifluoromethyl)acetophenone hydrazone and stirred at room temperature for 3 hours. After completion of the reaction, methanol was concentrated under reduced pressure. The residue was purified by column chromatography on silica gel (ethyl acetate/n-hexane) to give 5-[α-methoxy-2-{4-(4-trifluoromethylphenyl)-2,3-diaza-1,3-pentadienyl}benzyl]-3-methylisoxazole (0.23 g, 55.4%) as oil.

$^1$H-NMR (CDCl$_3$) δ ppm: 2.23 (3H, s), 2.44 (3H, s), 3.49 (3H, s), 5.81 (1H, s), 6.26 (1H, s), 7.43–8.02 (8H, m), 8.67(1H, s).

Example 12

Synthesis of 5-(2-hydroxyiminomethyl-α-methoxybenzyl)-3-methylisoxazole

To 1.39 g (6 mmol) of 5-(2-formyl-α-methoxybenzyl)-3-methylisoxazole in 12 ml of methanol was added 0.83 g (12 mmol) of hydroxylamine hydrochloride and 1.07 ml (13.2 mmol) of pyridine and stirred under reflux for 2 hours. After completion of the reaction, 200 ml of 0.1 N hydrochloric acid was added and extracted twice with 100 ml of dichloromethane. The dichloromethane layer was dried over anhydrous magnesium and concentrated under reduced pressure. The residue was purified by column chromatography on silica gel (ethyl acetate/n-hexane) to give 5-(2-hydroxyiminomethyl-α-methoxybenzyl)-3-methylisoxazole (1.20 g, 81.2%) as oil.

$^1$H-NMR (CDCl$_3$) δ ppm: 2.25 (3H, s), 3.44 (3H, s), 5.85 (2H, s), 7.38–7.47 (2H, m), 7.52 (1H, s), 7.56–7.67 (2H, m), 8.41 (1H, 5).

Example 13

Synthesis of 5-[α-methoxy-2-(4-phenyl-2-aza-3-oxa-1-pentenyl)benzyl]-3-methylisoxazole (Compound No. A-361)

To a mixture of 0.25 g (1 mmol) of 5-(2-hydroxyiminomethyl-α-methoxybenzyl)-3-methylisoxazole, 3 ml of N,N-dimethylformamide and 0.24 g (1.3 mmol) of α-methylbenzyl bromide was added 0.05 g (1.3 mmol) of 60% sodium hydride under ice-cooling and stirred at the same temperature for 3 hours. After completion of the reaction, 100 ml of ether was added and washed twice with 80 ml of brine. The ether layer was dried over anhydrous magnesium and concentrated under reduced pressure. The residue was purified by column chromatography on silica gel (ethyl acetate/n-hexane) to give 5-[α-methoxy-2-(4-phenyl-2-aza-3-oxa-1-pentenyl)benzyl]-3-methylisoxazole (0.32 g, 91.3%) as colorless oil.

$^1$H-NMR (CDCl$_3$) δ ppm: 1.56 (1.61) (3H, d, J=6.7), 2.16 (2.23) (3H, s), 3.27 (3.39) (3H, s), 5.26–5.35 (1H, m), 5.57 (5.69) (1H, s), 5.79 (5.91) (1H, s), 7.27–7.63 (9H, m), 8.30 (8.35) (1H, s).

Example 14

Synthesis of 2-(4-chloro-2-methylphenoxymethyl)phenyl-2-methoxyacetic acid hydrazide To 1.05 g (3 mmol) of ethyl 2-(4-chloro-2-methylphenoxymethyl)phenyl-2-methoxyacetate was added 6 ml of methanol and 0.75 g (15 mmol) of hydrazine monohydrate and stirred at 60° C. for 16 hours. After completion of the reaction, 100 ml of brine was added and extracted twice with 70 ml of dichloromethane. The extract was dried over anhydrous magnesium and concentrated under reduced pressure to give 2-(4-chloro-2-methylphenoxymethyl)phenyl-2-methoxyacetic acid hydrazide (0.93 g, 92.6%) as colorless oil.

$^1$H-NMR (CDCl$_3$) δ ppm: 2.22 (3H, s), 3.35 (3H, s), 3.80 (2H, d, J=3.7), 5.07 (1H, s), 5.08 (1H, d, J=11.6), 5.42 (1H, d, J=11.6), 6.86 (1H, d, J=9.2), 7.09–7.13 (2H, m), 7.33–7.51 (4H, m), 7.87 (1H, brs).

Example 15

Synthesis of 2-[2-(4-chloro-2-methylphenoxymethyl)-α-methoxybenzyl]-1,3,4-oxadiazole (Compound No. L-41)

To 0.50 g (1.5 mmol) of 2-(4-chloro-2-methylphenoxymethyl)phenyl-2-methoxyacetic acid hydrazide was added 1.5 ml of ethyl orthoformate, stirred under reflux for 3 hours, and thereafter concentrated under reduced pressure. To the residue thus obtained, 4.5 ml of benzene and 0.03 g (0.15 mmol) of p-toluenesulfonic acid monohydrate were added and stirred under reflux for an hour. After completion of the reaction, 100 ml of water was added and extracted twice with 50 ml of dichloromethane. The dichloromethane layer was dried over anhydrous magnesium and concentrated under reduced pressure. The residue was purified by column chromatography on silica gel (ethyl acetate/n-hexane) to give 2-[2-(4-chloro-2-methylphenoxymethyl)-α-methoxybenzyl]-1,3,4-oxadiazole (0.07 g, 13.5%) as colorless crystals. mp. 68–70° C.

$^1$H-NMR (CDCl$_3$) δ ppm: 2.17 (3H, s), 3.47 (3H, s), 5.05 (1H, d, J=12.2), 5.19 (1H, d, J=12.2), 5.94 (1H, s), 6.83 (1H, dd, J=7.3, 1.8), 7.10–7.13 (2H, m), 7.40–7.71 (4H, m), 8.36 (1H, s).

Examples of the compounds represented by the formula (I) obtainable by the same manner as that in Examples described above are the following compound groups A to O. Examples of combination of the substituents $R^2$, $R^3$, $R^4$, M, and n of the compound groups A to O are shown in Tables 6 to 30. The physical data of the compounds are shown in Tables 31 to 41. The physical data of the compounds obtained in the above Examples are also listed. "No." represents a compound number.

A

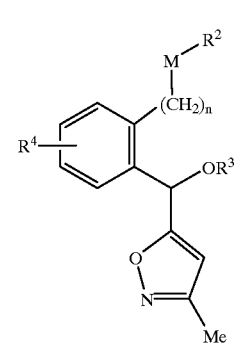

B

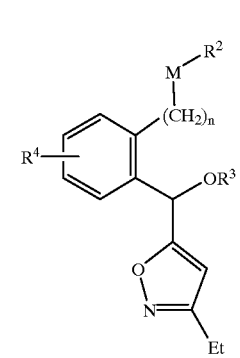

C

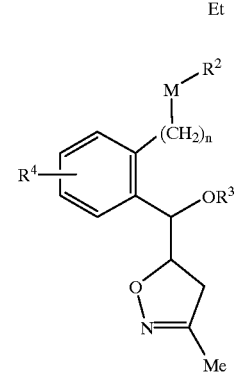

-continued
D
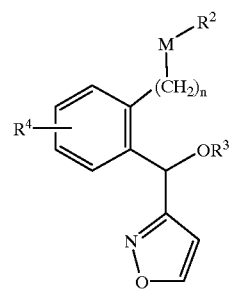
E
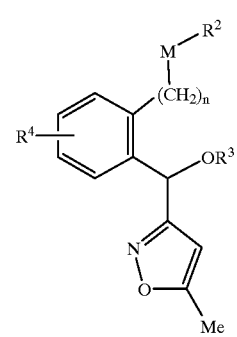
F
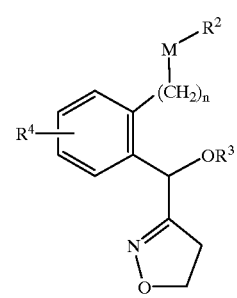
G
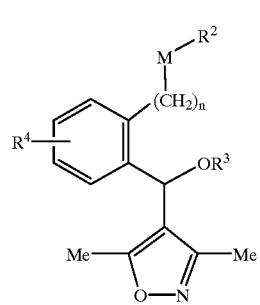
H
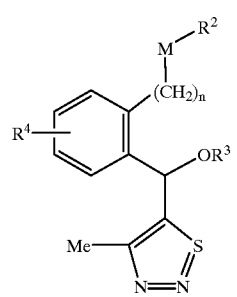
-continued
I
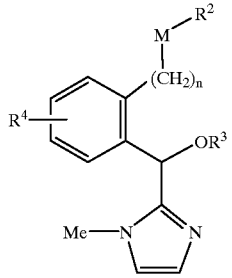
J
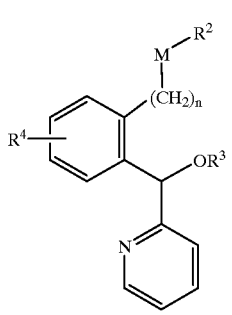
K
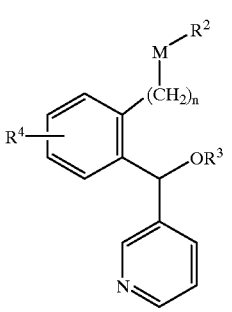
L
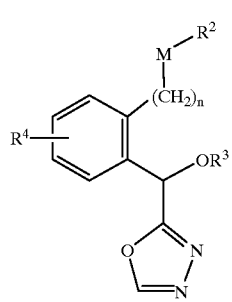
M
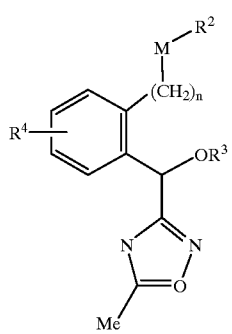

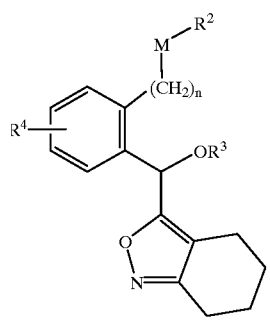

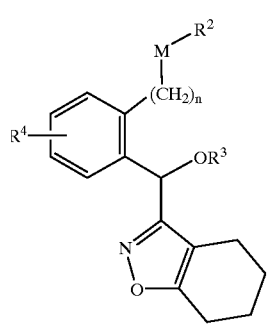

TABLE 6

| No | R² | R³ | R⁴ | M | n |
|---|---|---|---|---|---|
| 1 | C₆H₅ | Me | H | O | 1 |
| 2 | 2-F—C₆H₄ | Me | H | O | 1 |
| 3 | 3-F—C₆H₄ | Me | H | O | 1 |
| 4 | 4-F—C₆H₄ | Me | H | O | 1 |
| 5 | 2-Cl—C₆H₄ | Me | H | O | 1 |
| 6 | 3-Cl—C₆H₄ | Me | H | O | 1 |
| 7 | 4-Cl—C₆H₄ | Me | H | O | 1 |
| 8 | 2-Br—C₆H₄ | Me | H | O | 1 |
| 9 | 3-Br—C₆H₄ | Me | H | O | 1 |
| 10 | 4-Br—C₆H₄ | Me | H | O | 1 |
| 11 | 3-I—C₆H₄ | Me | H | O | 1 |
| 12 | 2-Me—C₆H₄ | Me | H | O | 1 |
| 13 | 3-Me—C₆H₄ | Me | H | O | 1 |
| 14 | 4-Me—C₆H₄ | Me | H | O | 1 |
| 15 | 2-Et—C₆H₄ | Me | H | O | 1 |
| 16 | 3-Et—C₆H₄ | Me | H | O | 1 |
| 17 | 4-Et—C₆H₄ | Me | H | O | 1 |
| 18 | 2-MeO—C₆H₄ | Me | H | O | 1 |
| 19 | 3-MeO—C₆H₄ | Me | H | O | 1 |
| 20 | 4-MeO—C₆H₄ | Me | H | O | 1 |

TABLE 7

| No | R² | R³ | R⁴ | M | n |
|---|---|---|---|---|---|
| 21 | 2-CF₃—C₆H₄ | Me | H | O | 1 |
| 22 | 3-CF₃—C₆H₄ | Me | H | O | 1 |
| 23 | 4-CF₃—C₆H₄ | Me | H | O | 1 |
| 24 | 2,4-F₂—C₆H₃ | Me | H | O | 1 |
| 25 | 2,5-F₂—C₆H₃ | Me | H | O | 1 |
| 26 | 2,6-F₂—C₆H₃ | Me | H | O | 1 |
| 27 | 3,4-F₂—C₆H₃ | Me | H | O | 1 |
| 28 | 3,5-F₂—C₆H₃ | Me | H | O | 1 |
| 29 | 2,3-Cl₂—C₆H₃ | Me | H | O | 1 |
| 30 | 2,4-Cl₂—C₆H₃ | Me | H | O | 1 |
| 31 | 2,5-Cl₂—C₆H₃ | Me | H | O | 1 |
| 32 | 3,4-Cl₂—C₆H₃ | Me | H | O | 1 |

TABLE 7-continued

| No | R² | R³ | R⁴ | M | n |
|---|---|---|---|---|---|
| 33 | 3,5-Cl₂—C₆H₃ | Me | H | O | 1 |
| 34 | 2,3-Me₂—C₆H₃ | Me | H | O | 1 |
| 35 | 2,4-Me₂—C₆H₃ | Me | H | O | 1 |
| 36 | 2,5-Me₂—C₆H₃ | Me | H | O | 1 |
| 37 | 3,4-Me₂—C₆H₃ | Me | H | O | 1 |
| 38 | 3,5-Me₂—C₆H₃ | Me | H | O | 1 |
| 39 | 2-Cl-4-Me—C₆H₃ | Me | H | O | 1 |
| 40 | 2-Cl-5-Me—C₆H₃ | Me | H | O | 1 |

TABLE 8

| No | R² | R³ | R⁴ | M | n |
|---|---|---|---|---|---|
| 41 | 4-Cl-2-Me—C₆H₃ | Me | H | O | 1 |
| 42 | 4-Cl-3-Me—C₆H₃ | Me | H | O | 1 |
| 43 | 3-Ph—C₆H₄ | Me | H | O | 1 |
| 44 | 4-Ph—C₆H₄ | Me | H | O | 1 |
| 45 | 3-i-PrO—C₆H₄ | Me | H | O | 1 |
| 46 | 3-i-Pr—C₆H₄ | Me | H | O | 1 |
| 47 | 4-i-Pr—C₆H₄ | Me | H | O | 1 |
| 48 | 3-t-Bu—C₆H₄ | Me | H | O | 1 |
| 49 | 2-MeS—C₆H₄ | Me | H | O | 1 |
| 50 | 4-MeS—C₆H₄ | Me | H | O | 1 |
| 51 | 2,3,6-F₃—C₆H₂ | Me | H | O | 1 |
| 52 | 2,4,5-Cl₃—C₆H₂ | Me | H | O | 1 |
| 53 | 4-PhO—C₆H₄ | Me | H | O | 1 |
| 54 | 3,4,5-(MeO)₃—C₆H₂ | Me | H | O | 1 |
| 55 | 2,3,5-Me₃—C₆H₂ | Me | H | O | 1 |
| 56 | 3,4,5-Me₃—C₆H₂ | Me | H | O | 1 |
| 57 | C₆F₅ | Me | H | O | 1 |
| 58 | 4-Cl-3-Et—C₆H₃ | Me | H | O | 1 |
| 59 | 3-EtO—C₆H₄ | Me | H | O | 1 |
| 60 | 4-EtO—C₆H₄ | Me | H | O | 1 |

TABLE 9

| No | R² | R³ | R⁴ | M | n |
|---|---|---|---|---|---|
| 61 | 2-pryidyl | Me | H | O | 1 |
| 62 | 5-Cl-2-pyridyl | Me | H | O | 1 |
| 63 | 3-Cl-2-pyridyl | Me | H | O | 1 |
| 64 | 6-Cl-2-pyridyl | Me | H | O | 1 |
| 65 | 3,5-Cl₂-2-pyridyl | Me | H | O | 1 |
| 66 | 5-CF₃-2-pyridyl | Me | H | O | 1 |
| 67 | 3-CF₃-2-pyridyl | Me | H | O | 1 |
| 68 | 3-CF₃-5-Cl-2-pyridyl | Me | H | O | 1 |
| 69 | 5-CF₃-3-Cl-2-pyridyl | Me | H | O | 1 |
| 70 | 2-benzothiazolyl | Me | H | O | 1 |
| 71 | 2-benzoxazolyl | Me | H | O | 1 |
| 72 | 2-quinolyl | Me | H | O | 1 |
| 73 | 5-CF₃-1,3,4-thiadiazol-2-yl | Me | H | O | 1 |
| 74 | 2-pyrimidyl | Me | H | O | 1 |
| 75 | 6-Cl-4-pyrimidyl | Me | H | O | 1 |
| 76 | 6-Cl-2-benzothiazolyl | Me | H | O | 1 |
| 77 | 6-Cl-2-pyrazinyl | Me | H | O | 1 |
| 78 | 3,6-Me₂-2-pyrazinyl | Me | H | O | 1 |
| 79 | 3-Ph-5-isoxazolyl | Me | H | O | 1 |
| 80 | 5-Me-3-isoxazolyl | Me | H | O | 1 |

TABLE 10

| No | R² | R³ | R⁴ | M | n |
|---|---|---|---|---|---|
| 81 | C₆H₅ | Me | H | —ON=C(Me)— | 1 |
| 82 | 2-F—C₆H₄ | Me | H | —ON=C(Me)— | 1 |
| 83 | 3-F—C₆H₄ | Me | H | —ON=C(Me)— | 1 |
| 84 | 4-F—C₆H₄ | Me | H | —ON=C(Me)— | 1 |
| 85 | 2-Cl—C₆H₄ | Me | H | —ON=C(Me)— | 1 |
| 86 | 3-Cl—C₆H₄ | Me | H | —ON=C(Me)— | 1 |
| 87 | 4-Cl—C₆H₄ | Me | H | —ON=C(Me)— | 1 |

TABLE 10-continued

| No | R² | R³ | R⁴ | M | n |
|---|---|---|---|---|---|
| 88 | 2-Br—C₆H₄ | Me | H | —ON=C(Me)— | 1 |
| 89 | 3-Br—C₆H₄ | Me | H | —ON=C(Me)— | 1 |
| 90 | 4-Br—C₆H₄ | Me | H | —ON=C(Me)— | 1 |
| 91 | 3-I—C₆H₄ | Me | H | —ON=C(Me)— | 1 |
| 92 | 2-Me—C₆H₄ | Me | H | —ON=C(Me)— | 1 |
| 93 | 3-Me—C₆H₄ | Me | H | —ON=C(Me)— | 1 |
| 94 | 4-Me—C₆H₄ | Me | H | —ON=C(Me)— | 1 |
| 95 | 2-Et—C₆H₄ | Me | H | —ON=C(Me)— | 1 |
| 96 | 3-Et—C₆H₄ | Me | H | —ON=C(Me)— | 1 |
| 97 | 4-Et—C₆H₄ | Me | H | —ON=C(Me)— | 1 |
| 98 | 2-MeO—C₆H₄ | Me | H | —ON=C(Me)— | 1 |
| 99 | 3-MeO—C₆H₄ | Me | H | —ON=C(Me)— | 1 |
| 100 | 4-MeO—C₆H₄ | Me | H | —ON=C(Me)— | 1 |

TABLE 11

| No | R² | R³ | R⁴ | M | n |
|---|---|---|---|---|---|
| 101 | 2-CF₃—C₆H₄ | Me | H | —ON=C(Me)— | 1 |
| 102 | 3-CF₃—C₆H₄ | Me | H | —ON=C(Me)— | 1 |
| 103 | 4-CF₃—C₆H₄ | Me | H | —ON=C(Me)— | 1 |
| 104 | 2,4-F₂—C₆H₃ | Me | H | —ON=C(Me)— | 1 |
| 105 | 2,5-F₂—C₆H₃ | Me | H | —ON=C(Me)— | 1 |
| 106 | 3,5-F₂—C₆H₃ | Me | H | —ON=C(Me)— | 1 |
| 107 | 2,3-Cl₂—C₆H₃ | Me | H | —ON=C(Me)— | 1 |
| 108 | 2,4-Cl₂—C₆H₃ | Me | H | —ON=C(Me)— | 1 |
| 109 | 2,5-Cl₂—C₆H₃ | Me | H | —ON=C(Me)— | 1 |
| 110 | 3,4-Cl₂—C₆H₃ | Me | H | —ON=C(Me)— | 1 |
| 111 | 3,5-Cl₂—C₆H₃ | Me | H | —ON=C(Me)— | 1 |
| 112 | 2,3-Me₂—C₆H₃ | Me | H | —ON=C(Me)— | 1 |
| 113 | 2,4-Me₂—C₆H₃ | Me | H | —ON=C(Me)— | 1 |
| 114 | 2,5-Me₂—C₆H₃ | Me | H | —ON=C(Me)— | 1 |
| 115 | 3,4-Me₂—C₆H₃ | Me | H | —ON=C(Me)— | 1 |
| 116 | 3,5-Me₂—C₆H₃ | Me | H | —ON=C(Me)— | 1 |
| 117 | 3-Cl-4-Me—C₆H₃ | Me | H | —ON=C(Me)— | 1 |
| 118 | 3-Cl-5-Me—C₆H₃ | Me | H | —ON=C(Me)— | 1 |
| 119 | 4-Cl-3-Me—C₆H₃ | Me | H | —ON=C(Me)— | 1 |
| 120 | 3,4,5-Me₃—C₆H₂ | Me | H | —ON=C(Me)— | 1 |

TABLE 12

| No | R² | R³ | R⁴ | M | n |
|---|---|---|---|---|---|
| 121 | 3-Ph—C₆H₄ | Me | H | —ON=C(Me)— | 1 |
| 122 | 4-Ph—C₆H₄ | Me | H | —ON=C(Me)— | 1 |
| 123 | 4-PhO—C₆H₄ | Me | H | —ON=C(Me)— | 1 |
| 124 | 3-i-PrO—C₆H₄ | Me | H | —ON=C(Me)— | 1 |
| 125 | 2-pyridyl | Me | H | —ON=C(Me)— | 1 |
| 126 | 3-pyridyl | Me | H | —ON=C(Me)— | 1 |
| 127 | 4-pyridyl | Me | H | —ON=C(Me)— | 1 |
| 125 | 2-furyl | Me | H | —ON=C(Me)— | 1 |
| 129 | 3-furyl | Me | H | —ON=C(Me)— | 1 |
| 130 | 2-thienyl | Me | H | —ON=C(Me)— | 1 |
| 131 | 3-thienyl | Me | H | —ON=C(Me)— | 1 |
| 132 | 2-naphthyl | Me | H | —ON=C(Me)— | 1 |
| 133 | 3-naphthyl | Me | H | —ON=C(Me)— | 1 |
| 134 | 2-thiazolyl | Me | H | —ON=C(Me)— | 1 |
| 135 | 2-pyrazinyl | Me | H | —ON=C(Me)— | 1 |
| 136 | 5-Me-2-furyl | Me | H | —ON=C(Me)— | 1 |
| 137 | 5-Cl-2-thienyl | Me | H | —ON=C(Me)— | 1 |
| 138 | 5-Br-2-thienyl | Me | H | —ON=C(Me)— | 1 |
| 139 | 3-Ph-5-isoxazolyl | Me | H | —ON=C(Me)— | 1 |
| 140 | 5-Me-3-isoxazolyl | Me | H | —ON=C(Me)— | 1 |

TABLE 13

| No | R² | R³ | R⁴ | M | n |
|---|---|---|---|---|---|
| 141 | C₆H₅ | Me | H | —ON=C(SMe)— | 1 |
| 142 | 2-F—C₆H₄ | Me | H | —ON=C(SMe)— | 1 |

TABLE 13-continued

| No | R² | R³ | R⁴ | M | n |
|---|---|---|---|---|---|
| 143 | 3-F—C₆H₄ | Me | H | —ON=C(SMe)— | 1 |
| 144 | 4-F—C₆H₄ | Me | H | —ON=C(SMe)— | 1 |
| 145 | 2-Cl—C₆H₄ | Me | H | —ON=C(SMe)— | 1 |
| 146 | 3-Cl—C₆H₄ | Me | H | —ON=C(SMe)— | 1 |
| 147 | 4-Cl—C₆H₄ | Me | H | —ON=C(SMe)— | 1 |
| 148 | 2-Br—C₆H₄ | Me | H | —ON=C(SMe)— | 1 |
| 149 | 3-Br—C₆H₄ | Me | H | —ON=C(SMe)— | 1 |
| 150 | 4-Br—C₆H₄ | Me | H | —ON=C(SMe)— | 1 |
| 151 | 3-I—C₆H₄ | Me | H | —ON=C(SMe)— | 1 |
| 152 | 2-Me—C₆H₄ | Me | H | —ON=C(SMe)— | 1 |
| 153 | 3-Me—C₆H₄ | Me | H | —ON=C(SMe)— | 1 |
| 154 | 4-Me—C₆H₄ | Me | H | —ON=C(SMe)— | 1 |
| 155 | 2-Et—C₆H₄ | Me | H | —ON=C(SMe)— | 1 |
| 156 | 3-Et—C₆H₄ | Me | H | —ON=C(SMe)— | 1 |
| 157 | 4-Et—C₆H₄ | Me | H | —ON=C(SMe)— | 1 |
| 158 | 2-MeO—C₆H₄ | Me | H | —ON=C(SMe)— | 1 |
| 159 | 3-MeO—C₆H₄ | Me | H | —ON=C(SMe)— | 1 |
| 160 | 4-MeO—C₆H₄ | Me | H | —ON=C(SMe)— | 1 |

TABLE 14

| No | R₂ | R₃ | R₄ | M | n |
|---|---|---|---|---|---|
| 161 | 2-CF₃—C₆H₄ | Me | H | —ON=C(SMe)— | 1 |
| 162 | 3-CF₃—C₆H₄ | Me | H | —ON=C(SMe)— | 1 |
| 163 | 4-CF₃—C₆H₄ | Me | H | —ON=C(SMe)— | 1 |
| 164 | 2,4-F₂—C₆H₃ | Me | H | —ON=C(SMe)— | 1 |
| 165 | 2,5-F₂—C₆H₃ | Me | H | —ON=C(SMe)— | 1 |
| 166 | 3,5-F₂—C₆H₃ | Me | H | —ON=C(SMe)— | 1 |
| 167 | 2,3-Cl₂—C₆H₃ | Me | H | —ON=C(SMe)— | 1 |
| 168 | 2,4-Cl₂—C₆H₃ | Me | H | —ON=C(SMe)— | 1 |
| 169 | 2,5-Cl₂—C₆H₃ | Me | H | —ON=C(SMe)— | 1 |
| 170 | 3,4-Cl₂—C₆H₃ | Me | H | —ON=C(SMe)— | 1 |
| 171 | 3,5-Cl₂—C₆H₃ | Me | H | —ON=C(SMe)— | 1 |
| 172 | 2,3-Me₂—C₆H₃ | Me | H | —ON=C(SMe)— | 1 |
| 173 | 2,4-Me₂—C₆H₃ | Me | H | —ON=C(SMe)— | 1 |
| 174 | 2,5-Me₂—C₆H₃ | Me | H | —ON=C(SMe)— | 1 |
| 175 | 3,4-Me₂—C₆H₃ | Me | H | —ON=C(SMe)— | 1 |
| 176 | 3,5-Me₂—C₆H₃ | Me | H | —ON=C(SMe)— | 1 |
| 177 | 3-Cl-4-Me—C₆H₃ | Me | H | —ON=C(SMe)— | 1 |
| 178 | 3-Cl-5-Me—C₆H₃ | Me | H | —ON=C(SMe)— | 1 |
| 179 | 4-Cl-3-Me—C₆H₃ | Me | H | —ON=C(SMe)— | 1 |
| 180 | 3,4,5-Me₃—C₆H₂ | Me | H | —ON=C(SMe)— | 1 |

TABLE 15

| No | R² | R³ | R⁴ | M | n |
|---|---|---|---|---|---|
| 181 | 3-Ph—C₆H₄ | Me | H | —ON=C(SMe)— | 1 |
| 182 | 4-Ph—C₆H₄ | Me | H | —ON=C(SMe)— | 1 |
| 183 | 4-PhO—C₆H₄ | Me | H | —ON=C(SMe)— | 1 |
| 184 | 3-i-PrO—C₆H₄ | Me | H | —ON=C(SMe)— | 1 |
| 185 | 2-pyridyl | Me | H | —ON=C(SMe)— | 1 |
| 186 | 3-pyridyl | Me | H | —ON=C(SMe)— | 1 |
| 187 | 4-pyridyl | Me | H | —ON=C(SMe)— | 1 |
| 188 | 2-furyl | Me | H | —ON=C(SMe)— | 1 |
| 189 | 3-furyl | Me | H | —ON=C(SMe)— | 1 |
| 190 | 2-thienyl | Me | H | —ON=C(SMe)— | 1 |
| 191 | 3-thienyl | Me | H | —ON=C(SMe)— | 1 |
| 192 | 2-naphthyl | Me | H | —ON=C(SMe)— | 1 |
| 193 | 3-naphthyl | Me | H | —ON=C(SMe)— | 1 |
| 194 | 2-thiazolyl | Me | H | —ON=C(SMe)— | 1 |
| 195 | 2-pyrazinyl | Me | H | —ON=C(SMe)— | 1 |
| 196 | 5-Me-2-furyl | Me | H | —ON=C(SMe)— | 1 |
| 197 | 5-Cl-2-thienyl | Me | H | —ON=C(SMe)— | 1 |
| 198 | 5-Br-2-thienyl | Me | H | —ON=C(SMe)— | 1 |
| 199 | 3-Ph-5-isoxazolyl | Me | H | —ON=C(SMe)— | 1 |
| 200 | 5-Me-3-isoxazolyl | Me | H | —ON=C(SMe)— | 1 |

TABLE 16

| No | R² | R³ | R⁴ | M | n |
|---|---|---|---|---|---|
| 201 | C₆H₅ | Me | H | —ON=C(Et)— | 1 |
| 202 | 4-F—C₆H₄ | Me | H | —ON=C(Et)— | 1 |
| 203 | 3-F—C₆H₄ | Me | H | —ON=C(Et)— | 1 |
| 204 | 3-Cl—C₆H₄ | Me | H | —ON=C(Et)— | 1 |
| 205 | 4-Cl—C₆H₄ | Me | H | —ON=C(Et)— | 1 |
| 206 | 4-Br—C₆H₄ | Me | H | —ON=C(Et)— | 1 |
| 207 | 3-Me—C₆H₄ | Me | H | —ON=C(Et)— | 1 |
| 208 | 4-Me—C₆H₄ | Me | H | —ON=C(Et)— | 1 |
| 209 | 4-Et—C₆H₄ | Me | H | —ON=C(Et)— | 1 |
| 210 | 3-MeO—C₆H₄ | Me | H | —ON=C(Et)— | 1 |
| 211 | 4-MeO—C₆H₄ | Me | H | —ON=C(Et)— | 1 |
| 212 | 3-CF₃—C₆H₄ | Me | H | —ON=C(Et)— | 1 |
| 213 | 4-CF₃—C₆H₄ | Me | H | —ON=C(Et)— | 1 |
| 214 | 3,4-F₂—C₆H₃ | Me | H | —ON=C(Et)— | 1 |
| 215 | 3,5-F₂—C₆H₃ | Me | H | —ON=C(Et)— | 1 |
| 216 | 3,4-Cl₂—C₆H₃ | Me | H | —ON=C(Et)— | 1 |
| 217 | 3,5-Cl₂—C₆H₃ | Me | H | —ON=C(Et)— | 1 |
| 218 | 3,4-Me₂—C₆H₃ | Me | H | —ON=C(Et)— | 1 |
| 219 | 4-Cl-3-Me—C₆H₃ | Me | H | —ON=C(Et)— | 1 |
| 220 | 3-Ph—C₆H₄ | Me | H | —ON=C(Et)— | 1 |

TABLE 17

| No | R² | R³ | R⁴ | M | n |
|---|---|---|---|---|---|
| 221 | C₆H₅ | Me | H | —ON=C(SEt)— | 1 |
| 222 | 4-F—C₆H₄ | Me | H | —ON=C(SEt)— | 1 |
| 223 | 3-F—C₆H₄ | Me | H | —ON=C(SEt)— | 1 |
| 224 | 3-Cl—C₆H₄ | Me | H | —ON=C(SEt)— | 1 |
| 225 | 4-Cl—C₆H₄ | Me | H | —ON=C(SEt)— | 1 |
| 226 | 4-Br—C₆H₄ | Me | H | —ON=C(SEt)— | 1 |
| 227 | 3-Me—C₆H₄ | Me | H | —ON=C(SEt)— | 1 |
| 228 | 4-Me—C₆H₄ | Me | H | —ON=C(SEt)— | 1 |
| 229 | 4-Et—C₆H₄ | Me | H | —ON=C(SEt)— | 1 |
| 230 | 3-MeO—C₆H₄ | Me | H | —ON=C(SEt)— | 1 |
| 231 | 4-MeO—C₆H₄ | Me | H | —ON=C(SEt)— | 1 |
| 232 | 3-CF₃—C₆H₄ | Me | H | —ON=C(SEt)— | 1 |
| 233 | 4-CF₃—C₆H₄ | Me | H | —ON=C(SEt)— | 1 |
| 234 | 3,4-F₂—C₆H₃ | Me | H | —ON=C(SEt)— | 1 |
| 235 | 3,5-F₂—C₆H₃ | Me | H | —ON=C(SEt)— | 1 |
| 236 | 3,4-Cl₂—C₆H₃ | Me | H | —ON=C(SEt)— | 1 |
| 237 | 3,5-Cl₂—C₆H₃ | Me | H | —ON=C(SEt)— | 1 |
| 238 | 3,4-Me₂—C₆H₃ | Me | H | —ON=C(SEt)— | 1 |
| 239 | 4-Cl-3-Me—C₆H₃ | Me | H | —ON=C(SEt)— | 1 |
| 240 | 3-Ph—C₆H₄ | Me | H | —ON=C(SEt)— | 1 |

TABLE 18

| No | R² | R³ | R⁴ | M | n |
|---|---|---|---|---|---|
| 241 | C₆H₅ | Me | H | O | 0 |
| 242 | 4-F—C₆H₄ | Me | H | O | 0 |
| 243 | 3-F—C₆H₄ | Me | H | O | 0 |
| 244 | 3-Cl—C₆H₄ | Me | H | O | 0 |
| 245 | 4-Cl—C₆H₄ | Me | H | O | 0 |
| 246 | 4-Br—C₆H₄ | Me | H | O | 0 |
| 247 | 3-Me—C₆H₄ | Me | H | O | 0 |
| 248 | 4-Me—C₆H₄ | Me | H | O | 0 |
| 249 | 3-CF₃—C₆H₄ | Me | H | O | 0 |
| 250 | 4-CF₃—C₆H₄ | Me | H | O | 0 |
| 251 | 3,4-F₂—C₆H₃ | Me | H | O | 0 |
| 252 | 3,5-F₂—C₆H₃ | Me | H | O | 0 |
| 253 | 3,4-Cl₂—C₆H₃ | Me | H | O | 0 |
| 254 | 3,5-Cl₂—C₆H₃ | Me | H | O | 0 |
| 255 | 3,4-Me₂—C₆H₃ | Me | H | O | 0 |
| 256 | 4-Cl-3-Me—C₆H₃ | Me | H | O | 0 |
| 257 | 5-CF₃-2-pyridyl | Me | H | O | 0 |
| 258 | 5-CF₃-3-Cl2-2-pyridyl | Me | H | O | 0 |
| 259 | 3,5-Cl₂-2-pyridyl | Me | H | O | 0 |
| 260 | 6-(2-CN—C6H4O)-4-pyrimidyl | Me | H | O | 0 |

TABLE 19

| No | R² | R³ | R⁴ | M | n |
|---|---|---|---|---|---|
| 261 | C₆H₅ | Me | H | —N(Ac)N=C(Me)— | 1 |
| 262 | 4-F—C₆H₄ | Me | H | —N(Ac)N=C(Me)— | 1 |
| 263 | 3-F—C₆H₄ | Me | H | —N(Ac)N=C(Me)— | 1 |
| 264 | 3-Cl—C₆H₄ | Me | H | —N(Ac)N=C(Me)— | 1 |
| 265 | 4-Cl—C₆H₄ | Me | H | —N(Ac)N=C(Me)— | 1 |
| 266 | 4-Br—C₆H₄ | Me | H | —N(Ac)N=C(Me)— | 1 |
| 267 | 3-Me—C₆H₄ | Me | H | —N(Ac)N=C(Me)— | 1 |
| 268 | 4-Me—C₆H₄ | Me | H | —N(Ac)N=C(Me)— | 1 |
| 269 | 4-Et—C₆H₄ | Me | H | —N(Ac)N=C(Me)— | 1 |
| 270 | 3-MeO—C₆H₄ | Me | H | —N(Ac)N=C(Me)— | 1 |
| 271 | 4-MeO—C₆H₄ | Me | H | —N(Ac)N=C(Me)— | 1 |
| 272 | 3-CF₃—C₆H₄ | Me | H | —N(Ac)N=C(Me)— | 1 |
| 273 | 4-CF₃—C₆H₄ | Me | H | —N(Ac)N=C(Me)— | 1 |
| 274 | 3,4-F₂—C₆H₃ | Me | H | —N(Ac)N=C(Me)— | 1 |
| 275 | 3,5-F₂—C₆H₃ | Me | H | —N(Ac)N=C(Me)— | 1 |
| 276 | 3,4-Cl₂—C₆H₃ | Me | H | —N(Ac)N=C(Me)— | 1 |
| 277 | 3,5-Cl₂—C₆H₃ | Me | H | —N(Ac)N=C(ME)— | 1 |
| 278 | 3,4-Me₂—C₆H₃ | Me | H | —N(Ac)N=C(Me)— | 1 |
| 279 | 4-Cl-3-Me—C₆H₃ | Me | H | —N(Ac)N=C(Me)— | 1 |
| 280 | 3-Ph—C₆H₄ | Me | H | —N(Ac)N=C(Me)— | 1 |
| 281 | C₆H₅ | Me | H | —ON=C(CN)— | 1 |

TABLE 20

| No | R² | R³ | R⁴ | M | n |
|---|---|---|---|---|---|
| 282 | 4-F—C₆H₄ | Me | H | —ON=C(CN)— | 1 |
| 283 | 3-F—C₆H₄ | Me | H | —ON=C(CN)— | 1 |
| 284 | 3-Cl—C₆H₄ | Me | H | —ON=C(CN)— | 1 |
| 285 | 4-Cl—C₆H₄ | Me | H | —ON=C(CN)— | 1 |
| 286 | 4-Br—C₆H₄ | Me | H | —ON=C(CN)— | 1 |
| 287 | 3-Me—C₆H₄ | Me | H | —ON=C(CN)— | 1 |
| 288 | 4-Me—C₆H₄ | Me | H | —ON=C(CN)— | 1 |
| 289 | 4-Et—C₆H₄ | Me | H | —ON=C(CN)— | 1 |
| 290 | 3-MeO—C₆H₄ | Me | H | —ON=C(CN)— | 1 |
| 291 | 4-MeO—C₆H₄ | Me | H | —ON=C(CN)— | 1 |
| 292 | 3-CF₃—C₆H₄ | Me | H | —ON=C(CN)— | 1 |
| 293 | 4-CF₃—C₆H₄ | Me | H | —ON=C(CN)— | 1 |
| 294 | 3,4-F₂—C₆H₃ | Me | H | —ON=C(CN)— | 1 |
| 295 | 3,5-F₂—C₆H₃ | Me | H | —ON=C(CN)— | 1 |
| 296 | 3,4-Cl₂—C₆H₃ | Me | H | —ON=C(CN)— | 1 |
| 297 | 3,5-Cl₂—C₆H₃ | Me | H | —ON=C(CN)— | 1 |
| 298 | 3,4-Me₂—C₆H₃ | Me | H | —ON=C(CN)— | 1 |
| 299 | 4-Cl-3-Me—C₆H₃ | Me | H | —ON=C(CN)— | 1 |
| 300 | 3-Ph—C₆H₄ | Me | H | —ON=C(CN)— | 1 |
| 301 | C₆H₅ | Me | H | —ON=C(CF₃)— | 1 |
| 302 | 4-F—C₆H₄ | Me | H | —ON=C(CF₃)— | 1 |

TABLE 21

| No | R² | R³ | R⁴ | M | n |
|---|---|---|---|---|---|
| 303 | 3-F—C₆H₄ | Me | H | —ON=C(CF₃)— | 1 |
| 304 | 3-Cl—C₆H₄ | Me | H | —ON=C(CF₃)— | 1 |
| 305 | 4-Cl—C₆H₄ | Me | H | —ON=C(CF₃)— | 1 |
| 306 | 4-Br—C₆H₄ | Me | H | —ON=C(CF₃)— | 1 |
| 307 | 3-Me—C₆H₄ | Me | H | —ON=C(CF₃)— | 1 |
| 308 | 4-Me—C₆H₄ | Me | H | —ON=C(CF₃)— | 1 |
| 309 | 4-Et—C₆H₄ | Me | H | —ON=C(CF₃)— | 1 |
| 310 | 3-MeO—C₆H₄ | Me | H | —ON=C(CF₃)— | 1 |
| 311 | 4-MeO—C₆H₄ | Me | H | —ON=C(CF₃)— | 1 |
| 312 | 3-CF₃—C₆H₄ | Me | H | —ON=C(CF₃)— | 1 |
| 313 | 4-CF₃—C₆H₄ | Me | H | —ON=C(CF₃)— | 1 |
| 314 | 3,4-F₂—C₆H₃ | Me | H | —ON=C(CF₃)— | 1 |
| 315 | 3,5-F₂—C₆H₃ | Me | H | —ON=C(CF₃)— | 1 |
| 316 | 3,4-Cl₂—C₆H₃ | Me | H | —ON=C(CF₃)— | 1 |
| 317 | 3,5-Cl₂—C₆H₃ | Me | H | —ON=C(CF₃)— | 1 |
| 318 | 3,4-Me2—C₆H₃ | Me | H | —ON=C(CF₃)— | 1 |
| 319 | 4-Cl—3-Me-C₆H₃ | Me | H | —ON=C(CF₃)— | 1 |
| 320 | 3-Ph—C₆H₄ | Me | H | —ON=C(CF₃)— | 1 |

TABLE 21-continued

| No  | R²              | R³ | R⁴ | M          | n |
|-----|-----------------|----|----|------------|---|
| 321 | morpholino      | Me | H  | —ON=C(Me)- | 1 |
| 322 | 2-Me-morpholino | Me | H  | —ON=C(Me)- | 1 |
| 323 | 2,6-Me₂-morpholino | Me | H | —ON=C(Me)- | 1 |

TABLE 22

| No  | R²                   | R³ | R⁴ | M             | n |
|-----|----------------------|----|----|---------------|---|
| 324 | 3,5-Me₂-morpholino   | Me | H  | —ON=C(Me)-    | 1 |
| 325 | piperidino           | Me | H  | —ON=C(Me)-    | 1 |
| 326 | 3-Me-piperidino      | Me | H  | —ON=C(Me)-    | 1 |
| 327 | 3,5-Me₂-piperidino   | Me | H  | —ON=C(Me)-    | 1 |
| 328 | 4-Me-piperazino      | Me | H  | —ON=C(Me)-    | 1 |
| 329 | pyrrolidino          | Me | H  | —ON=C(Me)-    | 1 |
| 330 | homopiperidino       | Me | H  | —ON=C(Me)-    | 1 |
| 331 | morpholino           | Me | H  | —ON=C(Et)-    | 1 |
| 332 | 2-Me-morpholino      | Me | H  | —ON=C(Et)-    | 1 |
| 333 | 2,6-Me₂-morpholino   | Me | H  | —ON=C(Et)-    | 1 |
| 334 | 3,5-Me₂-morpholino   | Me | H  | —ON=C(Et)-    | 1 |
| 335 | piperidino           | Me | H  | —ON=C(Et)-    | 1 |
| 336 | 3-Me-piperidino      | Me | H  | —ON=C(Et)-    | 1 |
| 337 | 3,5-Me₂-piperidino   | Me | H  | —ON=C(Et)-    | 1 |
| 338 | 4-Me-piperazino      | Me | H  | —ON=C(Et)-    | 1 |
| 339 | pyrrolidino          | Me | H  | —ON=C(Et)-    | 1 |
| 340 | homopiperidino       | Me | H  | —ON=C(Et)-    | 1 |
| 341 | morpholino           | Me | H  | —ON=C(CF₃)—   | 1 |
| 342 | 2-Me-morpholino      | Me | H  | —ON=C(CF₃)—   | 1 |
| 343 | 2,6-Me₂-morpholino   | Me | H  | —ON=C(CF₃)—   | 1 |
| 344 | 3,5-Me₂-morpholino   | Me | H  | —ON=C(CF₃)—   | 1 |

TABLE 23

| No  | R²                  | R³ | R⁴ | M             | n |
|-----|---------------------|----|----|---------------|---|
| 345 | piperidino          | Me | H  | —ON=C(CF₃)—   | 1 |
| 346 | 3-Me-piperidino     | Me | H  | —ON=C(CF₃)—   | 1 |
| 347 | 3,5-Me₂-piperidino  | Me | H  | —ON=C(CF₃)—   | 1 |
| 348 | 4-Me-piperazino     | Me | H  | —ON=C(CF₃)—   | 1 |
| 349 | pyrrolidino         | Me | H  | —ON=C(CF₃)—   | 1 |
| 350 | homopiperidino      | Me | H  | —ON=C(CF₃)—   | 1 |
| 351 | morpholino          | Me | H  | —ON=C(CN)—    | 1 |
| 352 | 2-Me-morpholino     | Me | H  | —ON=C(CN)—    | 1 |
| 353 | 2,6-Me₂-morpholino  | Me | H  | —ON=C(CN)—    | 1 |
| 354 | 3,5-Me₂-morpholino  | Me | H  | —ON=C(CN)—    | 1 |
| 355 | pipendino           | Me | H  | —ON=C(CN)—    | 1 |
| 356 | 3-Me-piperidino     | Me | H  | —ON=C(CN)—    | 1 |
| 357 | 3,5-Me₂-piperidino  | Me | H  | —ON=C(CN)—    | 1 |
| 358 | 4-Me-piperazino     | Me | H  | —ON=C(CN)—    | 1 |
| 359 | pyrrolidino         | Me | H  | —ON=C(CN)—    | 1 |
| 360 | homopiperidino      | Me | H  | —ON=C(CN)—    | 1 |
| 361 | C₆H₅                | Me | H  | —CH=NOCH(CH₃)— | 0 |
| 362 | 4-F—C₆H₄            | Me | H  | —CH=NOCH(CH₃)— | 0 |
| 363 | 3-F—C₆H₄            | Me | H  | —CH=NOCH(CH₃)— | 0 |
| 364 | 3-Cl—C₆H₄           | Me | H  | —CH=NOCH(CH₃)— | 0 |
| 365 | 4-Cl—C₆H₄           | Me | H  | —CH=NOCH(CH₃)— | 0 |

TABLE 24

| No  | R²            | R³ | R⁴ | M              | n |
|-----|---------------|----|----|----------------|---|
| 366 | 4-Br—C₆H₄     | Me | H  | —CH=NOCH(CH₃)— | 0 |
| 367 | 3-Me-C₆H₄     | Me | H  | —CH=NOCH(CH₃)— | 0 |
| 368 | 4-Me-C₆H₄     | Me | H  | —CH=NOCH(CH₃)— | 0 |
| 369 | 4-Et-C₆H₄     | Me | H  | —CH=NOCH(CH₃)— | 0 |
| 370 | 3-MeO-C₆H₄    | Me | H  | —CH=NOCH(CH₃)— | 0 |
| 371 | 4-MeO-C₆H₄    | Me | H  | —CH=NOCH(CH₃)— | 0 |
| 372 | 3-CF₃—C₆H₄    | Me | H  | —CH=NOCH(CH₃)— | 0 |
| 373 | 4-CF₃—C₆H₄    | Me | H  | —CH=NOCH(CH₃)— | 0 |
| 374 | 3,4-F₂—C₆H₃   | Me | H  | —CH=NOCH(CH₃)— | 0 |
| 375 | 3,5-F₂—C₆H₃   | Me | H  | —CH=NOCH(CH₃)— | 0 |

TABLE 24-continued

| No  | R²              | R³ | R⁴ | M                 | n |
|-----|-----------------|----|----|-------------------|---|
| 376 | 3,4-Cl₂—C₆H₃    | Me | H  | —CH=NOCH(CH₃)—    | 0 |
| 377 | 3,5-Cl₂—C₆H₃    | Me | H  | —CH=NOCH(CH₃)—    | 0 |
| 378 | 3,4-Me₂-C₆H₃    | Me | H  | —CH=NOCH(CH₃)—    | 0 |
| 379 | 4-Cl-3-Me-C₆H₃  | Me | H  | —CH=NOCH(CH₃)—    | 0 |
| 380 | C₆H₅            | Me | H  | —CH=NOCH₂—        | 0 |
| 381 | C₆H₅            | Me | H  | —CH=NN=C(CH₃)—    | 0 |
| 382 | 4-F—C₆H₄        | Me | H  | —CH=NN=C(CH₃)—    | 0 |
| 383 | 3-F—C₆H₄        | Me | H  | —CH=NN=C(CH₃)—    | 0 |
| 384 | 3-Cl—C₆H₄       | Me | H  | —CH=NN=C(CH₃)—    | 0 |
| 385 | 4-Cl—C₆H₄       | Me | H  | —CH=NN=C(CH₃)—    | 0 |
| 386 | 4-Br—C₆H₄       | Me | H  | —CH=NN=C(CH₃)—    | 0 |

TABLE 25

| No  | R²              | R³ | R⁴ | M                 | n |
|-----|-----------------|----|----|-------------------|---|
| 387 | 3-Me-C₆H₄       | Me | H  | —CH=NN=C(CH₃)—    | 0 |
| 388 | 4-Me-C₆H₄       | Me | H  | —CH=NN=C(CH₃)—    | 0 |
| 389 | 4-Et-C₆H₄       | Me | H  | —CH=NN=C(CH₃)—    | 0 |
| 390 | 3-MeO-C₆H₄      | Me | H  | —CH=NN=C(CH₃)—    | 0 |
| 391 | 4-MeO-C₆H₄      | Me | H  | —CH=NN=C(CH₃)—    | 0 |
| 392 | 3-CF₃—C₆H₄      | Me | H  | —CH=NN=C(CH₃)—    | 0 |
| 393 | 4-CF₃—C₆H₄      | Me | H  | —CH=NN=C(CH₃)—    | 0 |
| 394 | 3,4-F₂—C₆H₃     | Me | H  | —CH=NN=C(CH₃)—    | 0 |
| 395 | 3,5-F₂—C₆H₃     | Me | H  | —CH=NN=C(CH₃)—    | 0 |
| 396 | 3,4-Cl₂—C₆H₃    | Me | H  | —CH=NN=C(CH₃)—    | 0 |
| 397 | 3,5-Cl₂—C₆H₃    | Me | H  | —CH=NN=C(CH₃)—    | 0 |
| 398 | 3,4-Me₂-C₆H₃    | Me | H  | —CH=NN=C(CH₃)—    | 0 |
| 399 | 4-Cl-3-Me—C₆H₃  | Me | H  | —CH=NN=C(CH₃)—    | 0 |
| 400 | 3-Ph—C₆H₄       | Me | H  | —CH=NN=C(CH₃)—    | 0 |
| 401 | C₆H₅            | Me | H  | —S—C(CH₃)=N—      | 1 |
| 402 | 4-F—C₆H₄        | Me | H  | —S—C(CH₃)=N—      | 1 |
| 403 | 3-F—C₆H₄        | Me | H  | —S—C(CH₃)=N—      | 1 |
| 404 | 3-Cl—C₆H₄       | Me | H  | —S—C(CH₃)=N—      | 1 |
| 405 | 4-Cl—C₆H₄       | Me | H  | —S—C(CH₃)=N—      | 1 |
| 406 | 4-Br—C₆H₄       | Me | H  | —S—C(CH₃)=N—      | 1 |
| 407 | 3-Me-C₆H₄       | Me | H  | —S—C(CH₃)=N—      | 1 |

TABLE 26

| No  | R²              | R³ | R⁴ | M              | n |
|-----|-----------------|----|----|----------------|---|
| 408 | 4-Me-C₆H₄       | Me | H  | —S—C(CH₃)=N—   | 1 |
| 409 | 4-Et-C₆H₄       | Me | H  | —S—C(CH₃)=N—   | 1 |
| 410 | 3-MeO-C₆H₄      | Me | H  | —S—C(CH₃)=N—   | 1 |
| 411 | 4-MeO-C₆H₄      | Me | H  | —S—C(CH₃)=N—   | 1 |
| 412 | 3-CF₃—C₆H₄      | Me | H  | —S—C(CH₃)=N—   | 1 |
| 413 | 4-CF₃—C₆H₄      | Me | H  | —S—C(CH₃)=N—   | 1 |
| 414 | 3,4-F₂—C₆H₃     | Me | H  | —S—C(CH₃)=N—   | 1 |
| 415 | 3,5-F₂—C₆H₃     | Me | H  | —S—C(CH₃)=N—   | 1 |
| 416 | 3,4-Cl₂—C₆H₃    | Me | H  | —S—C(CH₃)=N—   | 1 |
| 417 | 3,5-Cl₂—C₆H₃    | Me | H  | —S—C(CH₃)=N—   | 1 |
| 418 | 3,4-Me₂-C₆H₃    | Me | H  | —S—C(CH₃)=N—   | 1 |
| 419 | 4-Cl-3-Me-C₆H₃  | Me | H  | —S—C(CH₃)=N—   | 1 |
| 420 | 3-Ph—C₆H₄       | Me | H  | —S—C(CH₃)=N—   | 1 |
| 421 | C₆H₅            | Me | H  | —ON=CH—        | 1 |
| 422 | 4-F—C₆H₄        | Me | H  | —ON=CH—        | 1 |
| 423 | 3-F—C₆H₄        | Me | H  | —ON=CH—        | 1 |
| 424 | 3-Cl—C₆H₄       | Me | H  | —ON=CH—        | 1 |
| 425 | 4-Cl—C₆H₄       | Me | H  | —ON=CH—        | 1 |
| 426 | 4-Br—C₆H₄       | Me | H  | —ON=CH—        | 1 |
| 427 | 3-Me-C₆H₄       | Me | H  | —ON=CH—        | 1 |
| 428 | 4-Me-C₆H₄       | Me | H  | —ON=CH—        | 1 |

TABLE 27

| No  | R²           | R³ | R⁴ | M         | n |
|-----|--------------|----|----|-----------|---|
| 429 | 4-Et-C₆H₄    | Me | H  | —ON=CH—   | 1 |
| 430 | 3-MeO-C₆H₄   | Me | H  | —ON=CH—   | 1 |

TABLE 27-continued

| No | R² | R³ | R⁴ | M | n |
|---|---|---|---|---|---|
| 431 | 4-MeO-C₆H₄ | Me | H | —ON=CH— | 1 |
| 432 | 3-CF₃—C₆H₄ | Me | H | —ON=CH— | 1 |
| 433 | 4-CF₃—C₆H₄ | Me | H | —ON=CH— | 1 |
| 434 | 3,4-F₂—C₆H₃ | Me | H | —ON=CH— | 1 |
| 435 | 3,5-F₂—C₆H₃ | Me | H | —ON=CH— | 1 |
| 436 | 3,4-Cl₂—C₆H₃ | Me | H | —ON=CH— | 1 |
| 438 | 314-Me₂-C₆H₃ | Me | H | —ON=CH— | 1 |
| 439 | 3-F—C₆H₄ | Et | H | O | 1 |
| 440 | 4-F—C₆H₄ | Et | H | O | 1 |
| 441 | 2-Cl—C₆H₄ | Et | H | O | 1 |
| 442 | 3-Cl—C₆H₄ | Et | H | O | 1 |
| 443 | 4-Cl—C₆H₄ | Et | H | O | 1 |
| 444 | 2-Me-C₆H₄ | Et | H | O | 1 |
| 445 | 3-Me-C₆H₄ | Et | H | O | 1 |
| 446 | 4-Me-C₆H₄ | Et | H | O | 1 |
| 447 | 3-CF₃—C₆H₄ | Et | H | O | 1 |
| 448 | 2,5-Me₂-C₆H₃ | Et | H | O | 1 |
| 449 | 4-Cl-2-Me-C₆H₃ | Et | H | O | 1 |
| 450 | 2,5-Cl₂-C₆H₃ | Et | H | O | 1 |

TABLE 28

| No | R² | R³ | R⁴ | M | n |
|---|---|---|---|---|---|
| 451 | 4-Cl—C₆H₄ | Et | H | —ON=C(Me)- | 1 |
| 452 | 3-CF₃—C₆H₄ | Et | H | —ON=C(Me)- | 1 |
| 453 | 4-CF₃—C₆H₄ | Et | H | —ON=C(Me)- | 1 |
| 454 | 4-Me-C₆H₄ | Et | H | —ON=C(Me)- | 1 |
| 455 | 3,4-Cl₂—C₆H₃ | Et | H | —ON=C(Me)- | 1 |
| 456 | 4-Cl—C₆H₄ | Et | H | —ON=C(SMe)- | 1 |
| 457 | 3-CF₃—C₆H₄ | Et | H | —ON=C(SMe)- | 1 |
| 458 | 4-CF₃—C₆H₄ | Et | H | —ON=C(SMe)- | 1 |
| 459 | 4-Me-C₆H₄ | Et | H | —ON=C(SMe)- | 1 |
| 460 | 3,4-Cl₂—C₆H₃ | Et | H | —ON=C(SMe)- | 1 |
| 461 | 4-Cl—C₆H₄ | Et | H | —CH=NOCH(CH₃)— | 0 |
| 462 | 3-CF₃—C₆H₄ | Et | H | —CH=NOCH(CH₃)— | 0 |
| 463 | 3-CF₃—C₆H₄ | Et | H | —CH=NOCH(CH₃)— | 0 |
| 464 | 4-Me-C₆H₄ | Et | H | —CH=NOCH(9H3)— | 0 |
| 465 | 3,4-Cl₂—C₆H₃ | Et | H | —CH=NOCH(CH₃)— | 0 |
| 466 | 4-Cl—C₆H₄ | Et | H | —CH=NN=C(CH₃)— | 0 |
| 467 | 3-CF₃—C₆H₄ | Et | H | —CH=NN=C(CH₃)— | 0 |
| 468 | 4-CF₃—C₆H₄ | Et | H | —CH=NN=C(CH₃)— | 0 |
| 469 | 4-Me-C₆H₄ | Et | H | —CH=NN=C(CH₃)— | 0 |
| 470 | 3,4-Cl₂—C₆H₃ | Et | H | —CH=NN=C(CH₃)— | 0 |
| 471 | 4-Ph—C₆H₄ | Et | H | O | 1 |

TABLE 29

| No | R² | R³ | R⁴ | M | n |
|---|---|---|---|---|---|
| 472 | C₆H₅ | Et | H | O | 0 |
| 473 | C₆H₅ | Me | H | —CH=NOC(CH₃)₂— | 0 |
| 474 | 4-F—C₆H₄ | Me | H | —CH=NOC(CH₃)₂— | 0 |
| 475 | 3-F—C₆H₄ | Me | H | —CH=NOC(CH₃)₂— | 0 |
| 476 | 3-Cl—C₆H₄ | Me | H | —CH=NOC(CH₃)₂— | 0 |
| 477 | 4-Cl—C₆H₄ | Me | H | —CH=NOC(CH₃)₂— | 0 |
| 478 | 4-Br—C₆H₄ | Me | H | —CH=NOC(CH₃)₂— | 0 |
| 479 | 3-Me-C₆H₄ | Me | H | —CH=NOC(CH₃)₂— | 0 |
| 480 | 4-Me-C₆H₄ | Me | H | —CH=NOC(CH₃)₂— | 0 |
| 481 | 4-Et-C₆H₄ | Me | H | —CH=NOC(CH₃)₂— | 0 |
| 482 | 3-MeO-C₆H₄ | Me | H | —CH=NOC(CH₃)₂— | 0 |
| 483 | 4-MeO-C₆H₄ | Me | H | —CH=NOC(CH₃)₂— | 0 |
| 484 | 3-CF₃—C₆H₄ | Me | H | —CH=NOC(CH₃)₂— | 0 |
| 485 | 4-CF₃—C₆H₄ | Me | H | —CH=NOC(CH₃)₂— | 0 |
| 486 | 3,4-F₂—C₆H₃ | Me | H | —CH=NOC(CH₃)₂— | 0 |
| 487 | 3,5-F₂—C₆H₃ | Me | H | —CH=NOC(CH₃)₂— | 0 |
| 488 | 3,4-Cl₂—C₆H₃ | Me | H | —CH=NOC(CH₃)₂— | 0 |
| 489 | 3,5-Cl₂—C₆H₃ | Me | H | —CH=NOC(CH₃)₂— | 0 |
| 490 | 3,4-Me₂—C₆H₃ | Me | H | —CH=NOC(CH₃)₂— | 0 |
| 491 | 4-Cl-3-Me-C₆H₃ | Me | H | —CH=NOC(CH₃)₂— | 0 |
| 492 | 6-(2-CN—PhO)-4-primidyl | Et | H | O | 0 |

TABLE 30

| No | R² | R³ | R⁴ | M | n |
|---|---|---|---|---|---|
| 493 | 2-Cl—C₆H₄ | Me | H | —CH=NOCH(CH₃)— | 0 |
| 494 | 2,4-Cl₂—C₆H₃ | Me | H | —CH=NOCH(CH₃)— | 0 |
| 495 | 3-CF₃O—C₆H₃ | Me | H | —CH=NOCH(CH₃)— | 0 |
| 496 | 4-CF₃O—C₆H₃ | Me | H | —CH=NOCH(CH₃)— | 0 |
| 497 | 2-pyridyl | Me | H | —CH=NOCH(CH₃)— | 0 |
| 498 | 3-pyridyl | Me | H | —CH=NOCH(CH₃)— | 0 |
| 499 | 4-pyridyl | Me | H | —CH=NOCH(CH₃)— | 0 |
| 500 | 2-furyl | Me | H | —CH=NOCH(CH₃)— | 0 |
| 501 | 2-thienyl | Me | H | —CH=NOCH(CH₃)— | 0 |
| 502 | 3-isoxazolyl | Me | H | —CH=NOCH(CH₃)— | 0 |
| 503 | 2,4-Cl₂—C₆H₃ | Me | H | —CH=NN=C(CH₃)— | 0 |
| 504 | 3-CF₃O—C₆H₃ | Me | H | —CH=NN=C(CH₃)— | 0 |
| 505 | 4-CF₃O—C₆H₃ | Me | H | —CH=NN=C(CH₃)— | 0 |
| 506 | 2-pyridyl | Me | H | —CH=NN=C(CH₃)— | 0 |
| 507 | 3-pyridyl | Me | H | —CH=NN=C(CH₃)— | 0 |
| 508 | 4-pyridyl | Me | H | —CH=NN=C(CH₃)— | 0 |
| 509 | 2-furyl | Me | H | —CH=NN=C(CH₃)— | 0 |
| 510 | 2-thienyl | Me | H | —CH=NN=C(CH₃)— | 0 |
| 511 | 3-isoxazolyl | Me | H | —CH=NN=C(CH₃)— | 0 |
| 512 | 2-Cl—C₆H₄ | Me | H | —CH=NN=C(CH₃)— | 0 |

TABLE 31

| No | Physical data |
|---|---|
| A-12 | $^1$H-NMR(CDCl₃) δ ppm: 2.19(3H, s), 2.23(3H, s), 3.44(3H, s), 5.05(1H, d, J=12.2), 5.14(1H, d, J=12.2), 5.69(1H, s), 5.90(1H, s), 6.85–6.91(2H, m), 7.13–7.18(2H, m), 7.37–7.56(4H, m). |
| A-22 | $^1$H-NMR(CDCl₃) δ ppm: 2.23(3H, s), 3.43(3H, s), 5.11(1H, d, J=11.6), 5.17(1H, d, J=11.6), 5.63(1H, s), 5.91(1H, s), 7.03–7.58(8H, m). |
| A-31 | mp 78.5~79.5° C. |
| A-32 | $^1$H-NMR(CDCl₃) δ ppm: 2.24(3H, s), 3.43(3H, s), 5.05(1H, d, J=12.2), 5.11(1H, d, J=12.2), 5.60(1H, s), 5.90(1H, s), 6.74(1H, dd, J=8.5, 2.4), 7.00(1H, d, J=3.1), 7.30–7.57(5H, m). |
| A-36 | $^1$H-NMR(CDCl₃) δ ppm: 2.14(3H, s), 2.23(3H, s), 2.32(3H, s), 3.44(3H, s), 5.03(1H, d, J=12.2), 5.12(1H, d, J=11.6), 5.69(1H, s), 5.90(1H, s), 6.69–6.71(2H, m), 7.12(1H, d, J=7.3), 7.34–7.57(4H, m). |
| A-41 | $^1$H-NMR(CDCl₃) δ ppm: 2.16(3H, s), 2.23(3H, s), 3.43(3H, s), 5.04(1H, d, J=11.6), 5.11(1H, d, J=12.2), 5.64(1H, s), 5.90(1H, s), 6.75(1H, d, J=8.5), 7.07–7.11(2H, m), 7.35–7.55(4H, m). |
| A-44 | $^1$H-NMR(CDCl₃) δ ppm: 2.24(3H, s), 3.45(3H, s), 5.11(1H, d, J=11.6), 5.19(1H, d, J=11.6), 5.69(1H, s), 5.92(1H, s), 6.97–7.00(2H, m), 7.27–7.61(11H, m). |
| A-55 | $^1$H-NMR(CDCl₃) δ ppm: 2.06(3H, s), 2.23(6H, s), 2.29(3H, s), 3.43(3H, s), 5.00(1H, |

TABLE 31-continued

| No | Physical data |
|---|---|
|  | d, J=11.6), 5.10(1H, d, J=11.6), 5.69(1H, s), 5.89(1H, s), 6.58(1H, s), 6.64(1H, s), 7.35–7.57(4H, m). |
| A-65 | $^1$H-NMR(CDCl$_3$) δ ppm: 2.34(3H, s), 3.45(3H, s), 5.48(2H, s), 5.80(1H, s), 5.90(1H, s), 7.34–7.56(4H, m), 7.64(1H, d, J=2.4), 7.99(1H, d, J=2.4). |
| A-66 | mp 57~5.59° C. |
| A-67 | $^1$H-NMR(CDCl$_3$) δ ppm: 2.24(3H, s), 3.45(3H, s), 5.53(1H, d, J=12.7), 5.57(1H, J=13.0), 5.82(1H, s), 5.91(1H, s), 6.98(1H, dd, J=6.8, 5.1), 7.34–7.52(4H, m), 7.87(1H, d, J=7.3), 8.31(1H, d, J=5.1). |
| A-68 | $^1$H-NMR(CDCl$_3$) δ ppm: 2.25(3H, s), 3.45(3H, s), 5.52(2H, s), 5.77(1H, s), 5.92(1H, s), 7.33–7.54(4H, m), 7.84(1H, d, J=2.6), 8.25(1H, d, 2.5). |
| A-69 | $^1$H-NMR(CDCl$_3$) δ ppm: 2.24(3H, s), 3.46(3H, s), 5.57(2H, s), 5.79(1H, s), 5.91(1H, s), 7.35–7.56(4H, m), 7.85(1H, d, J=2.2), 8.33(1H, t, J=1.2). |
| A-76 | $^1$H-NMR(CDCl$_3$) δ ppm: 2.25(3H, s), 3.45(3H, s), 5.63(1H, d, J=12.2), 5.70(1H, d, J=12.2), 5.72(1H, s), 5.95(1H, s), 7.32–7.62(7H, m). |
| A-87 | $^1$H-NMR(CDCl$_3$) δ ppm: 2.10(3H, s), 2.21(3H, s), 3.42(3H, s), 5.29(2H, s), 5.77(1H, s), 5.86(1H, s), 7.30–7.60(8H, m). |

TABLE 32

| No | Physical data |
|---|---|
| A-102 | $^1$H-NMR(CDCl$_3$) δ ppm: 2.16(3H, s), 2.21(3H, s), 3.43(3H, s), 5.32(2H, s), 5.77(1H, s), 5.87(1H, s), 7.33–7.64(6H, m), 7.80(1H, d, J=7.9), 7.87(1H, s). |
| A-103 | $^1$H-NMR(CDCl$_3$) δ ppm: 2.15(3H, s), 2.21(3H, s), 3.43(3H, s), 5.32(2H, s), 5.77(1H, s), 5.87(1H, s), 7.36–7.74(8H, m). |
| A-110 | $^1$H-NMR(CDCl$_3$) δ ppm: 2.10(3H, s), 2.21(3H, s), 3.43(3H, s), 5.30(2H, s), 5.75(1H, s), 5.87(1H, s), 7.33–7.58(6H, m), 7.71(1H, d, J=1.8). |
| A-147 | mp 68~73° C. |
| A-241 | $^1$H-NMR(CDCl$_3$) δ ppm: 2.24(3H, s), 3.42(3H, s), 5.81(1H, s), 5.94(1H, s), 6.85–7.60(9H, m). |
| A-323 | $^1$H-NMR(CDCl$_3$) δ ppm: 1.18(6H, d, J=6.1), 1.83(3H, s), 2.24(3H, s), 2.31(2H, dd, J=12.8, 11.0), 3.42–3.68(7H, m), 4.96(1H, d, J=12.2), 5.01(1H, d, J=12.2), 7.29–7.55(4H, m). |
| A-327 | $^1$H-NMR(CDCl$_3$) δ ppm: 0.66(1H, q, J=12.8), 0.86(6H, d, J=6.7), 1.57–1.82(3H, m), 1.84(3H, s), 2.03(2H, t, J=12.8), 2.23(3H, s), 3.42(3H, s), 3.63(2H, dd, J=12.2, 3.7), 4.94(1H, d, J=11.6), 5.00(1H, d, J=11.6), 5.78(1H, s), 5.84(1H, s), 7.31–7.55(4H, m). |
| A-361 | $^1$H-NMR(CDCl$_3$) δ ppm: 1.56(1.61)(3H, d, J=6.7), 2.16(2.23)(3H, s), 3.27(3.39 (3H, s), 5.26–5.35(1H, m), 5.57(5.69)(1H, s), 5.79(5.91)(1H, s), 7.27–7.63(9H, m), 8.30(8.35)(1H, s). |
| A-373 | $^1$H-NMR(CDCl$_3$) ppm: 1.57–1.60(3H, m), 2.14(2.23)(3H, s), 3.26(3.39)(3H, s), 5.34(1H, sept, J=6.7), 5.57(5.68)(1H, s), 5.69(5.86)(1H, s), 7.33–7.64(8H, m), 8.32(8.37)(1H, s). |
| A-385 | $^1$H-NMR(CDCl$_3$) δ ppm: 2.22(3H, s), 2.41 (3H, s), 3.48(3H, s), 5.79(1H, s), 6.28(1H, s), 7.38–7.90(8H, m), 8.66(1H, s). |
| A-393 | $^1$H-NMR(CDCl$_3$) δ ppm: 2.23(3H, s), 2.44(3H, s), 3.49(3H, s), 5.81(1H, s), 6.26(1H, s), 7.43–8.02(8H, m), 8.57(1H, s). |
| A-448 | $^1$H-NMR(CDCl$_3$) δ ppm: 1.25(3H, t, J=7.3), 2.15(3H, s), 2.23(3H, s), 2.32(3H, s), 3.55–3.65(2H, m), 5.03(1H, d, J=11.6), 5.13(1H, d, J=11.6), 5.79(1H, s), 5.91(1H, s), 6.68–6.71(2H, m) 7.02(1H, d, J=7.3), 7.36–7.57(4H, m). |
| A-449 | $^1$H-NMR(CDCl$_3$) δ ppm: 1.25(3H, t, J=7.3), 2.16(3H, s), 2.23(3H, s), 3.50–3.67(2H, m), 5.05(1H, d, J=12.2), 5.11(1H, d, J=12.2), 5.74(1H, s), 5.90(1H, s), 6.75(1H, d, J=8.5), 7.06–7.11(2H, m), 7.33–7.58(4H, m). |
| A-471 | $^1$H-NMR(CDCl$_3$) δ ppm: 1.26(3H, t, J=6.7), 2.24(3H, s), 3.56–3.64(2H, m), 5.12(1H, d, J=12.2), 5.19(1H, d, J=11.6), 5.79(1H, s), 5.92(1H, s), 6.95–7.01(2H, m), 7.28–7.64(11H, m). |
| A-472 | $^1$H-NMR(CDCl$_3$) δ ppm: 1.22(3H, t, J=7.3), 2.23(3H, s), 3.54–3.63(2H, m), 5.91(1H, s), 5.94(1H, s), 6.88–7.34(8H, m), 7.59(1H, dd, J=7.9, 1.8). |

TABLE 33

| No | Physical data |
|---|---|
| B-36 | $^1$H-NMR(CDCl$_3$) δ ppm: 1.21(3H, t, J=7.9), 2.13(3H, s), 2.32(3H, s), 2.63(2H, q, J=7.9), 3.44(3H, s), 5.03(1H, d, J=11.6), 5.12(1H, d, J=11.6), 5.70(1H, s), 5.93(1H, s), 6.69–6.79(2H, m), 7.02(1H, d, J=7.9), 7.25–7.58(4H, m). |
| C-36 | $^1$H-NMR(CDCl$_3$) δ ppm: 1.81(3H, s), 2.16(3H, s), 2.34(3H, s), 2.74–2.79(2H, m), 3.29(3H, s), 4.64(1H, d, J=6.1), 4.87–4.96(1H, m), 5.07(1H, d, J=11.0), 5.16(1H, d, J=11.6), 6.72(1H, d, J=7.3), 6.79(1H, s), 7.03(1H, d, J=7.3), 7.33–7.52(4H, m). |
| D-36 | $^1$H-NMR(CDCl$_3$) δ ppm: 2.19(3H, s), 2.32(3H, s), 3.43(3H, s), 5.02(1H, d, J=12.2), 5.20(1H, d, J=12.2), 5.80(1H, s), 6.32(1H, d, J=1.8), 6.68–6.70(2H, m), 7.12(1H, d, J=7.9), 7.32–7.63(4H, m), 8.32(1H, d, J=1.2). |
| D-41 | $^1$H-NMR(CDCl$_3$) δ ppm: 2.20(3H, s), 3.42(3H, s), 5.01(1H, d, J=12.2), 5.18(1H, d, J=12.2), 5.76(1H, s), 6.31(1H, d, J=1.8), 6.77(1H, d, J=8.6), 7.07–7.12(2H, m), 7.3214 7.64(4H, m), 8.32(1H, d, J=1.8). |
| D-65 | mp 86~87° C. |
| D-66 | $^1$H-NMR(CDCl$_3$) δ ppm: 3.42(3H, s), 5.45(1H, d, J=12.8), 5.57(1H, d, J=12.8), 5.87(1H, s), 6.32(1H, d, J=1.2), 6.79(1H, d, J=8.6), 7.32–7.79(5H, m), 8.32(1H, d, J=1.2), 8.44(1H, s). |
| D-67 | $^1$H-NMR(CDCl$_3$) δ ppm: 3.44(3H, s), 5.52(1H, d, J=13.4), 5.64(1H, d, J=13.4), 5.94(1H, s), 6.31(1H, d, J=1.8), 6.98(1H, dd, J=7.3, 4.9), 7.31–7.63(4H, m), 7.87(1H, d, J=7.9), 8.31–8.32(2H, m). |
| D-68 | $^1$H-NMR(CDCl$_3$) δ ppm: 3.43(3H, s), 5.59(1H, d, J=12.8), 5.61(1H, d, J=12.8), 5.90(1H, s), 6.31(1H, d, J=1.8), 7.31–7.63(4H, m), 7.84(1H, d, J=2.4), 8.26(1H, d, J=2.4), 8.32(1H, d, J=1.8). |
| D-69 | $^1$H-NMR(CDCl$_3$) δ ppm: 3.45(3H, s), 5.55(1H, d, J=12.8), 5.63(1H, d, J=12.8), 5.93(1H, s), 6.33(1H, d, J=1.2), 7.32–7.65(4H, m), 7.85(1H, d, J=1.8), 8.32–8.33(2H, m). |
| D-70 | $^1$H-NMR(CDCl$_3$) δ ppm: 3.44(3H, s), 5.63(1H, d, J=12.2), 5.76(1H, d, J=12.2), 5.89(1H, s), 6.34(1H, d, J=1.8), 7.20–7.72(8H, m), 8.33(1H, d, J=1.2). |
| D-84 | $^1$H-NMR(CDCl$_3$) δ ppm: 2.18(3H, s), 3.41(3H, s), 5.23(1H, d, J=12.2), 5.4(1H, d, J=12.2), 5.91(1H, s), 6.30(1H, d, J=1.2), 7.00–7.07(2H, m), 7.31–7.65(6H, m), 8.31(1H, d, J=1.8). |
| D-87 | $^1$H-NMR(CDCl$_3$) δ ppm: 2.17(3H, s), 3.41(3H, s), 5.24(1H, d, J=12.2), 5.31(1H, d, J=12.2), 5.91(1H, s), 6.30(1H, d, J=1.8), 7.29–7.65(8H, m), 8.31(1H, d, J=1.8). |
| D-94 | $^1$H-NMR(CDCl$_3$) δ ppm: 2.18(3H, s), 2.35(3H, s), 3.41(3H, s), 5.23(1H, d, J=12.2), 5.40(1H, d, J=12.2), 5.92(1H, s), 6.29(1H, d, J=1.8), 7.17–7.61(8H, m), 8.30(1H, d, J=1.8). |

TABLE 34

| No | Physical data |
|---|---|
| D-103 | $^1$H-NMR(CDCl$_3$) δ ppm: 2.21(3H, s), 3.42(3H, s), 5.27(1H, d, J=12.2), 5.44(1H, d, J=12.2), 5.91(1H, s), 6.30(1H, d, J=1.2), 7.31–7.56(8H, m), 8.31(1H, d, J=1.2). |
| D-110 | $^1$H-NMR(CDCl$_3$) δ ppm: 2.15(3H, s), 3.42(3H, s), 5.25(1H, d, J=12.8), 5.42(1H, d, J=12.8), 5.89(1H, s), 6.30(1H, d, J=1.2), 7.31–7.64(6H, m), 7.73(1H, d, J=1.8), 8.31(1H, d, J=1.8). |
| D-147 | $^1$H-NMR(CDCl$_3$) δ ppm: 2.09(3H, s), 3.42(3H, s), 5.25(1H, d, J=12.2), 5.45(1H, d, J=12.8), 5.93(1H, s), 6.30(1H, d, J=1.8), 7.30–7.61(6H, m), 8.30(1H, d, J=1.8). |
| D-154 | mp 73.5~74.5° C. |
| D-323 | $^1$H-NMR(CDCl$_3$) δ ppm: 1.18(6H, d, J=6.1), 1.89(3H, s), 2.31(2H, dd, J=12.8, 10.4), 3.40(3H, s), 3.45(2H, d, J=11.6), 3.57–3.68(2H, m), 4.94(1H, d, J=11.6), 5.10(1H, d, J=12.2), 5.89(1H, s), 6.28(1H, d, J=1.8), 7.28–7.59(4H, m), 8.30(1H, d, J=1.8). |
| D-448 | $^1$H-NMR(CDCl$_3$) δ ppm: 1.26(3H, t, J=7.3), 2.19(3H, s), 2.31(3H, s), 3.54–3.63(2H, m), 5.02(1H, d, J=12.2), 5.21(1H, d, J=12.2), 5.91(1H, s), 6.33(1H, d, J=1.8), 6.69(2H, brs), 7.02(1H, d, J=7.9), 7.31–7.65(4H, m), 8.31(1H, d, J=1.2). |
| D-449 | $^1$H-NMR(CDCl$_3$) δ ppm: 1.26(3H, t, J=7.3), 2.20(3H, s), 3.53–3.61(2H, m), 5.02(1H, J=12.8), 5.19(1H, d, J=12.2), 5.86(1H, s), 6.33(1H, d, J=1.2), 6.77(1H, d, J=8.6), 7.07–7.12(2H, m), 7.32–7.67(4H, m), 8.32(1H, d, J=1.2). |
| E-12 | $^1$H-NMR(CDCl$_3$) δ ppm: 2.25(3H, s), 2.36(3H, s), 3.42(3H, s), 5.02(1H, d, J=12.2), 5.22(1H, d, J=12.2), 5.69(1H, s), 5.91(1H, s), 6.85–6.90(2H, m), 7.13–7.17(2H, m), 7.32–7.64(4H, m). |
| E-36 | $^1$H-NMR(CDCl$_3$) δ ppm: 2.20(3H, s), 2.31(3H, s), 2.36(3H, s), 3.42(3H, s), 5.01(1H, d, J=12.2), 5.20(1H, d, J=12.2), 5.69(1H, s), 5.91(1H, s), 6.68–6.70(2H, m), 7.02(1H, d, J=7.9), 7.31–7.63(4H, m). |
| E-65 | $^1$H-NMR(CDCl$_3$) δ ppm: 2.35(3H, s), 3.39(3H, s), 5.45(1H, d, J=12.8), 5.53(1H, d, J=12.8), 5.82(1H, s), 5.91(1H, s), 7.26–7.65(5H, m), 8.00(1H, d, J=2.4). |
| E-66 | $^1$H-NMR(CDCl$_3$) δ ppm: 2.36(3H, s), 3.36(3H, s), 5.44(1H, d, J=12.8), 5.57(1H, d, J=12.2), 5.77(1H, s), 5.92(1H, s), 6.80(1H, d, J=8.5), 7.30–7.79(5H, m), 8.45(1H, |

TABLE 34-continued

| No | Physical data |
|---|---|
| | s). |
| E-67 | $^1$H-NMR(CDCl$_3$) δ ppm: 2.36(3H, s), 3.43(3H, s), 5.51(1H, d, J=13.4), 5.65(1H, d, J=13.4), 5.83(1H, s), 5.91(1H, s), 6.98(1H, dd, J=7.3, 4.9), 7.29–7.63(4H, m), 7.86–7.88(1H, m), 8.31–8.33(1H, m). |
| E-68 | $^1$H-NMR(CDCl$_3$) δ ppm: 2.36(3H, s), 3.42(3H, s), 5.48(1H, d, J=13.4), 5.62(1H, d, J=12.8), 5.79(1H, s), 5.91(1H, s), 7.30–7.63(4H, m), 7.84(1H, d, J=2.4), 8.26(1H, d, J=2.4). |
| E-69 | $^1$H-NMR(CDCl$_3$) δ ppm: 2.36(3H, s) 3.39(3H, s), 5.54(1H, d, J=12.8), 5.62(1H, d, J=12.8), 5.82(1H, s), 5.92(1H, 5) 7.31–7.65(4H, m), 7.85(1H, d, J=2.4), 8.33(1H, d, J=2.4). |

TABLE 35

| No | Physical data |
|---|---|
| E-87 | $^1$H-NMR(CDCl$_3$) δ ppm: 2.18(3H, s), 2.32(3H, s), 3.40(3H, s), 5.22(1H, d, J=12.8), 5.31(1H, d, J=12.8), 5.80(1H, s), 5.90(1H, s), 7.30–7.62(8H, m). |
| E-100 | $^1$H-NMR(CDCl$_3$) δ ppm: 2.18(3H, s), 2.35(3H, s), 3.40(3H, s), 3.82(3H, s), 5.21(1H, d, J=12.8), 5.40(1H, d, J=12.8), 5.82(1H, s), 5.90(1H, s), 6.85–6.90(2H, m), 7.31–7.61(6H, m). |
| E-103 | $^1$H-NMR(CDCl$_3$) δ ppm: 2.22(3H, s), 2.35(3H, s), 3.41(3H, s), 5.25(1H, d, J=12.2), 5.44(1H, d, J=12.2), 5.80(1H, s), 5.91(1H, s), 7.32–7.76(8H, m). |
| E-110 | $^1$H-NMR(CDCl$_3$) δ ppm: 2.16(3H, s), 2.35(3H, s), 3.44(3H, s), 5.23(1H, d, J=12.2), 5.42(1H, d, J=12.8), 5.79(1H, s), 5.91(1H, s), 7.32–7.60(5H, m), 7.63(1H, J=1.8), 7.72(1H, d, J=1.2). |
| E-323 | $^1$H-NMR(CDCl$_3$) δ ppm: 1.18(6H, d, J=6.7), 1.90(3H, s), 2.31(2H, dd, J=12.8, 10.4), 2.35(3H, s), 3.40(3H, s), 3.46(2H, dd, J=13.4, 1.0), 3.57–3.68(2H, m), 4.92(1H, d, J=12.2), 5.11(1H, d, J=12.2), 5.78(1H, s), 5.89(1H, s), 7.30–7.60(4H, m). |
| F-36 | $^1$H-NMR(CDCl$_3$) δ ppm: 2.21(3H, s), 2.33(3H, s), 2.68–2.82(1H, m), 2.95–3.08(1H, m), 3.42(3H, s), 4.17–4.35(2H, m), 4.99(1H, d, J=12.2), 5.21(1H, d, J=11.6), 5.51(1H, s), 6.70(1H, d, J=7.3), 6.75(1H, s), 7.03(1H, d, J=7.3), 7.36–7.61 (4H, m). |
| F-41 | $^1$H-NMR(CDCl$_3$) δ ppm: 2.23(3H, s), 2.65–2.79(1H, m), 2.94–3.08(1H, m), 3.41(3H, s), 4.18–4.36(2H, m), 4.99(1H, d, J=12.2), 5.21(1H, d, J=12.2), 5.47(1H, s), 6.84(1H, d, J=8.6), 7.09–7.13(2H, m), 7.34–7.61(4H, m). |
| F-55 | $^1$H-NMR(CDCl$_3$) δ ppm: 2.13(3H, s), 2.24(3H, s), 2.30(3H, s), 2.68–3.08(2H, m), 3.41(3H, s), 4.18–4.35(2H, m), 4.96(1H, d, J=12.2), 5.19(1H, d, J=12.2), 5.51(1H, s), 6.64(2H, s), 7.36–7.64(4H, m). |
| F-66 | mp 71~72° C. |
| F-68 | mp 126.5~128° C. |
| F-69 | $^1$H-NMR(CDCl$_3$) δ ppm: 2.67–2.81(1H, m), 2.94–3.08(1H, m), 3.43(3H, s), 4.20–4.35(2H, m), 5.54(1H, d, J=12.8), 5.62(1H, d, J=12.2), 5.63(1H, s), 7.33–7.63(4H, m), 7.85(1H, d, J=1.8), 8.34(1H, d, J=1.2). |
| F-76 | $^1$H-NMR(CDCl$_3$) δ ppm: 2.72–2.82(1H, m), 2.94–3.08(1H, m), 3.42(3H, s), 4.22–4.37(2H, m), 5.57(1H, s), 5.60(1H, d, J=12.2), 5.75(1H, d, J=12.2), 7.31–7.62(7H, m). |
| F-87 | $^1$H-NMR(CDCl$_3$) δ ppm: 2.21(3H, s), 2.65–2.79(1H, m), 2.93–3.07(1H, m), 3.39(3H, s), 4.17–4.34(2H, m), 5.20(1H, d, J=12.2), 5.42(1H, d, J=12.2), 5.60(1H, s), 7.29–7.60(8H, m). |

TABLE 36

| No | Physical data |
|---|---|
| F-103 | $^1$H-NMR(CDCl$_3$) δ ppm: 2.25(3H, s), 2.65–2.79(1H, m), 2.94–3.07(1H, m), 3.40(3H, s), 4.21–4.35(2H, m), 5.23(1H, d, J=12.2), 5.45(1H, d, J=12.8), 5.61(1H, s), 7.32–7.76(8H, m). |
| F-323 | $^1$H-NMR(CDCl$_3$) δ ppm: 1.18(6H, d, J=6.1), 1.94(3H, s), 2.31(2H, dd, J=12.8, 11.0), 2.65–3.05(2H, m), 3.39(3H, s), 3.46(2H, dd, J=12.8, 2.5), 3.55–3.70(2H, m), 4.17–4.34(2H, m), 4.89(1H, d, J=11.6), 5.11(1H, d, J=12.2), 5.57(1H, s), 7.29–7.57(4H, m). |
| G-36 | $^1$H-NMR(CDCl$_3$) δ ppm: 2.06(3H, s), 2.07(3H, s), 2.17(3H, s), 2.31(3H, s), 3.36(3H, s), 4.91(1H, d, J=12.2), 4.97(1H, d, J=12.2), 5.51(1H, s), 6.61(1H, s), 6.70(1H, d, J=7.3), 7.03(1H, d, J=7.9), 7.33–7.52(4H, m). |

TABLE 36-continued

| No | Physical data |
|---|---|
| G-448 | $^1$H-NMR(CDCl$_3$) δ ppm: 1.26(3H, t, J=7.3), 2.05(3H, s), 2.07(3H, s), 2.16(3H, s), 2.30(3H, s), 3.50(2H, qd, J=7.3, 1.8), 4.93(1H, d, J=12.2), 4.98(1H, d, J=12.2), 5.62(1H, s), 6.61(1H, s), 6.70(1H, d, J=7.9), 7.03(1H, d, J=7.3), 7.33–4.55(4H, m). |
| H-1 | $^1$H-NMR(CDCl$_3$) δ ppm: 2.45(3H, s), 3.39(3H, s), 4.97(1H, d, J=11.0), 5.13(1H, d, J=11.6), 5.86(1H, s), 6.82–6.86(2H, m), 6.99(1H, t, J=7.3), 7.28–7.52(6H, m). |
| H-36 | $^1$H-NMR(CDCl$_3$) δ ppm: 2.07(3H, s), 2.32(3H, s), 2.44(3H, s), 3.40(3H, s), 4.93(1H, d, J=11.6), 5.09(1H, d, J=11.6), 5.88(1H, s), 6.63(1H, s), 6.71(1H, d, J=7.3), 7.02(1H, d, J=7.3), 7.40–7.54(4H, m). |
| I-1 | mp 66~67.5° C. |
| I-12 | mp 87~88° C. |
| I-41 | $^1$H-NMR(CDCl$_3$) δ ppm: 2.20(3H, s), 3.41(3H, s), 3.54(3H, s), 4.94(1H, d, J=12.8), 5.10(1H, d, J=12.8), 5.72(1H, s), 6.72(1H, d, J=8.6), 6.82(1H, d, J=1.2), 5.95(1H, d, J=1.2), 7.04–7.54(6H, m). |
| I-81 | $^1$H-NMR(CDCl$_3$) δ ppm: 2.15(3H, s), 3.41(3H, s), 3.59(3H, s), 5.24(1H, d, J=12.2), 5.30(1H, d, J=12.2), 5.85(1H, s), 5.83(1H, s), 5.97(1H, d, J=1.2), 7.30-7.65(9H, m). |

TABLE 37

| No | Physical data |
|---|---|
| I-449 | $^1$H-NMR(CDCl$_3$) δ ppm: 1.26(3H, t, J=7.3), 2.20(3H, s), 3.46–3.64(2H, m), 3.55(3H, s), 4.95(1H, d, J=12.8), 5.10(1H, d, J=12.8), 5.84(1H, s), 6.72(1H, d, J=8.6), 6.82(1H, d, J=1.2), 6.94(1H, d, J=1.2), 7.04–7.54(6H, m). |
| J-36 | $^1$H-NMR(CDCl$_3$) δ ppm: 2.19(3H, s), 2.29(3H, s), 3.45(3H, s), 5.13(1H, d, J=12.3), 5.27(1H, d, J=12.3), 5.67(1H, s), 6.65(1H, s), 6.67(1H, d, J=7.3), 7.01 (1H, d, J=7.3), 7.12–7.69(7H, m), 8.53(1H, dd, J=4.9, 1.8). |
| K-36 | $^1$H-NMR(CDCl$_3$) δ ppm: 2.13(3H, s), 2.30(3H, s), 3.40(3H, s), 4.95(1H, d, J=12.2), 5.05(1H, d, J=1 2.2), 5.63(1H, s), 6.59(1H, s), 6.69(1H, d, J=7.3), 7.02(1H, d, J=7.3), 7.20–7.64(6H, m), 8.50(1H, dd, J=4.9, 1.8), 8.56(1H, d, J=2.4). |
| L-41 | $^1$H-NMR(CDCl$_3$) δ ppm: 2.17(3H, s), 3.47(3H, s), 5.05(1H, d, J=12.2), 5.19(1H, d, J=12.2), 5.94(1H, s), 6.83(1H, dd, J=7.3, 1.8), 7.10–7.13(2H, m), 7.40–7.71(4H, m), 8.36(1H, s). |

TABLE 38

| No | Physical data |
|---|---|
| A-75 | $^1$H-NMR(CDCl$_3$) δ ppm: 2.21(3H, s), 3.35(3H, s), 5.51(1H, s), 5.91(1H, s), 6.87(1H, s), 7.11(1H, dd, J=7.9, 1.2), 7.35–7.67(3H; m), 8.53(1H, s) |
| A-258 | $^1$H-NMR(CDCl$_3$) δ ppm: 2.18(3H, s), 3.37(3H, s), 5.57(1H, s), 5.89(1H, s), 7.15(1H, dd, J=7.9, 1.8), 7.33–7.66(3H, m), 1.97(1H, d, J=1.8), 8.18(1H, s) |
| A-260 | $^1$H-NMR(CDCl$_3$) δ ppm: 2.22(3H, s), 3.38(3H, s), 5.58(1H, s), 5.95(1H, s), 6.49(1H, s), 7.16(1H, dd, J=7.9, 1.2), 7.33–7.75(7H, m), 8.35(1H, s) |
| A-365 | $^1$H-NMR(CDCl$_3$) δ ppm: 1.53(1.57)(3H, d, J=6.7), 2.17(2.23)(3H, s), 3.30(3.39) (3H, s), 5.22–5.31(1H, m), 5.56(5.74)(1H, s), 5.69(5.88)(1H, s), 7.24–7.65(8H, m), 8.29(8.33)(1H, s) |
| A-372 | $^1$H-NMR(CDCl$_3$) δ ppm: 1.57(1.61)(3H, d, J=6.7), 2.17(2.23)(3H,.s), 3.28(3.39)(3H, s), 5.29–5.39(1H, m), 5.62(5.72)(1H, s), 5.70(5.85)(1H, s), 7.31–7.65(5H, m), 8.33(8.38)(1H, s) |
| A-376 | $^1$H-NMR(CDCl$_3$) δ ppm: 1.52(1.56)(3H, d, J=6.7), 2.18(2.23)(3H, s), 3.33(3.40) (3H, s), 5.18–5.28(1H, m), 5.59(5.72)(1H, s), 5.70(5.86)(1H, s), 7.13–7.65(7H, m), 8.31(8.34)(1H, s) |
| A-381 | $^1$H-NMR(CDCl$_3$) δ ppm: 2.22(3H, s), 2.43(3H, s), 3.48(3H, s), 5.80(1H, s), 6.30(1H, s), 7.39–7.53(5H, m), 7.70(1H, d, J=7.3), 7.86–7.93(3H, m), 8.67(1H, s) |
| A-382 | $^1$H-NMR(CDCl$_3$) δ ppm: 2.22(3H, s), 2.42(3H, s), 3.48(3H, s), 5.79(1H, s), 6.29(1H, s), 7.07–7.15(2H, m), 7.42–7.54(2H, m), 7.70(1H, dd, J=7.3, 1.2), 7.86–7.94(3H, m), 8.67(1H, s) |
| A-384 | $^1$H-NMR(CDCl$_3$) δ ppm: 2.23(3H, s), 2.41 (3H, s), 3.49(3H, s), 5.81 (1H, s), 6.27(1H, s), 7.32–7.92(8H, m), 8.67(1H, s) |
| A-388 | $^1$H-NMR(CDCl$_3$) δ ppm: 2.22(3H, s), 2.40(3H, s), 2.42(3H, s), 3.48(3H, s), 5.79(1H, s), 6.31(1H, s), 7.18–7.83(7H, m), 7.87(1H, dd, J=7.3, 1.8), 8.67(1H, s) |
| A-391 | $^1$H-NMR(CDCl$_3$) δ ppm: 2.22(3H, s), 2.42(3H, s), 3.48(3H, s), 3.86(3H, s), 5.79(1H, |

TABLE 38-continued

| No | Physical data |
|---|---|
| | s), 6.32(1H, s), 6.91–6.97(2H, m), 7.41–7.53(2H, m), 7.70(1H, dd, J=7.3, 1.2), 7.85–7.92(3H, m), 8.68(1H, s) |
| A-392 | mp 60.0~64.0° C. |
| A-396 | mp 104.0~106.0° C. |

TABLE 39

| No | Physical data |
|---|---|
| A-503 | $^1$H-NMR(CDCl$_3$) δ ppm: 2.23(3H, s), 2.38(3H, s), 3.48(3H, s), 5.82(1H, s), 6.24(1H, s), 7.29–7.60(5H, m), 7.69(1H, dd, J=7.3, 1.8), 7.88(1H, dd, J=7.3, 1.2), 8.63(1H, s) |
| A-512 | $^1$H-NMR(CDCl$_3$) δ ppm: 2.23(3H, s), 2.40(3H, s), 3.48(3H, s), 5.83(1H, s), 6.26(1H, s), 7.29–7.55(6H, m), 7.69(1H, dd, J=7.3, 1.8), 7.89(1H, dd, J=7.3, 1.8), 8.65(1H, s) |
| A-504 | $^1$H-NMR(CDCl$_3$) δ ppm: 2.23(3H, s), 2.42(3H, s), 3.49(3H, s), 5.80(1H, s), 6.27(1H, s), 7.27–7.82(7H, m), 7.89(1H, dd, J=7.3, 1.8), 8.66(1H, s) |
| A-505 | $^1$H-NMR(CDCl$_3$) δ ppm: 2.22(3H, s), 2.42(3H, s), 3.48(3H, s), 5.80(1H, s), 6.27(1H, s), 7.25–7.28(2H, m), 7.42–7.55(2H, m), 7.70(1H, dd, J=7.3, 1.2), 7.87–7.96(3H, m), 8.67(1H, s) |
| A-509 | $^1$H-NMR(CDCl$_3$) δ ppm: 2.21(3H, s), 2.38(3H, s), 3.47(3H, s), 5.70(1H, s), 6.31(1H, s), 6.52(1H, dd, J=3.1, 1.8), 6.93(1H, d, J=3.7), 7.41–7.54(2H, m), 7.57(1H, d, J=12), 7.71(1H, dd, J=7.3, 1.2), 7.85(1H, dd, J=7.3), 8.77(1H, s) |
| A-508 | $^1$H-NMR(CDCl$_3$) δ ppm: 2.23(3H, s), 2.40(3H, s), 3.49(3H, s), 5.80(1H, s), 6.24(1H, s), 7.44–7.56(2H, m), 7.69–7.75(3H, m), 7.90(1H, dd, J=7.9, 1.8), 8.65(1 H, s), 8.69–8.74(2H, m) |
| A-510 | $^1$H-NMR(CDCl$_3$) δ ppm: 2.21(3H, s), 2.46(3H, s), 3.48(3H, s), 5.76(1H, s), 6.34(1H, s), 7.08(1H, dd, J=4.9, 3.7), 7.41–7.53(4H, m), 7.71(1H, dd, J=7.9; 1.8), 7.83(1H, dd, J=7.9, 1.8), 8.68(1H, s) |
| A-507 | $^1$H-NMR(CDCl$_3$) δ ppm: 2.23(3H, s), 2.45(3H, s), 3.49(3H, s), 5.81(1H, s), 6.26(1H, s), 7.33–7.55(3H, m), 7.70(1H, dd, J=7.3, 1.2), 7.89(1H, dd, J=7.3, 1.8), 8.19–8.23(1H, m), 8.65–8.68(2H, m), 9.09(1H, d, J=1.8) |
| A-506 | $^1$H-NMR(CDCl$_3$) δ ppm: 2.23(3H, s), 2.51(3H, s), 3.49(3H, s), 5.83(1H, s), 6.26(1H, s), 7.30–7.78(5H, m), 7.92(1H, dd, J=7.3, 1.8), 8.18(1H, d, J=7.9), 8.63(1H, s), 8.67(1H, d, J=1.8) |
| A-386 | $^1$H-NMR(CDCl$_3$) δ ppm: 2.22(3H, s), 2.40(3H, s), 3.48(3H, s), 5.79(3H, s), 6.28(1H, s), 7.43–7.90(8H, m), 8.66(1H, s) |
| E-385 | $^1$H-NMR(CDCl$_3$) δ ppm: 2.36(3H, s), 2.44(3H, s), 3.44(3H, s), 5.89(1H, s), 6.10(1H, s), 7.35–7.89(7H, m), 8.01(1H, dd, J=7.3, 1.2), 8.76(1H, s) |
| E-392 | $^1$H-NMR(CDCl$_3$) δ ppm: 2.36(3H, s), 2.48(3H, s), 3.45(3H, s), 5.91(1H, s), 6.10(1H, s), 7.40–7.70(5H, m), 8.02(1H, dd, J=7.3, 1.2), 8.09(1H, d, J=7.9), 8.18(1H, s), 8.77(1H, s) |
| E-396 | $^1$H-NMR(CDCl$_3$) δ ppm: 2.36(3H, s), 2.43(3H, s), 3.44(3H, s), 5.90(1H, s), 6.08(1H, s), 7.39–8.03(7H, m), 8.76(1H, s) |

TABLE 40

| No | Physical data |
|---|---|
| E-503 | $^1$H-NMR(CDCl$_3$) δ ppm: 2.36(3H, s), 2.40(3H, s), 3.43(3H, s), 5.91(1H, s), 6.07(1H, s), 7.19–7.52(5H, m), 7.65(1H, dd, J=7.3, 1.2), 8.00(1H, dd, J=7.9, 1.8), 8.71(1H, s) |
| E-365 | $^1$H-NMR(CDCl$_3$) δ ppm: 1.56(1.57)(3H, d, J=6.7), 2.32(2.35)(3H, s), 3.33(3.38)(3H, s), 5.29(5.31)(1H, q, J=6.7), 5.71(5.80)(1H, s), 5.74(5.78)(1H, s), 7.29–7.63(8H, m), 8.47(8.49)(1H, s) |
| E-373 | $^1$H-NMR(CDCl$_3$) δ ppm: 1.57(1.59)(3H, d, J=6.7), 2.31(2.35)(3H, s), 3.32(3.38)(3H, s), 5.38(5.39)(1H, q, J=6.7), 5.72(5.76)(1H, s), 5.72(5.79)(1H, s), 7.28–7.63(8H, m), 8.51 (8.53)(1H, s) |
| E-361 | $^1$H-NMR(CDCl$_3$) δ ppm: 1.59(1.60)(3H, d, J=6.7), 2.32(2.35)(3H, s), 3.31(3.37)(3H, s), 5.33(1H, q, J=6.7), 5.73(5.80)(1H, s), 5.76(5.79)(1H, s), 7.23–7.65(9H, m), 8.47(8.51)(1H, s) |
| E-372 | $^1$H-NMR(CDCl$_3$) δ ppm: 1.59(1.60)(3H, d, J=6.7), 2.32(2.35)(3H, s), 3.32(3.38)(3H, s), 5.38(1H, q, J=6.7), 5.73(5.76)(1H, s), 5.75(5.81)(1H, s), 7.29–7.64(8H, |

TABLE 40-continued

| No | Physical data |
|---|---|
| | m), 8.50(8.53)(1H, s) |
| E-504 | $^1$H-NMR(CDCl$_3$) δ ppm: 2.36(3H, s), 2.45(3H, s), 3.44(3H, s), 5.90(1H, s), 6.10(1H, s), 7.26–8.03(8H, m), 8.75(1H, s) |
| E-505 | $^1$H-NMR(CDCl$_3$) δ ppm: 2.36(3H, s), 2.46(3H, s), 3.44(3H, s), 5.90(1H, s), 6.10(1H, s),7.25–7.69(5H, m), 7.93–8.04(3H, m), 8.77(1H, s) |
| E-384 | $^1$H-NMR(CDCl$_3$) δ ppm: 2.36(3H, s), 2.44(3H, s), 3.44(3H, s), 5.90(1H, s), 6.10(1H, s), 7.32–8.07(8H, m), 8.76(1H, s) |
| E-388 | $^1$H-NMR(CDCl$_3$) δ ppm: 2.35(3H, s), 2.40(3H, s), 2.45(3H, s), 3.44(3H, s), 5.90 (1H, s), 6.14(1H, s), 7.22–7.83(7H, m), 8.01(1H, dd, J=7.3, 1.2), 8.76(1H, s) |
| E-382 | $^1$H-NMR(CDCl$_3$) δ ppm: 2.36(3H, s), 2.45(3H, s), 3.44(3H, s), 5.89(1H, s), 6.11 (1H, s), 7.07–7.14(2H, m), 7.38–7.51(2H, m), 7.67(1H, dd, J=7.9, 1.2), 7.88-8.03(3H, m), 8.77(1H, s) |
| E-393 | $^1$H-NMR(CDCl$_3$) δ ppm: 2.36(3H, s), 2.47(3H, s), 3.44(3H, s), 5.90(1H, s), 6.09 (1H, s), 7.39–7.53(2H, m), 7.66–7.69(3H, m), 8.01–8.04(3H, m), 8.76(1H, s) |
| E-507 | $^1$H-NMR(CDCl$_3$) δ ppm: 2.36(3H, s), 2.48(3H, s), 3.44(3H, s), 5.90(1H, s), 6.10(1H, s), 7.34–8.67(7H, m), 8.77(1H, s), 9.09(1H, d, J=1.8) |
| E-508 | mp 143~144° C. |

TABLE 41

| No | Physical data |
|---|---|
| N-87 | $^1$H-NMR(CDCl$_3$) δ ppm: 1.45–1.74(4H, m), 2.04–2.36(2H, m), 2.13(3H, s), 2.65–2.70(2H, m), 3.42(3H, s), 5.22(1H, d, J=12.2), 5.28(1H, d, J=12.2), 5.81(1H, s), 7.30–7.61(8H, m) |
| N-36 | $^1$H-NMR(CDCl$_3$) δ ppm: 1.53–1.75(4H, m), 2.13-2.37(2H, m), 2.16(3H, s), 2.32(3H, s), 2.69(2H, t, J=6.1), 3.43(3H, s), 4.99(1H, d, J=12.2), 5.08(1H, d, J=1.2.2), 5.73(1H, s), 6.68–6.71(2H, m), 7.02(4H, d, J=7.9), 7.33–7.61(4H, m) |
| N-55 | $^1$H-NMR(CDCl$_3$) δ ppm: 1.55–1.75(4H, m), 2.08(3H, sy, 2.12–2.37(2H, m), 2.23 (3H, s), 2.28(3H, s), 2.68(2H, t, J=6.1), 3.42(3H, s), 4.96(1H, d, J=12.2), 5.06(1H, d, J=12.2), 5.73(1H, s), 6.75(1H, s), 6.63(1H, s), 7.33–7.65(4H, m) |
| N-84 | $^1$H-NMR(CDCl$_3$) δ ppm: 1.52–1.73(4H, m), 2.08–2.35(2H, m), 2.14(3H, s), 2.68(2H, td, J=6.1, 2.4), 3.42(3H, s), 5.21(1H, d, J=12.2), 5.28(1H, d, J=12.2), 5.82(1H, s), 6.99–7.08(2H, m), 7.31–7.64(6H, m) |
| N-103 | $^1$H-NMR(CDCl$_3$) δ ppm: 1.51–1.73(4H, m), 2.07–2.18(1H, m), 2.18(3H, s), 2.26–2.37(1H, m), 2.65–2.71(2H, m), 3.43(3H, s), 5.25(1H, d, J=12.2), 5.31(1H, d, J=12.8), 5.82(1H, s), 7.32–7.75(8H, m) |
| N-110 | $^1$H-NMR(CDCl$_3$) δ ppm: 1.52–1.74(4H, m), 2.07–2.37(2H, m), 2.12(3H, s), 2.68(2H, td, J=6.1, 1.8), 3.43(3H, s), 5.22(1H, d, J=12.8), 5.29(1H, d, J=12.2), 5.80(1H, s), 7.32–7.72(7H, m) |
| N-324 | $^1$H-NMR(CDCl$_3$) δ ppm: 1.18(6H, d, J=6.7), 1.56–1.73(4H, m), 1.85(3H, s), 2.04–2.16(1H, m), 2.23–2.35(2H, m), 2.69(2H, t, J=6.7), 3.42(3H, s), 3.42–3.68(4H, m), 4.90(1H, d, J=11.6), 4.97(1H, d, J=12.2), 5.80(1H, s),7.30–7.59(4H, m) |
| O-87 | $^1$H-NMR(CDCl$_3$) δ ppm: 1.57–1.83(4H, m), 2.1–2.20(4H, m), 2.32–2.42(1H, m), 2.61–2.65(2H, m), 3.42(3H, s), 5.21(1H, d, J=12.8), 5.43(1H, d, J=12.8), 5.83(1H, s), 7.23–7.66(8H, m) |
| O-103 | $^1$H-NMR(CDCl$_3$) δ ppm: 1.63–1.83(4H, m), 2.10–2.22(4H, m), 2.33–2.41 (1H, m), 2.61–2.66(2H, m), 3.42(3H, s), 5.24(1H, d, J=12.8), 5.47(1H, d, J=12.8), 5.83(1H, s), 7.29–7.46(3H, m), 7.58–7.63(3H, m), 7.74(2H, d, J=8.55) |
| O-324 | $^1$H-NMR(CDCl$_3$) δ ppm: 1.18(6H, d, J=6.1), 1.65–1.81(4H, m), 1.91(3H, s), 2.18–2.35(4H, m), 2.60–2.63(2H, m), 3.41 (3H, s), 3.41–3.48(2H, m), 3.59–3.66(2H, m), 4.90(1H, d, J=12.2), 5.12(1H, d, J=12.2), 5.81(1H, s), 7.29–7.42(3H, m), 7.55–7.58(1H, m) |
| O-66 | mp 91.0~92.0° C. |
| O-69 | $^1$H-NMR(CDCl$_3$) δ ppm: 1.61–1.84(4H, m), 2.08–2.19(1H, m), 2.34–2.44(1H, m), 2.60–2.65(2H, m), 3.45(3H, s), 5.53(1H, d, J=12.8), 5.63(1H, d, J=12.8), 5.87(1H, s), 7.30–7.66(4H, m), 7.84(1H, d, J=1.8), 8.33(1H, t, J=1.2) |

The following Test Examples illustrate the effects of the fungicide and insecticide of this invention.

I. Controlling effects on various plant diseases by foliage application (pot experiment)

Experimental Method

A test compound was dissolved in a small amount of N,N-dimethylformamide, and the solution was diluted to a given concentration with distilled water containing a spreader. Thus, a liquid sample to be tested was prepared. The liquid sample was sprayed to test plants, and 24 hours thereafter, pathogens were inoculated by the method described below.

The percent control was calculated according to the following equation:

$$\text{Percent control (\%)} = 100 \times \frac{\begin{array}{c}\text{severity, number of}\\\text{lesions, etc. in}\\\text{untreated plot}\end{array} - \begin{array}{c}\text{severity, number of}\\\text{lesions, etc. in}\\\text{treated plot}\end{array}}{\begin{array}{c}\text{severity, number of lesions, etc. in}\\\text{untreated plot}\end{array}}$$

Test Example 1

Controlling effect on *Pyricularia oryzae*

Two-week rice seedlings (cv.: AICHIASAHI) were transplanted in plastic cups (each 9 cm in diameter) and cultivated further 2 weeks. The test compound in the form of a solution or a suspension was sprayed to the foliage of the rice seedlings, to which a conidia suspension of *Pyricularia oryzae* cultured in an oatmeal medium was inoculated by spraying. After the inoculation, the test plant was kept in a moist chamber (28° C., 100% R.H.) for 24 hours, followed by cultivation in a greenhouse for 5 days. Six days after the inoculation, the number of lesions on the leaves of the inoculated plant was measured to calculate the percent control.

The results are as follows.

TABLE 42

| Compound No. | Controlling effect on *Pyricularia oryzae* by foliage application at 500 ppm (percent control) |
|---|---|
| A-67 | 90 |
| A-68 | 90 |
| A-69 | 100 |
| A-87 | 90 |
| A-102 | 97 |
| A-103 | 100 |
| A-110 | 90 |
| A-147 | 97 |
| A-323 | 100 |
| A-327 | 97 |
| A-373 | 97 |
| A-385 | 97 |
| A-393 | 97 |
| E-100 | 90 |
| I-41 | 90 |
| Reference: Fthalide | 97 |

Test Example 2

Controlling effect on *Sphaerotheca fuliginea*

Seeds of cucumber (cv.: TSUKUBASHIROIBO) were sown in plastic cups (each 9 cm in diameter), followed by cultivation for 2 to 3 weeks. The liquid test sample in the form of a solution or suspension was sprayed on the surface of their first leaves. The pathogen was inoculated to the leaves by spraying a conidia suspension of *Sphaerotheca fuliginea* which had been cultured on the cucumber leaves. After the inoculation, the plants were kept in a greenhouse at 20° C. for 10 days. Then, the infected area on the leaf was observed, and the percent control was calculated.

The results are as follows.

TABLE 43

| Compound No. | Controlling effect on *Sphaerotheca fuliginea* by foliage application at 500 ppm (percent control) |
|---|---|
| A-12 | 100 |
| A-31 | 100 |
| A-36 | 100 |
| A-41 | 100 |
| A-44 | 100 |
| A-55 | 100 |
| A-67 | 100 |
| A-68 | 100 |
| A-69 | 100 |
| A-87 | 100 |
| A-102 | 100 |
| A-103 | 100 |
| A-110 | 100 |
| A-327 | 100 |
| A-323 | 100 |

TABLE 44

| Compound No. | Controlling effect on *Sphaerotheca fuliginea* by foliage application at 500 ppm (percent control) |
|---|---|
| A-373 | 100 |
| A-385 | 100 |
| A-393 | 100 |
| D-36 | 100 |
| D-41 | 100 |
| D-103 | 100 |
| E-12 | 100 |
| E-36 | 100 |
| E-103 | 100 |
| E-323 | 100 |
| F-103 | 100 |
| I-12 | 100 |
| I-41 | 100 |
| Reference: Fenarimol | 100 |

Test Example 3

Controlling effect on *Botrytis cinerea*

The seeds of cucumber (cv.: TSUKUBASHIROIBO) were sown in plastic cups (each 9 cm in diameter), followed by cultivation for 2 to 3 weeks. The test compound in the form of a solution or suspension was sprayed to the surface of their first leaves, and mycelial disks (4 mm φ) of *Botrytis cinerea* cultured on the potato sucrose agar medium were put on the leaf surfaces to inoculate the cucumber seedlings with the pathogen. The plants were kept in a moist chamber at 20° C. for 3 days. The diameter of the lesions on the leaves was measured and the percent control was calculated.

The results are as follows.

TABLE 45

| Compound No | Controlling effect on *Botrytis cinerea* by foliage application at 500 ppm (percent control) |
|---|---|
| A-36 | 70 |
| A-67 | 70 |
| A-87 | 70 |
| A-102 | 70 |
| A-110 | 70 |
| A-323 | 70 |
| A-327 | 70 |

TABLE 45-continued

| Compound No | Controlling effect on *Botrytis cinerea* by foliage application at 500 ppm (percent control) |
|---|---|
| E-323 | 70 |
| I-41 | 70 |
| Reference: iprodione | 100 |

Test Example 4

Controlling effect on *Pseudoperonospora cubensis*

The seeds of cucumber (var.: TSUKUBASHIROIBO) were sown in plastic cups (each 9 cm in diameter), followed by cultivation for 2 to 3 weeks. The test compound in the form of a solution or suspension was sprayed to the surface of their first leaves, and a zoosporangia suspension of *Pseudoperonospora cubensis* cultured on cucumber leaves was dropped on the above leaf surfaces to inoculate the test plants with the pathogen. After the inoculation, the plants were kept in a moist chamber at 20° C. for 10 days. Then, the area of the lesions around the inoculum were observed and the percent control was calculated.

The results are as follows.

TABLE 46

| Compound No. | Controlling effect on *Pseudoperonospora cubensis* by foliage application at 500 ppm (percent control) |
|---|---|
| A-65 | 100 |
| A-69 | 100 |
| A-385 | 100 |
| A-393 | 100 |
| Reference: benalaxyl | 99 |

Test Example 5

Controlling effect on *Erysiphe graminis* f. sp. tritici

The seeds of wheat (cv.: NORIN No. 61) were sown in plastic cups (each 9 cm in diameter), followed by cultivation for 2 to 3 weeks. The test compound in the form of a solution or suspension was sprayed to the seedlings, and conidia of *Erysiphe graminis* f sp. tritici cultured on wheat leaves were dropped on the test plants to inoculate the plants with the pathogen. After the inoculation, the plants were kept in a greenhouse at 20° C. for 10 days. The infected area on the leaf was observed, and the percent control was calculated.

The results are as follows.

TABLE 47

| Compound No. | Controlling effect on *Erysiphe graminis* f. sp. *tritici* by foliage application at 500 ppm (percent control) |
|---|---|
| A-12 | 97 |
| A-22 | 90 |
| A-36 | 97 |
| A-67 | 90 |
| A-68 | 90 |
| A-69 | 90 |
| A-76 | 97 |
| A-102 | 97 |
| A-103 | 97 |

TABLE 47-continued

| Compound No. | Controlling effect on *Erysiphe graminis* f. sp. *tritici* by foliage application at 500 ppm (percent control) |
|---|---|
| A-323 | 97 |
| D-36 | 97 |
| D-41 | 90 |
| D-65 | 90 |
| D-67 | 90 |
| D-68 | 97 |
| D-69 | 97 |
| D-87 | 90 |
| D-103 | 97 |
| E-36 | 90 |
| F-69 | 100 |
| I-12 | 90 |
| Reference: Fenarimol | 97 |

II. Insecticidal Activity

Test Example 6

Insecticidal activity against Myzus persicae

A lamina of Chinese cabbage (3 cm in diameter) was put upside down on 0.3% agar gel, inoculated with apterous mature insects, and kept at 25° C. for a day to count the number of delivery young insects. After removing the mature insects, test liquid at a given concentration was sprayed to the young insects on the lamina of Chinese cabbage. The number of the insects killed after 48 hours at 25° C. was counted to judge the effect. The test liquid was adjusted to a given concentration by dissolving the compound in a small amount of N,N-dimethylformamide and being diluted with distilled water containing a surfactant.

The compounds No. A-385, 392, 393, and 396 gave the killed insects percentage of 90, 100, 88, and 100% at 250 ppm, respectively.

Effect of Invention

As described above, this invention provides novel α-substituted benzyl heterocyclic derivatives having potent fungicidal and insecticidal activity and low toxicity, intermediates for their production, and fungicides and insecticides containing them as an active ingredient.

What is claimed is:

1. A compound of the formula (I):

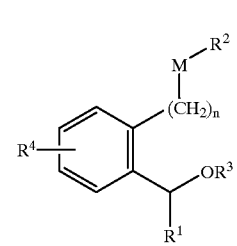

wherein $R^1$ is an optionally substituted imidazoyl is optionally substituted aryl; $R^3$ is hydrogen, alkyl, alkenyl, or alkynyl; $R^4$ is hydrogen, alkyl, alkoxy, halogen, nitro, cyano, or halogenated alkyl; M is (1) oxygen, (2) $S(O)_i$ wherein i is 0, 1, or 2, (3) $NR^5$ wherein $R^5$ is hydrogen, alkyl, or acyl, (4) —Q—N=C($R^6$)— wherein Q is oxygen or $NR^7$ wherein $R^7$ is hydrogen alkyl, or acyl; $R^6$ is hydrogen, alkyl, acyl, alkylthio, alkylsulfinyl, alkylsulfonyl, halogenated alkyl, cyano, alkoxycarbonyl, alkoxyalkyl, optionally substituted amino, or cycloalkyl, or $R^2$ and $R^6$ taken together form a monocyclic group or a fused polycyclic group optionally having a hetero atom, (5) —B—C($R^8$)=N— wherein B is oxygen or sulfur and $R^8$ is hydrogen, alkyl, acyl, alkylthio, alkylsulfinyl, alkylsulfonyl, halogenated alkyl, cyano, alkoxycarbonyl, alkoxyalkyl, optionally substituted amino, or cycloalkyl, (6) —CH=N—N=C($R^9$)— wherein $R^9$ is hydrogen, alkyl, cyano, cycloalkyl, or halogenated alkyl, or (7) —CH=N—A—($CR^{10}R^{11}$)m— wherein $R^{10}$ and $R^{11}$ are independently hydrogen, alkyl, cyano, or halogenated alkyl, A is oxygen or $NR^{12}$ wherein $R^{12}$ is hydrogen, alkyl, or acyl, and m is 0 or 1; and n is 0, 1, or 2.

2. The compound of claim 1 wherein $R^1$ is optionally substituted imidazol-2-yl.

3. The compound of claim 1 wherein $R^1$ is 1-methylimidazol-2-yl.

4. The compound of claim 1 wherein $R^2$ is phenyl optionally substituted with 1 to 3 substituents selected from the group consisting of halogen, lower alkyl, halogenated lower alkyl, lower alkoxy, halogenated lower alkoxy, lower alkylthio, phenyl, and phenoxy.

5. The compound of claim 1 wherein $R^2$ is phenyl unsubstituted or substituted with 1 to 3 substituents selected from the group consisting of lower alkoxy, halogenated lower alkoxy, halogenated lower alkyl, halogen and lower alkyl.

6. The compound of claim 1 wherein $R^2$ is phenyl, 2-chlorophenyl, 3-chlorophenyl, 4-chlorophenyl, 2-methylphenyl, 3-methylphenyl, 4-methylphenyl, 2,5-dimethylphenyl, 3,4-dimethylphenyl, 4-chloro-2-methylphenyl, 3,4-dichlorophenyl, 3-trifluoromethylphenyl, 4-trifluoromethylphenyl, 4-methoxyphenyl, 3-trifluoromethyloxyphenyl, 4-trifluoromethyloxyphenyl.

7. The compound of claim 1 wherein $R^3$ is methyl.

8. The compound of claim 1 wherein $R^4$ is hydrogen.

9. The compound of claim 1 wherein M is oxygen, —O—N=C($R^6$)—, —CH=N—N=C($R^9$)—, or —CH=N—O—($CR^{10}R^{11}$)m— wherein each symbol is as defined in claim 1.

10. The compound of claim 1 wherein M is oxygen, —O—N=C($CH_3$)—, —O—N=C($SCH_3$)—, —O—N=C(CN)—, —O—N=C($CF_3$)—, —CH=N—N=C($CH_3$)—, —CH=N—O—CH($CH_3$)—, or —CH=N—O—C($CH_3$)$_2$—.

11. The compound of claim 1 which is;
a compound wherein $R^1$ is 1-methylimidazol-2-yl, $R^2$ is 2-methylphenyl, $R^3$ is methyl, $R^4$ is hydrogen, M is oxygen and n is 1; or
a compound wherein $R^1$ is 1-methylimidazol-2-yl, $R^2$ is 4-chloro-2-methylphenyl, $R^3$ is methyl, $R^4$ is hydrogen, M is oxygen and n is 1.

12. An agrochemical composition which contains the compound of claim 1 as an active ingredient.

13. A fungicidal composition which contains the compound of claim 1 as an active ingredient.

14. An insecticidal composition which contains the compound of claim 1 as an active ingredient.

15. The compound of claim 1 which is a compound of the formula (IV):

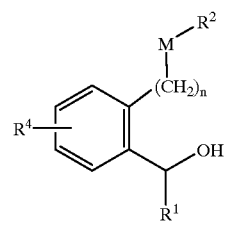

IV wherein each symbol is as defined in claim 1.

16. A compound of the formula (X):

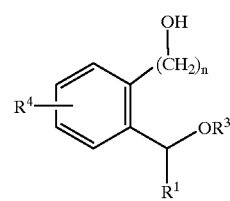

X wherein each symbol is as defined in claim 1.

17. A compound of the formula (XII):

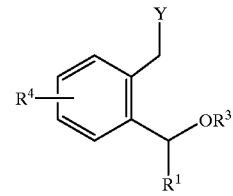

XII wherein Y is halogen and the other symbols are as defined in claim 1.

18. A method for controlling or preventing phytopathogenic fungi which comprises applying as an active ingredient a compound of claim 1, its salt, or its hydrate to a locus where phytopathogenic fungi propagated or will propagate.

19. A method for manufacturing a fungicidal composition which comprises admixing the compound of claim 1, its salt or its hydrate, and a carrier.

* * * * *